(12) United States Patent
Kleefeld et al.

(10) Patent No.: US 9,771,389 B2
(45) Date of Patent: Sep. 26, 2017

(54) TYLOSIN DERIVATIVES AND METHOD FOR PREPARATION THEREOF

(71) Applicants: BAYER ANIMAL HEALTH GMBH, Leverkusen (DE); The Kitasako Institute, Tokyo (JP)

(72) Inventors: Gerd Kleefeld, Neuss (DE); Robrecht Froyman, Heusden-Zolder (DE); Carolin Ludwig, Meerbusch (DE); Satoshi Omura, Tokyo (JP); Toshiaki Sunazuka, Chiba (JP); Hirose Tomoyasu, Kanagawa (JP); Sugawara Akihiro, Tokyo (JP); Shiomi Kazuro, Tokyo (JP)

(73) Assignees: THE KITASAKO INSTITUTE, Tokyo (JP); BAYER ANIMAL HEALTH GMBH, Leverkusen (DE)

( * ) Notice: Subject to any disclaimer, the term of this patent is extended or adjusted under 35 U.S.C. 154(b) by 0 days.

(21) Appl. No.: 14/891,762

(22) PCT Filed: May 23, 2014

(86) PCT No.: PCT/EP2014/060665
§ 371 (c)(1),
(2) Date: Nov. 17, 2015

(87) PCT Pub. No.: WO2014/187957
PCT Pub. Date: Nov. 27, 2014

(65) Prior Publication Data
US 2016/0108077 A1    Apr. 21, 2016

(30) Foreign Application Priority Data
May 23, 2013    (EP) .................................... 13169009

(51) Int. Cl.
*C07H 17/08*    (2006.01)

(52) U.S. Cl.
CPC .................................... *C07H 17/08* (2013.01)

(58) Field of Classification Search
None
See application file for complete search history.

(56) References Cited

U.S. PATENT DOCUMENTS

| | | | | |
|---|---|---|---|---|
| 5,545,624 A | * | 8/1996 | Hecker | C07H 17/08 514/30 |
| 2006/0014707 A1 | | 1/2006 | Fu et al. | |

FOREIGN PATENT DOCUMENTS

| | | |
|---|---|---|
| EP | 0124216 A1 | 2/1984 |
| EP | 0240264 A2 | 10/1987 |
| EP | 0606747 A1 | 7/1994 |
| EP | 2019112 A1 | 1/2009 |
| WO | 94/02496 A1 | 2/1994 |
| WO | 96/09312 A1 | 3/1996 |
| WO | 03/043642 A1 | 11/2002 |
| WO | 03/039558 A1 | 5/2003 |
| WO | 03/089446 A2 | 10/2003 |
| WO | 03/089447 A1 | 10/2003 |
| WO | 2005/118610 A2 | 12/2005 |
| WO | 2007/071370 A1 | 6/2007 |
| WO | 2008/012343 A2 | 1/2008 |
| WO | 2009/064953 A1 | 5/2009 |
| WO | 2013/076169 A1 | 5/2013 |

OTHER PUBLICATIONS

Ahammed S. et al., The Journal of Organic Chemistry, vol. 76, 2011, pp. 7235-7239.
Tornoe, C.W. et al., Journal of Organic Chemistry, vol. 67, 2002, pp. 3057-3064.
Brouillette E. et al., Veterinary Microbiology, vol. 101, 2004, pp. 253-262.
Cattle Death Loss: the National Statistics Service (NASS), United State Department of Agriculture, May 5, 2006.
Chan T.R. et al., Organic Letters, vol. 6, No. 17, 2004, pp. 2853-2855.
Debono, M. et al., Journal of Antibiotics, vol. XLII, No. 8, 1989, pp. 1253-1267.
Ducruix, A. et al., Journal of the Chemical Society, Chemical Communications, 1976, pp. 947-948.
Fleisher D., et al., Advanced Drug Delivery Reviews, vol. 19, 1996, pp. 115-130.

(Continued)

*Primary Examiner* — Layla Berry
(74) *Attorney, Agent, or Firm* — McBee Moore Woodward & Vanik IP, LLC; Susan McBee; David Woodward

(57) ABSTRACT

The present invention relates to new macrolide derivatives, in particular new tylosin derivatives of the formula (IIa), a pharmaceutical or veterinary composition comprising the derivatives; a method for preparation thereof; a method for treating and/or preventing bacterial infections in an animal, wherein the method comprises administering the derivatives or the composition; and a use of the derivatives for the manufacture of medicaments for treating and/or preventing bacterial infections in an animal.

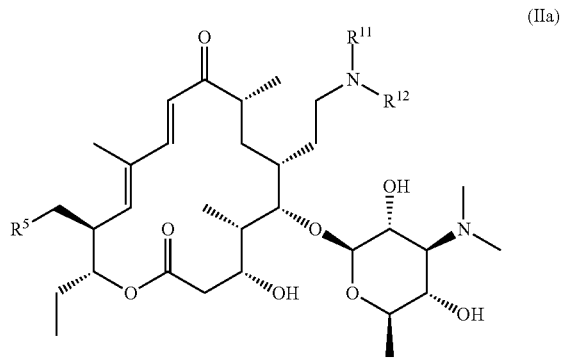

(IIa)

11 Claims, No Drawings

(56) References Cited

OTHER PUBLICATIONS

Fu, H. et al., Bioorganic & Medicinal Chemistry Letters vol. 16, 2006, pp. 1259-1266.
Galli U. et al., European Journal of Medicinal Chemistry, vol. 55, 2012, pp. 58-66.
Gruel P. et al., Advanced Drug Delivery Reviews, vol. 50, 2001, pp. 245-259.
Hansen, J. L. et al., Molecular Cell, vol. 10, 2002, pp. 117-128.
Harper M. et al., FEMS Microbiol Lett, vol. 265, 2006, pp. 1-10.
Hirose, T. et al., Heterocycles, vol. 69, 2006, pp. 55-61.
Huisgen, Pure & Applied Chemistry, vol. 61, No. 4, 1989, pp. 613-628.
International Preliminary Report on Patentability; PCT/EP2014/060665; mailed Nov. 23, 2015.
International Search Report with Written Opinion; PCT-EP2014/060665; mailed Aug. 4, 2014.
Journal of Medicinal Chemistry vol. 39, No. 10, May 10, 1996, pp. 1935-2102.
Kirst, H. A. et al., Journal of Medicinal Chemistry, vol. 31, No. 8, 1988, pp. 1631-1641.
Kolb, H. C. et al., Angewandte Chemie International Edition, vol. 40, 2001, pp. 2004-2021.
Lima-Neto R.G. et al., Molecules, vol. 17, 2012, pp. 5882-5892.
Ma Z. et al., Journal of Medicinal Chemistry, vol. 44, 2001, pp. 4137-4156.
Mamidyala S.K. et al., The Royal Society of Chemistry, vol. 49, 2013, pp. 8407-8409.
Marshall S.A. et al., Journal of Clinical Microbiology, vol. 34, No. 8, 1996, pp. 2027-2029.
McGuire J. M. et al., Antibiotics and Chemotherapy, vol. XI, No. 5, 1961, pp. 320-327.
Mereu, A. et al., Bioorganic & Medicinal Chemistry Letters, vol. 16, 2006, pp. 5801-5804.
Morin et al., Tetrahedron Letters, No. 54, 1970, pp. 4737-4740.
Omura S. Tetrahedron, vol. 67, 2011, pp. 6420-6459.
Omura, S., Journal of the American Chemical Society, vol. 97, No. 14, 1975, pp. 4001-4009.
Pinnert-Sindico, S. et al., Rhone-Poulenc Research Labs., Paris, Antibiotics Annual, vol. 2, 1955, pp. 1954-1955.
Pokhodylo N.T. et al., Russian Journal of Organic Chemistry, vol. 46, No. 6, 2010, pp. 894-897.
Rostovtsev, V. V. et al., Angewandte Chemie International Edition, vol. 41, No. 14, 2002, pp. 2596-2599.
Sashida H. et al., Chemicla and Pharmaceutical Bulletin, vol. 35, No. 10, 1987, pp. 4110-4116.
Shpigel N.Y. et aL, Research in Veterinary Science, vol. 56, 1994, pp. 62-68.
Smith R.A., Journal of Animal Science, vol. 76, 1998, pp. 272-274.
Sugawara, A. et al., Bioorganic & Medicinal Chemistry Letters, vol. 17, 2007, pp. 6340-6344.
Omura et al., "Chemical Modification of Macrolides," Macrolide Antibiotics, 2nd Edition, Chapter 3, 2002:99-108.
Omura et al., "Chemical Modification of Macrolides," Macrolide Antibiotics, 2nd Edition, Chapter 3, 2002:109-115.
Omura et al., "Chemical Modification of Macrolides," Macrolide Antibiotics, 2nd Edition, Chapter 3, 2002:116-119.
Omura et al., "Chemical Modification of Macrolides," Macrolide Antibiotics, 2nd Edition, Chapter 3, 2002:120-138.
Omura et al., "Chemical Modification of Macrolides," Macrolide Antibiotics, 2nd Edition, Chapter 3, 2002:139-162.
Omura et al., "Chemical Modification of Macrolides, " Macrolide Antibiotics, 2nd Edition, Chapter 3, 2002:163-180.
Woodward, Dr. R. B.,"Struktur and Biogenese der Makrolide Eine neue Klasse von Naturstoffen," Angewwandte Chemie, 1957, 69(1/2):50-58.

* cited by examiner

TYLOSIN DERIVATIVES AND METHOD FOR PREPARATION THEREOF

BACKGROUND OF THE INVENTION

The present invention relates to new macrolide derivatives, in particular new tylosin derivatives; a pharmaceutical or veterinary composition comprising any of the derivatives; a method for preparation thereof; a method for treating and/or preventing bacterial infections in an animal, wherein the method comprises administering any of the derivatives or the composition; and a use of the derivatives for the manufacture of medicaments for treating and/or preventing bacterial infections in an animal.

Macrolides in generally have a chemical structure of 12-, 14- or 16-membered macrocyclic group (aglycone) substituted with 1 to 3 substituents such as neutral sugars, deoxy sugars or amino sugars. Macrolides have a wide spectrum of antibacterial activities against for example *Pneumococcus* spp, *Streptococcus* spp, *Hemophilus influenzae*, *Staphylococcus aureus*, *Actinobacillus* spp, *Pasteurella* spp and atypical pathogen such as *Mycoplasma*, *Legionella* or *Chlamydia* that is resistant to other drugs. Consequently, macrolides have been used for the treatment of among others a variety of respiratory tract infections. A variety of macrolides have been discovered or synthesized until now, typically including tylosin represented by the following formula:

Tylosin has been used for the treatment of infections of Gram-positive bacterium and *Mycoplasma* in farm animals.

In order to further expand the spectrum of tylosin and to improve its oral bioavailability, a number of tylosin derivatives have been tested. Examples of such tylosin derivatives typically include among others tilmicosin and tulathromycin (tulathromycin belongs to a different class of compounds) represented by the following formulae, respectively:

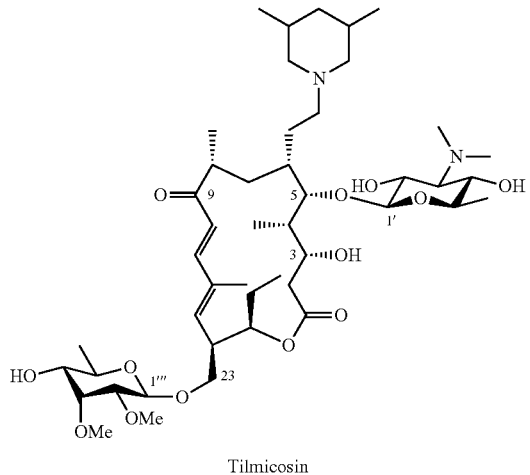

Tilmicosin

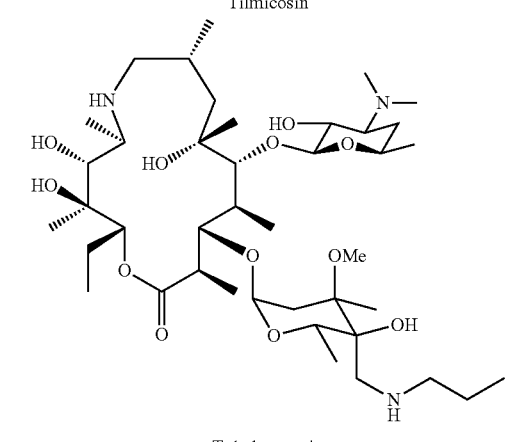

Tulathromycin

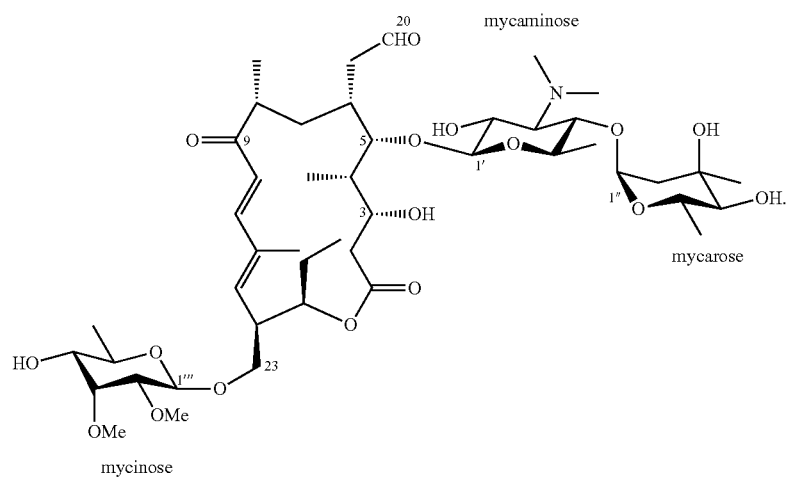

Tilmicosin and tulathromycin are useful for the treatment of pasteurellosis caused by Gram negative *bacillus* such as *Pasteurella* or *Mannheimia*. They are the most commonly used and important antibiotics in farm animals.

However, new antibiotics are inextricably associated with the emergence of resistant bacteria. Accordingly, there is still a need to provide new antibiotics.

The backgrounds may be reflected in the following patent and Non-patent References:

PATENT REFERENCES

EP 124216
EP 240264
EP 606747
WO 1996-009312
WO 2003-039558
WO 2003-039558
WO 2003-043642
WO 2003-089446
WO 2003-089447
WO 2005-118610
WO 2005-118610
WO 2007-071370
WO 2009-064953

NON-PATENT REFERENCES

Woodward, R. B., *Angew. Chem.* 1957, 69, 50-58.
Brockmann, H.; Henkel, W. *Naturwissenshaften.* 1950, 37, 138.
Pinnert-Sindico, S.; Ninet, L.; Preud'homme, J.; Cosar, C. Rhone-Poulenc Research Labs., Paris, *Antibiotics Ann.* 1955, 2, 1954-1955.
Hansen, J. L.; Ippolito, J. A.; Ban, N.; Nissen, P.; Moore, P. B.; Steitz, T. A. *Molecular Cell.* 2002, 10, 117.
Ducruix, A.; Pascard, C.; Nakagawa, A.; Omura, S. *J. Chem. Soc. Chem. Commun.* 1976, 947.
Morin, R. B.; Gorman, M.; Hamill, R. L. *Tetrahedron Lett.* 1970, 11, 4737-4740.
Omura, S.; Nakagawa, A.; Neszmelyi, A.; Gero, S. D.; Sepulcre, A. M.; Piriou, F.; Lukacs, G. *J. Am. Chem. Soc.* 1975, 97, 4001-4009.
McGuire, J. M. *Antibiot. Chemother.* 1961, 11, 320-327.
Debono, M.; Kirst, H. A.; Omura, S. *J. Antibiot.* 1989, 42, 1253-1267.
Shokichi Nakajima: Resistant to the drugs—fight against infections-, Maruzen, Tokyo (2000), Cattle death loss: the National Statistics Service (NASS). *United States Department of Agriculture*, May, 5 (2006)
Rogert A. Smith: Impact of disease on feedlot performance: A review. *J. Anim. Sci.* 1998, 76, 276-274.
Maina, H.; John, D. B.; Ben A. *FEMS Microbiol. Lett.* 2006, 256, 1-10.
Yasutomo Arashima: Misunderstanding of "pasteurellosis" in Japan.
Kolb, H. C.; Finn, M. G.; Sharpless, K. B. *Angew. Chem., Int. Ed.* 2001, 40, 2004-2021.
Rostovtsev, V. V.; Green, L. G.; Fokin, V. V.; Sharpless, K. B. *Angew. Chem., Int. Ed.* 2002, 41, 2596-2599.
a) Huisgen, R. *Pure Applied Chem.* 1989, 61, 613-628. b) Huisgen, R. In 1,3-*Dipolar Cycloaddition Chemistry*; Padwa, A., Ed.; Wiley: New York, 1984, 1, 1-176.
a) Rostovtsev, V. V.; Green, L. G.; Fokin, V. V.; Sharpless, K. B. *Angew. Chem., Int. Ed.* 2002, 41, 2596-2599.

*Macrolide antibiotics. Chemistry, biology, and practice.* Edited by Omura, S. Academical Press, Inc., Orlando, Fla. 32887. 1984.
Hirose, T.; Sunazuka, T.; Noguchi, Y.; Yamaguchi, Y.; Hanaki, H.; Sharpless, K. B.; Omura, S. *Heterocycles,* 2006, 69, 55-61.
Kirst, H. A.; Toth, J. E.; Debono, M.; Willard, K. E.; Truedell, B. A.; Ott, J. L.; Counter, F. T.; Felty-Duckworth, A. M.; Pekarek, R. S. *J. Med. Chem.* 1988, 31, 1631-1641.
Mereu, A.; Moriggi, E.; Napoletano, M.; Regazzoni, C.; Manfredini, S.; Mercurio, T. P.; Pellacini, F. *Bioorg. Med. Chem. Lett.* 2006, 16, 5801-5804.
Rostovtsev, V. V.; Green, L. G.; Forkin, V. V.; Sharpless, K. B. *Angew. Chem., Int. Ed.* 2002, 41, 2597.
Chan, T. R.; Hilgraf, R.; Sharpless, K. B.; Fokin, V. V. *Org. Lett.* 2004, 6, 2853-2855.
Noboru Kagei: Journal of preventive medicine, 1985, 199, 32-33.
Yoshio Ueno, Satoshi Omura: "Microbial Chemistry, 2nd. edition", Nankodo (1986).
Tsuyoshi Yamada: "Fight between bacterium and human", Ishiyaku Publishers, Inc.
Satoshi Omura, Ruiko Oiwa: Chemistry and Biology, 1982, 20, 10-12.
Cassinelli, G.; Cotta, G.; D'Amico, G.; Della, B. C.; Grein, A.; Mazzoleni, R.; Ricciardi, M. L.; Tintinelli, R. *Arch. Mikrobiol.* 1970, 70, 197-210.
Bruna, D. C.; Ricciardi, M. L.; Sanfilippo, A. *Antimicrob. Agents. Chemother.* 1973, 3, 708-710.
Hamill, R. L.; Hoehn, M. M. *J. Antibiot.* 1964, 17, 100-103.
Probst, G. W.; Hoehn, M. M.; Woods, B. L. *Antimicrob. Agents. Chemother.* 1966, 789-795.
Haneisi, T.; Arai, M.; Kitano, N.; Yamamoto, S. *J. Antibiot.* 1974, 27, 339-342.
Masatoshi Inukai, Hiroshi Mishima: Current Chemistry special 9 "Advanced antibiotics", Tokyo Kagakudojin, 1987, 37-43.
a) Omura, S.; Otoguro, K.; Imamura, N.; Huga, H.; Takahashi, Y.; Masuma, R., Tanaka, Y.; Tanaka, H.; Xue-hui, S.; En-tai, Y. *J. Antibio,* 1987, 40, 623-629. b) Imamura, N.; Kuga, H.; Otoguro, K.; Tanaka, H.; Omura, S. *J. Antibio.* 1989, 42, 156-158.
Giencke, W.; Ort, O.; Stark, H. *Liebigs. Ann. Chem.* 1989, 671-676.
Moss, R. A.; Landon, M. J.; Luchter, K. M.; Mamantov, A. *J. Am. Chem. Soc.* 1972, 94, 4392-4394.
Tsuzuki, K.; Yan, F.; Otoguro, K.; Omura, S. *J. Antibiot.* 1991, 44, 774-784.
Kar, A.; Argade, N. P. *Tetrahedron,* 2003, 59, 2991.
Nam, N. H.; Kim, Y.; You, Y. J.; Hong, D. H.; Kim, H. M.; Ahn, B. Z. *Bioorg. Med. Chem. Lett.* 2002, 12, 1955-1958.
Naora, H.; Ohnuki, T.; Nakamura, A. *Bull. Chem. Soc. Jpn.* 1988, 61, 993-994.
Thakkalapally, A.; Benin, V. *Tetrahedron.* 2005, 61, 4939-4948.

SUMMARY OF THE INVENTION

The object of the present invention is to provide new chemical entities effective in the treatment or prevention of infections in animals caused by bacteria such as:

*Staphylococcus* spp, *Streptococcus* spp, *Enterococcus* spp, *Neisseria* spp, *Moraxella* spp, *Corynebacterium* spp, *Lactobacillus* spp, *Bacillus* spp, *Listeria* spp, *Erysipelothrix* spp, *Arcanobacterium* spp, *Vibrio* spp *Aeromonas* spp,

*Escherichia* spp, *Klebsiella* spp, *Proteus* spp, *Salmonella* spp, *Shigella* spp, *Morganella* spp, *Citrobacter* spp, *Enterobacter* spp, *Serratia* spp, *Erwinia* spp, *Yersinia* spp, *Pseudomonas* spp, *Alcaligenes* spp, *Burkholderia* spp, *Phyllobacterium* spp, *Acinetobacter* spp, *Stenotrophomonas* spp, *Haemophilus* spp, *Actinobacillus* spp, *Bordetella* spp, *Pasteurella* spp, *Brucella* spp, *Campylobacter* spp, *Capnytophaga* spp, *Francisella* spp, *Helicobacter* spp, *Legionella* spp, *Mycoplasma* spp, *Ureaplasma* spp, *Bartonella* spp, *Chlamydia* spp, *Coxiella* spp, *Ehrlichia* spp, *Rickettsia* spp, *Borrelia* spp, *Leptospira* spp, *Treponema* spp, *Brachyspira* spp, *Veillonella* spp, *Peptostreptococcus* spp, *Peptococcus* spp, *Bacteroides* spp, *Porphyromonas* spp, *Prevotella* spp, *Fusobacterium* spp, *Clostridium* spp, *Actinomyces* spp, *Propionibacterium* spp, *Eubacterium* spp, *Lactobacillus* spp, *Bifidobacterium* spp.

More specifically the present compounds can be used in the treatment or prevention of bacterial infections caused by gram-positive bacteria such as staphylococcal, streptococcal, *Lactobacillus acidophilus, Corynebacterium diphtheriae, Propionibacterium acnes, Actinomyces bovis, Mycobacterium tuberculosis, Mycobacterium leprae, Bacillus* or *Clostridium* and gram-negative bacteria such as *Pasteurella, Mannheimia* or *Mycoplasma* in animals.

In one embodiment, the present invention provides compounds represented by the formula (IIa):

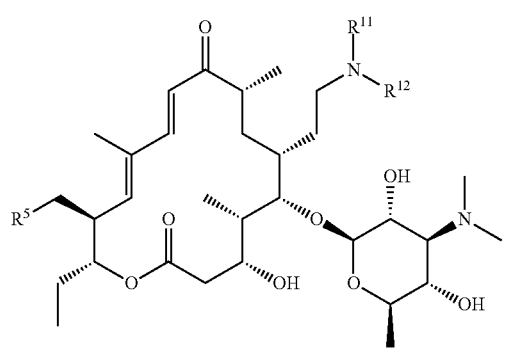

(IIa)

or a pharmaceutically acceptable salt, ester, prodrug or solvate thereof;

wherein, $R^{11}$ and $R^{12}$ are each independently selected from hydrogen;

CHO;

$C_1$-$C_6$—X, wherein X is selected from the group consisting of hydroxyl or protected hydroxyl, halogen, and $N_3$, CN;

C1-C6-alkyl, optionally substituted with one or more substituents selected from the group consisting of halogen, aryl, substituted aryl, heterocyclic and substituted heterocyclic;

C2-C6-alkenyl, optionally substituted with one or more substituents selected from the group consisting of halogen, aryl, substituted aryl, heterocyclic and substituted heterocyclic;

C2-C6-alkynyl, optionally substituted with one or more substituents selected from the group consisting of halogen, aryl, substituted aryl, heterocyclic and substituted heterocyclic;

C3-C14-cycloalkyl;

substituted C3-C14-cycloalkyl;

aryl;

substituted aryl;

heterocyclic;

substituted heterocyclic;

or $R^{11}$ and $R^{12}$ taken with the nitrogen atom to which they are connected form $N_3$ or a 3- to 7-membered ring which may optionally contain a hetero function selected from the group consisting of —O—, —NH—, —N(C1-C6-alkyl)-, —N(aryl)-, —N(heteroaryl)-, —S—, —S(O)— and —S(O)$_2$—; C3-C14 cycloalkyl; and wherein $R^5$ is hydrogen;

hydroxyl;

protected hydroxyl;

halogen;

—$N_3$; or

N—$Y_2$, wherein each Y is independently selected from the group consisting of hydrogen and C1-C6-alkyl, or the two Y taken with the nitrogen atom to which they are connected form a 3- to 7-membered ring.

In a further embodiment, the present invention provides compounds of said formula (IIa), wherein:

$R^5$ is hydroxy.

In another embodiment, the present invention provides compounds of said formula (IIa), wherein:

at least $R^{11}$ or $R^{12}$ is C1-C6-alkyl, optionally substituted with one or more substituents selected from the group consisting of halogen, aryl, substituted aryl, heterocyclic and substituted heterocyclic, and wherein preferably at least $R^{11}$ or $R^{12}$ is C1-C6-alkyl, substituted with one substituent selected from the group consisting of heterocyclic and substituted heterocyclic, and wherein more preferably at least $R^{11}$ or $R^{12}$ is C1-C3-alkyl, substituted with one substituent selected from the group consisting of heterocyclic and substituted heterocyclic, and wherein even more preferably at least $R^{11}$ or $R^{12}$ is C1-C3-alkyl, substituted with a 1,2,3-triazole substituted at position 4 with one substituent selected from the group consisting of heterocyclic and substituted heterocyclic.

In still another embodiment the present invention provides compounds of said formula (IIa), wherein:

one of $R^{11}$ and $R^{12}$ is C1-C6-alkyl, substituted with one substituent selected from the group consisting of heterocyclic and substituted heterocyclic, and the other one of $R^{11}$ and $R^{12}$ is hydrogen or C1-C6-alkyl, optionally substituted with one or more substituents selected from the group consisting of halogen, aryl, substituted aryl, heterocyclic and substituted heterocyclic; wherein preferably one of $R^{11}$ or $R^{12}$ is C1-C3-alkyl, substituted with one substituent selected from the group consisting of heterocyclic and substituted heterocyclic, and the other one of R11 and R12 is hydrogen or C1-C3-alkyl, optionally substituted with one or more substituents selected from the group consisting of halogen, aryl, substituted aryl, heterocyclic and substituted heterocyclic, wherein even more preferably one of $R^{11}$ and $R^{12}$ is C1-C2-alkyl, substituted with a 1,2,3-triazole substituted at position 4 with one substituent selected from the group consisting of heterocyclic and substituted heterocyclic, and the other one of $R^{11}$ and $R^{12}$ is hydrogen or C1-C2-alkyl, optionally substituted with one substituent selected from the group consisting of aryl and substituted aryl.

In another embodiment, the present invention provides a method for preparing a compound of the formula (IIa):

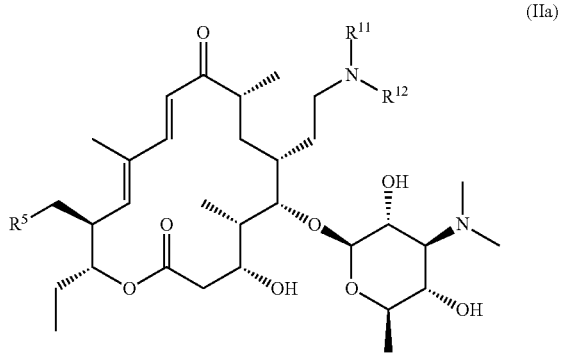

(IIa)

wherein $R^5$, $R^{11}$ and $R^{12}$ are as defined above;

which method comprises at least one of the following steps following steps (i), (ii), (iii) and/or (iv):

(i) reacting O-mycaminosyltylonolide (OMT):

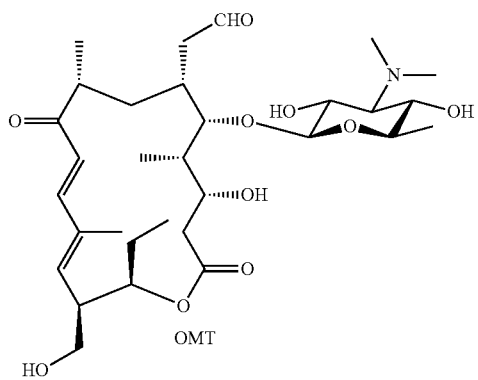

with an amine of the general formula $NR^1R^2$ to form a compound of the following formula (IIb)

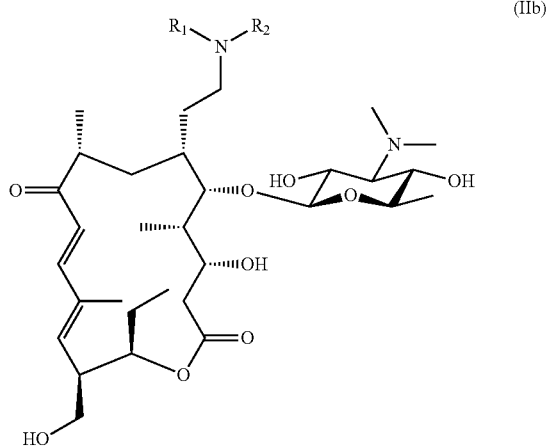

(IIb)

wherein
$R^1$ is as defined for $R^{11}$ and $R^{12}$ in the formula (IIa) above, and $R^2$ is C2-C6-alkynyl, optionally substituted with one or more substituents selected from the group consisting of halogen, aryl, substituted aryl, heterocyclic and substituted heterocyclic; or (ii) reacting the resulting compound of the formula (IIb), wherein
$R^1$ is as defined for $R^{11}$ and $R^{12}$ in the formula (IIa) above, and $R^2$ is C2-C6-alkynyl, optionally substituted with one or more substituents selected from the group consisting of halogen, aryl, substituted aryl, heterocyclic and substituted heterocyclic with an R—$N_3$, wherein R is as defined for $R^{11}$ or $R^{12}$ in the formula (IIa) above, in the presence of a copper catalyst to form a compound of the formula (IIa); or (iii) reacting O-mycaminosyltylonolide (OMT):

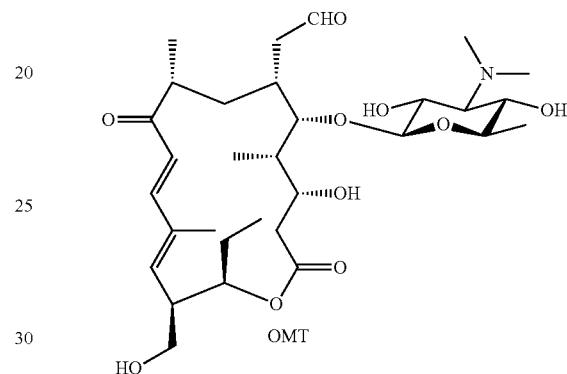

with an amine of the general formula $NR^1R^2$ to form a compound of the following formula (IIb)

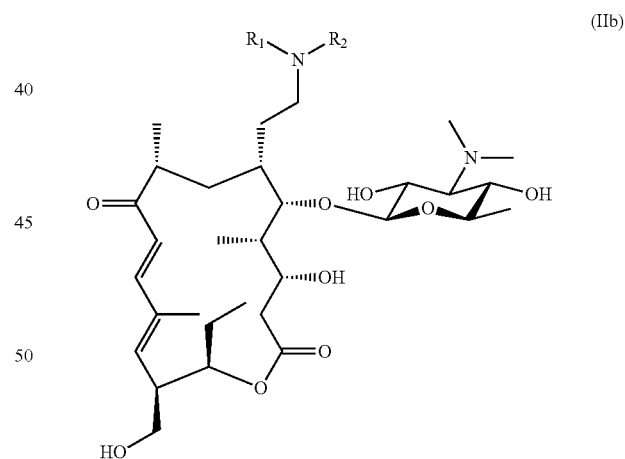

(IIb)

wherein
$R^1$ is as defined for $R^{11}$ and $R^{12}$ in the formula (IIa) above, and $R^2$ is C1-C6-alkyl, bearing one $N_3$-substituent and being optionally substituted with one or more substituents selected from the group consisting of halogen, aryl, substituted aryl, heterocyclic and substituted heterocyclic; or (iv) reacting the resulting compound of the formula (IIb), wherein
$R^1$ is as defined for $R^{11}$ and $R^{12}$ in the formula (IIa) above, and R² is C1-C6-alkyl, bearing one N₃-substituent and being optionally substituted with one or more substituents selected from the group consisting of halogen, aryl, substituted aryl, heterocyclic and substituted heterocyclic with an R—C≡CH, wherein R is as defined for $R^{11}$ or $R^{12}$ in the formula (IIa) above, in the presence of a copper catalyst to form a compound of the formula (IIa).

In further embodiment, the present invention provides a pharmaceutical or veterinary composition comprising the compound of the present invention. Such composition may be used for the treatment or the prevention of bacterial infections or disorders associated with bacterial infections in animals, which include among others mammal, fish or birds. The pharmaceutical or veterinary composition may include or may be used simultaneously, sequentially or contiguously with one or more other antibiotics.

Preferred in this context are pharmaceutical or veterinary compositions comprising the compound of formula (IIa) as mentioned before. These compositions, as well as the compounds of formula (IIa) as mentioned before, may preferably be used for the treatment of mastitis in non-human mammals, such as cattle, camel, buffalo, goat or sheep, more preferably in ruminants that are used for milk production for human consumption, such as cattle, buffalo, sheep, and goat.

In further embodiment, the present invention provides uses of the compounds of the present invention for manufacturing a medicament for treatment or prevention of bacterial infections or disorders associated with bacterial infections in animals.

In still further embodiments, the present invention provides compounds according to the embodiments as mentioned before for use as a medicament, preferably the compounds of formula (IIa) as mentioned before.

In yet another embodiments, the present invention provides compounds or pharmaceutical or veterinary compositions according to the embodiments as mentioned before for use in the treatment or prevention of bacterial infections or disorders associated with bacterial infections in an animal, preferably the compounds of formula (IIa) as mentioned before.

The compounds of the present invention has different chemical structure from tylosin or tilmicosin, while the present compounds may have antibacterial activities similar to or greater than those of tylosin or tilmicosin. Therefore, the compounds of the present invention may be used as a substitute for tylosin or tilmicosin, particularly to treat infections or related disorders caused by tylosin- or tilmicosin-resistant bacteria. Accordingly, the compound of the present invention is useful in the treatment or prevention of bacterial infections or disorders associated with bacterial infections in animals.

DETAILED DESCRIPTION OF THE PREFERRED EMBODIMENTS

The terms as used herein have the meaning as defined below or as understood by an artisan of ordinary skill in fields of organic chemistry, biochemistry, medical sciences, pharmaceutical sciences, bacteriology and the like.

The terms "C1-C3-alkyl", "C1-C6-alkyl", "C1-C12-alkyl" or the like, as used herein, refer to saturated, straight- or branched-chain hydrocarbon radicals containing between one and three, one and six or one and twelve carbon atoms, respectively. The term "C0-C3-alkyl" means a bond or C1-C3-alkyl. Examples of C1-C3-alkyl radicals include methyl, ethyl, propyl and isopropyl, and examples of C1-C6-alkyl radicals include, but are not limited to, methyl, ethyl, propyl, isopropyl, n-butyl, tert-butyl, neopentyl and n-hexyl, and examples of C1-C12-alkyl radicals include, but are not limited to, methyl, ethyl, propyl, isopropyl, n-butyl, tert-butyl, neopentyl, n-hexyl, n-octyl, n-decyl and n-dodecyl.

The term "C2-C6-alkenyl" or the like, as used herein, refers to straight- or branched-chain hydrocarbon radicals containing between two and six carbon atoms with one or more double bonds in the chain. Examples of C2-C6-alkenyl include, but are not limited to, propenyl, isobutenyl, 1,3-hexadienyl, n-hexenyl and 3-pentenyl.

The term "C2-C6-alkynyl" or the like, as used herein, refers to straight- or branched-chain hydrocarbon radicals containing between two and six carbon atoms with one or more triple bonds in the chain optionally containing one or more double bond. Examples of C2-C6-alkynyl include, but are not limited to, propynyl, isopentynyl, 1,3-hexadiynyl, n-hexynyl, 3-pentynyl, and 1-hexen-3-ynyl.

The term "aryl", as used herein, refers to unsubstituted carbocyclic mono-, di- or tri-cyclic aromatic groups including, but not limited to, phenyl, 1- or 2-naphthyl, anthracene, phenanthrene and the like.

The term, "C3-C14-cycloalkyl", as used herein refer to unsubstituted monocyclic mono-, di- or tri-cyclic groups where each carbocyclic ring consisting cycloalkyl comprises 3 to 7 carbon atoms, respectively, such as for example, cyclopropyl, cyclobutyl, cyclopentyl, cyclohexyl, and cycloheptyl.

The terms "halo" and "halogen", as used herein, refer to an atom selected from fluorine, chlorine, bromine and iodine.

The term "heteroaryl", as used herein, refers to a mono-, di- or tri-cyclic aromatic radical having from five to fourteen ring atoms of which one ring atom is selected from S, O and N; zero, one or more ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, triazolyl, tetrazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl", as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to one or two benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic", as used herein, refers to heterocycloalkyl and heteroaryl.

The term "substituted heterocyclic", as used herein, refers to substituted heterocycloallcyl and substituted heteroaryl.

The term "substituted aryl", as used herein refers to an aryl group, as defined herein, substituted by independent replacement of one or more of the hydrogen atoms therein with, for example, but not limited to, F, Cl, Br, I, OH, $NO_2$, CN, C(O)—C1-C6-alkyl, C(O)-aryl, C(O)-heteroaryl, $CO_2$-alkyl, $CO_2$-aryl, $CO_2$-heteroaryl, $CONH_2$, CONH—C1-C6- alkyl, CONH-aryl, CONH-heteroaryl, OC(O)—C1-C6-alkyl, OC(O)-aryl, OC(O)-heteroaryl, OCO$_2$-alkyl, OCO$_2$-aryl, OCO$_2$-heteroaryl, OCONH$_2$, OCONH—C1-C6-alkyl, OCONH-aryl, OCONH-heteroaryl, NHC(O)—C1-C6-alkyl, NHC(O)-aryl, NHC(O)-heteroaryl, NHCO$_2$-alkyl, NHCO$_2$-aryl, NHCO$_2$-heteroaryl, NHCONH$_2$, NHCONH—C1-C6-alkyl, NHCONH-aryl, NHCONH-heteroaryl, SO$_2$—C1-C6-alkyl, SO$_2$-aryl, SO$_2$-heteroaryl, SO$_2$NH$_2$, SO$_2$NH—C1-C6-alkyl, SO$_2$NH-aryl, SO$_2$NH-heteroaryl, C1-C6-alkyl, C3-C7-cycloalkyl, CF$_3$, CH$_2$CF$_3$, CH$_2$Cl$_2$, CH$_2$OH, CH$_2$CH$_2$OH, CH$_2$NH$_2$, CH$_2$SO$_2$CH$_3$, aryl, substituted aryl, heteroaryl, substituted heteroaryl, benzyl, benzyloxy, aryloxy, heteroaryloxy, C1-C6-alkoxy, methoxymethoxy, methoxyethoxy, amino, benzylamino, arylamino, heteroarylamino, C1-C3-alkyl-amino, thio, aryl-thio, heteroarylthio, benzyl-thio, C1-C6-alkyl-thio, or methylthiomethyl.

The term "substituted heteroaryl", as used herein refers to a heteroaryl group as defined herein substituted by independent replacement of one or more of the hydrogen atoms therein with, for example, but not limited to, F, Cl, Br, I, OH, NO$_2$, CN, C(O)—C1-C6-alkyl, C(O)-aryl, C(O)-heteroaryl, CO$_2$-alkyl, CO$_2$-aryl, CO$_2$-heteroaryl, CONH$_2$, CONH—C1-C6-alkyl, CONH-aryl, CONH-heteroaryl, OC(O)—C1-C6-alkyl, OC(O)-aryl, OC(O)-heteroaryl, OCO$_2$-alkyl, OCO$_2$-aryl, OCO$_2$-heteroaryl, OCONH$_2$, OCONH—C1-C6-alkyl, OCONH-aryl, OCONH-heteroaryl, NHC(O)—C1-C6-alkyl, NHC(O)-aryl, NHC(O)-heteroaryl, NHCO$_2$-alkyl, NHCO$_2$-aryl, NHCO$_2$-heteroaryl, NHCONH$_2$, NHCONH—C1-C6-alkyl, NHCONH-aryl, NHCONH-heteroaryl, SO$_2$—C1-C6-alkyl, SO$_2$-aryl, SO$_2$-heteroaryl, SO$_2$NH$_2$, SO$_2$NH—C1-C6-alkyl, SO$_2$NH-aryl, SO$_2$NH-heteroaryl, C1-C6-alkyl, C3-C7-cycloallcyl, CF$_3$, CH$_2$CF$_3$, CH$_2$Cl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, C1-C6-alkoxy, methoxymethoxy, methoxyethoxy, amino, benzylamino, arylamino, heteroarylamino, C1-C3-alkyl-amino, thio, aryl-thio, heteroarylthio, benzyl-thio, C1-C6-alkyl-thio, or methylthiomethyl.

The term "substituted heterocycloalkyl", as used herein, refers to a heterocycloalkyl group, as defined above, substituted by independent replacement of one or more of the hydrogen atoms therein with, for example, but not limited to, F, Cl, Br, I, OH, NO$_2$, CN, C(O)—C1-C6-alkyl, C(O)-aryl, C(O)-heteroaryl, CO$_2$-alkyl, CO$_2$-aryl, CO$_2$-heteroaryl, CONH$_2$, CONH—C1-C6-alkyl, CONH-aryl, CONH-heteroaryl, OC(O)—C1-C6-alkyl, OC(O)-aryl, OC(O)-heteroaryl, OCO$_2$-alkyl, OCO$_2$-aryl, OCO$_2$-heteroaryl, OCONH$_2$, OCONH—C1-C6-alkyl, OCONH-aryl, OCONH-heteroaryl, NHC(O)—C1-C6-alkyl, NHC(O)-aryl, NHC(O)-heteroaryl, NHCO$_2$-alkyl, NHCO$_2$-aryl, NHCO$_2$-heteroaryl, NHCONH$_2$, NHCONH—C1-C6-alkyl, NHCONH-aryl, NHCONH-heteroaryl, SO$_2$—C1-C6-alkyl, SO$_2$-aryl, SO$_2$-heteroaryl, SO$_2$NH$_2$, SO$_2$NH—C1-C6-alkyl, SO$_2$NH-aryl, SO$_2$NH-heteroaryl, C1-C6-alkyl, C3-C7-cycloallcyl, CF$_3$, CH$_2$CF$_3$, CH$_2$Cl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, C1-C6-alkoxy, methoxymethoxy, methoxyethoxy, amino, benzylamino, arylamino, heteroarylamino, C1-C3-alkyl-amino, thio, aryl-thio, heteroarylthio, benzyl-thio, C1-C6-alkyl-thio, or methylthiomethyl.

The term "substituted cycloalkyl", as used herein, refers to a cycloalkyl group, as defined above, substituted by independent replacement of one or more of the hydrogen atoms therein with, for example, but not limited to, F, Cl, Br, I, OH, NO$_2$, CN, C(O)—C1-C6-alkyl, C(O)-aryl, C(O)-heteroaryl, CO$_2$-alkyl, CO$_2$-aryl, CO$_2$-heteroaryl, CONH$_2$, CONH—C1-C6-alkyl, CONH-aryl, CONH-heteroaryl, OC(O)—C1-C6-alkyl, OC(O)-aryl, OC(O)-heteroaryl, OCO$_2$-alkyl, OCO$_2$-aryl, OCO$_2$-heteroaryl, OCONH$_2$, OCONH—C1-C6-alkyl, OCONH-aryl, OCONH-heteroaryl, NHC(O)—C1-C6-alkyl, NHC(O)-aryl, NHC(O)-heteroaryl, NHCO$_2$-alkyl, NHCO$_2$-aryl, NHCO$_2$-heteroaryl, NHCONH$_2$, NHCONH—C1-C6-alkyl, NHCONH-aryl, NHCONH-heteroaryl, SO$_2$—C1-C6-alkyl, SO$_2$-aryl, SO$_2$-heteroaryl, SO$_2$NH$_2$, SO$_2$NH—C1-C6-alkyl, SO$_2$NH-aryl, SO$_2$NH-heteroaryl, C1-C6-alkyl, C3-C7-cycloallcyl, CF$_3$, CH$_2$CF$_3$, CH$_2$Cl$_2$, CH$_2$OH, CH$_2$CH$_2$OH, CH$_2$NH$_2$, CH$_2$SO$_2$CH$_3$, aryl, heteroaryl, benzyl, benzyloxy, aryloxy, heteroaryloxy, C1-C6-alkoxy, methoxymethoxy, methoxyethoxy, amino, benzylamino, arylamino, heteroarylamino, C1-C3-alkyl-amino, thio, aryl-thio, heteroarylthio, benzyl-thio, C1-C6-alkyl-thio, or methylthiomethyl.

The term "amino" includes a group represented by —NH$_2$. The term "substituted amino" indicates amino groups having one or two substituents in place of one or two hydrogen atoms attached to nitrogen atom of the amino group. The term "azide" means a group represented by —N$_3$, which may comprise —N—N≡N or —N═N═N.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known. See, for example, T. H. Greene and P. G. M. Wuts, Protective Groups in Organic Synthesis, 3rd edition, John Wiley & Sons, New York (1999). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy", refers to a hydroxy group protected with a hydroxy protecting group, as defined above, including, for example, but not limited to, benzoyl, acetyl, trimethylsilyl, triethylsilyl, methoxymethyl groups.

"Aldehyde-protecting group", as used herein, refers to an easily removable group which is known to protect an aldehyde group against undesirable reaction during synthetic procedures and to be selectively removable. The use of aldehyde-protecting groups is well known in the art for protecting aldehyde groups against undesirable reactions during a synthetic procedure and many such protecting groups are known. See, for example, T. H. Greene and P. G, M, Wuts, Protective Groups in Organic Synthesis, op. cit. Examples of aldehyde-protecting groups include, but are not limited to, acetals, ketals, O-substituted cyanohydrins, substituted hydrazones, imines and the like.

The term "protected aldehyde" refers to an aldehyde group protected with an aldehyde protecting group, as defined above, including, for example, but not limited to, dimethyl acetyl, dimethoxy methyl, 1,3-dioxolane, 1,3-dioxane and the like.

The compound of the present invention can be prepared, but is not limited to, by any conventional method known to an artisan of ordinary skill, for example according to any one of the methods described below, typically analogous to the method detailed in Examples of the present specification.

The preparation of the present compound can be performed typically by using cycloaddition reaction between azide and acetylene derivative, what is called click chemistry (see, for example Kolb, H. C.; Finn, M. G.; Sharpless, K. B., Angew. Chem., Int. Ed. 2001, 40, 2004-2021 and Rostovtsev, V. V.; Green, L. G.; Fokin, V. V.; Sharpless, K. B., Angew. Chem., Int. Ed. 2002, 41, 2596-2599). The mechanism of the reaction is represented by the following scheme A:

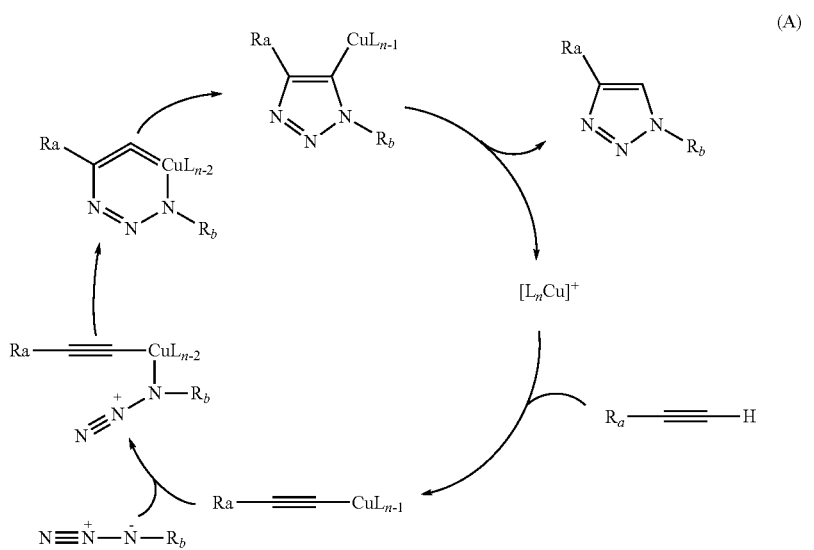

(A)

wherein Ra and Rb indicate any functional groups and LnCu indicates copper catalysis. The click chemistry may be typically characterized by sophisticated functional group selectivity and regio selectivity, mild reaction condition, high yield, and applicability for a wide variety of substituents.

One embodiment for a method for preparing a compound of the formula (IIa):

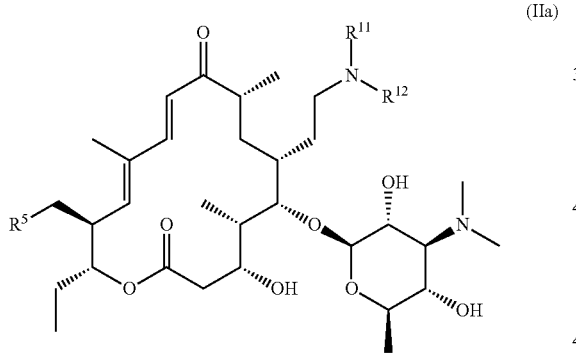

(IIa)

wherein $R^5$, $R^{11}$ and $R^{12}$ are as defined above;
which method comprises following steps:
(i) reacting O-mycaminosyltylonolide (OMT):

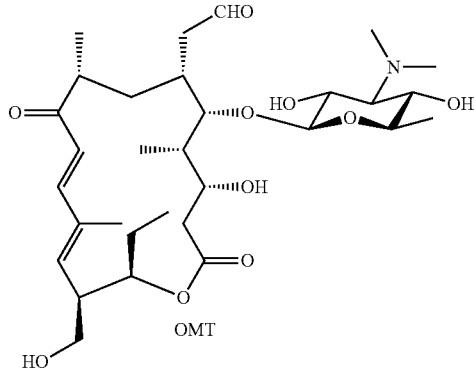

OMT with an amine of the general formula $NR^1R^2$ to form a compound of the following formula (IIb)

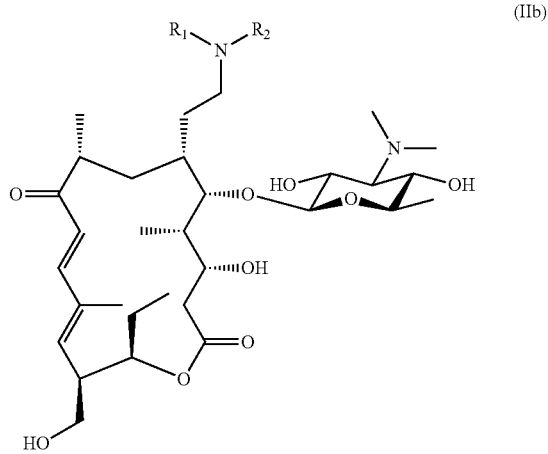

(IIb)

wherein
$R^1$ is as defined for $R^{11}$ and $R^{12}$ in the formula (IIa) above, and
$R^2$ is C2-C6-alkynyl, optionally substituted with one or more substituents selected from the group consisting of halogen, aryl, substituted aryl, heterocyclic and substituted heterocyclic; and
(ii) reacting the resulting compound of the formula (IIb) with an R—$N_3$, wherein R is as defined for $R^{11}$ or $R^{12}$ in the formula (IIa) above, in the presence of a copper catalyst to form a compound of the formula (IIa); or
(iii) reacting O-mycaminosyltylonolide (OMT):

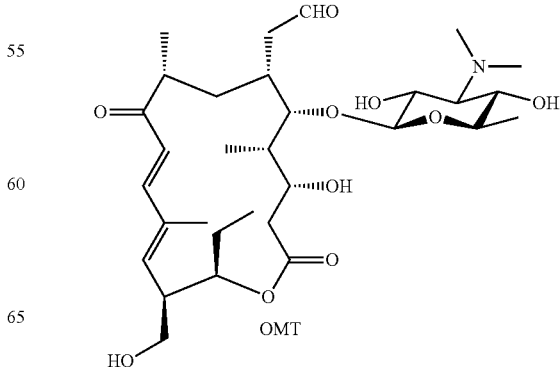

OMT with an amine of the general formula NR$^1$R$^2$ to form a compound of the following formula (IIb)

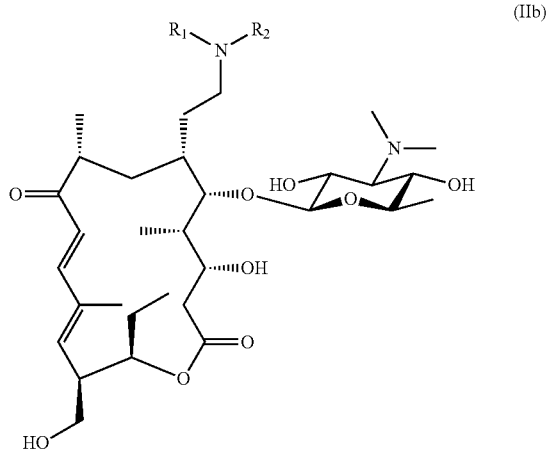

(IIb)

wherein
R$^1$ is as defined for R$^{11}$ and R$^{12}$ in the formula (IIa) above, and
R$^2$ is C1-C6-alkyl, bearing one N$_3$-substituent and being optionally substituted with one or more substituents selected from the group consisting of halogen, aryl, substituted aryl, heterocyclic and substituted heterocyclic; and (iv) reacting the resulting compound of the formula (IIb) with an R—C≡CH, wherein R is as defined for R$^{11}$ or R$^{12}$ in the formula (IIa) above, in the presence of a copper catalyst to form a compound of the formula (IIa).

The starting compound of the formula:

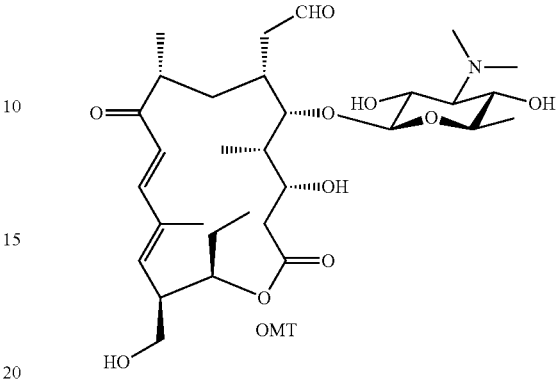

can be prepared by performing, for example following sub-steps:

(a) deglycosylation of tylosin under acidic condition, for example in the presence of TFA aq. or HBr; and (b) optionally converting the remaining functional groups to desired substituents according to any conventional process.

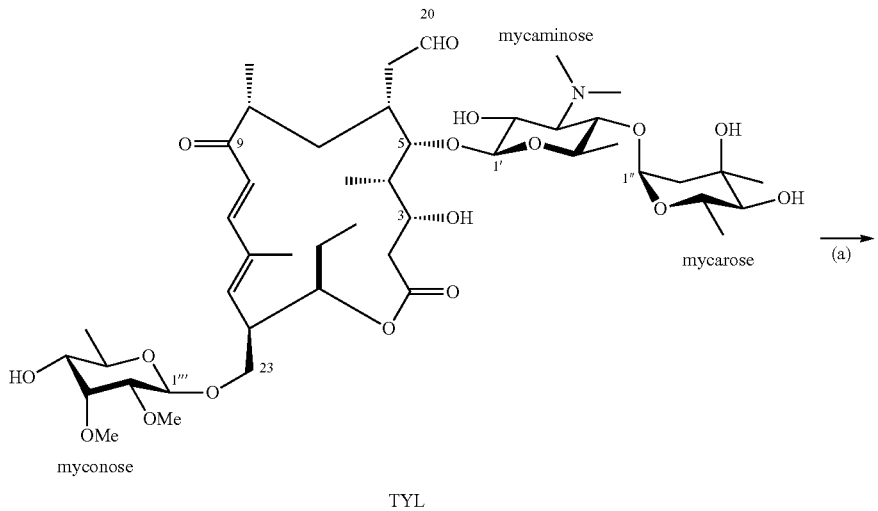

TYL

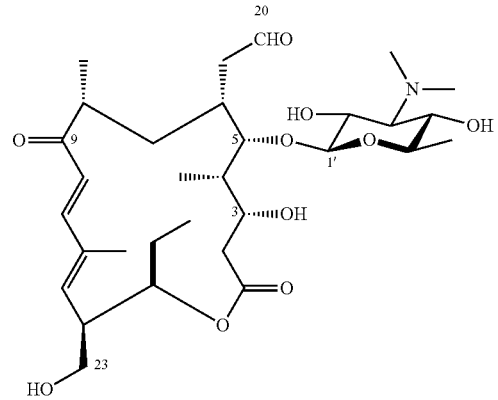

One example for a method for preparing a compound of the formula (I):

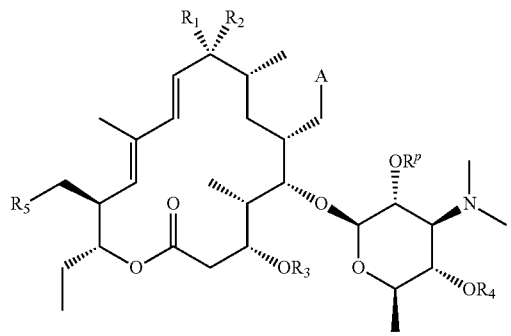

(I)

wherein A is CH$_2$—R' and R1, R2, R3, R4, R5, R' and R$^p$ are as defined above;

which method comprises following steps:

(i) reacting a compound of the formula (II):

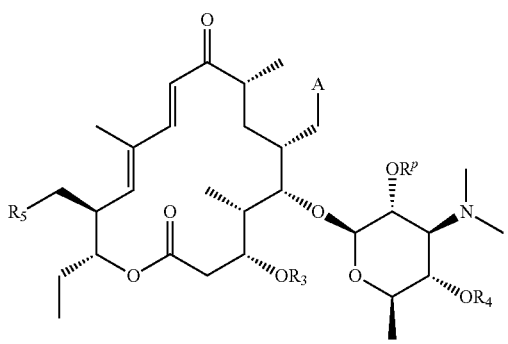

(II)

wherein,

A is CH$_2$-hydroxy; and the other variable groups are as defined in the formula (I), with an azide selected from diphenylphosphoryl azide (DPPA) or sodium azide (NaN$_3$) to form a compound of said formula (II) wherein A is CH$_2$—N$_3$ and the other variable groups are as defined in the formula (I); and (ii) reacting the resulting compound of the formula (II) wherein A is CH$_2$—N$_3$ and the other variable groups are as defined in the formula (I) with an R—C≡CH, wherein R is as defined in the formula (I) above, in the presence of a copper catalyst to form a compound of the formula (II), wherein A is CH$_2$—R' and R3, R4, R5, R' and R$^p$ are as defined above.

Further example, for a method for preparing a compound of the formula (I):

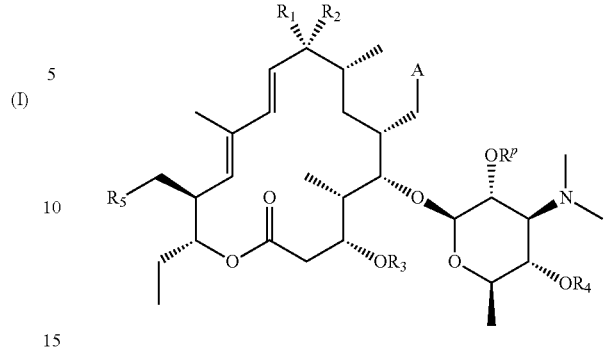

(I)

wherein R5 is R' and A, R1, R2, R3, R4, R' and R$^p$ are as defined above;

which method comprises following steps:

(i) reacting a compound of the formula (II):

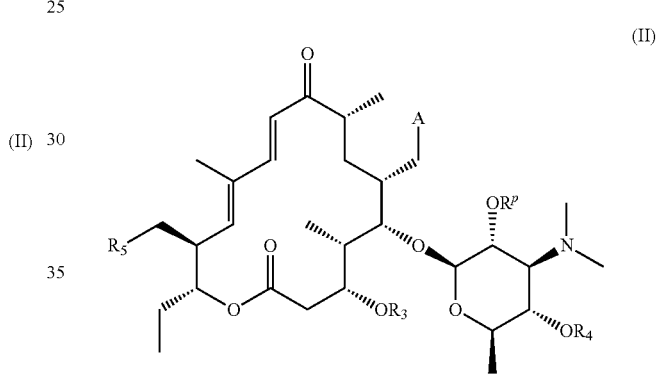

(II)

wherein,

R5 is hydroxy; and the other variable groups are as defined in the formula (I), with an azide selected from diphenylphosphoryl azide (DPPA) or sodium azide (NaN$_3$) to form a compound of said formula (II) wherein R5 is —N$_3$ and the other variable groups are as defined in the formula (I); and (ii) reacting the resulting compound of the formula (II) wherein R5 is —N$_3$ and the other variable groups are as defined in the formula (I) with an R—C≡CH, wherein R is as defined in the formula (I) above, in the presence of a copper catalyst to form a compound of the formula (II), wherein R5 is R' and A, R3, R4, R' and R$^p$ are as defined above.

In the step (i) of those methods for preparing the present compound of formula (I), the starting materials are commercially available or can be easily prepared a compound commercially available according to any know method. For example, the starting compound of the formula:

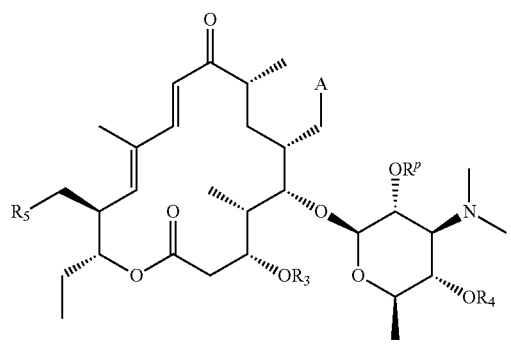

(II)

wherein,

A is CH$_2$-hydroxy; and the other variable groups are as defined in the formula (I), can be prepared by performing following sub-steps:

(a) deglycosylation of tylosin under acidic condition, for example in the presence of HCl aq.;

(b) reducing aldehyde group at 20-position in the presence of a reducing agent, such as NaBH$_4$; and (c) optionally converting the remaining functional groups to desired substituents according to any conventional process.

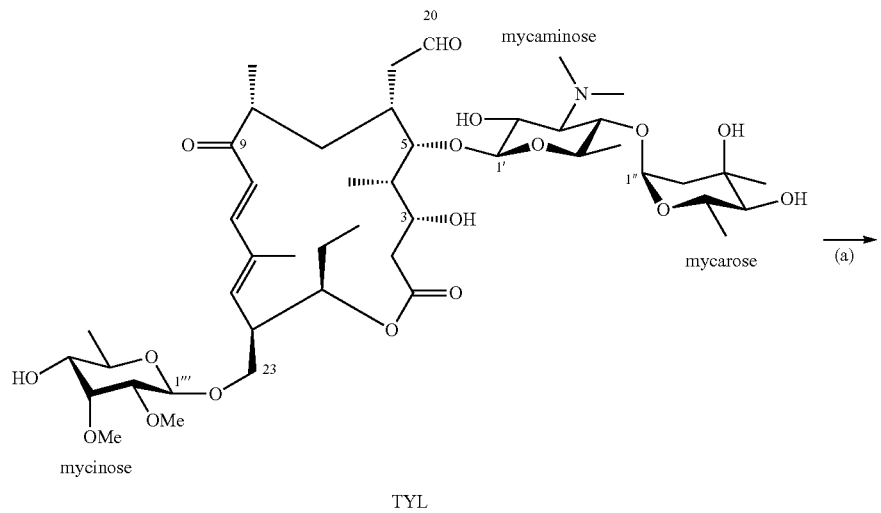

TYL

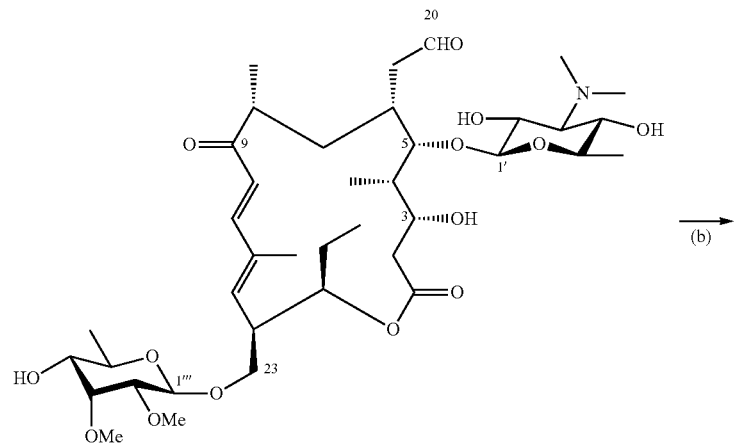

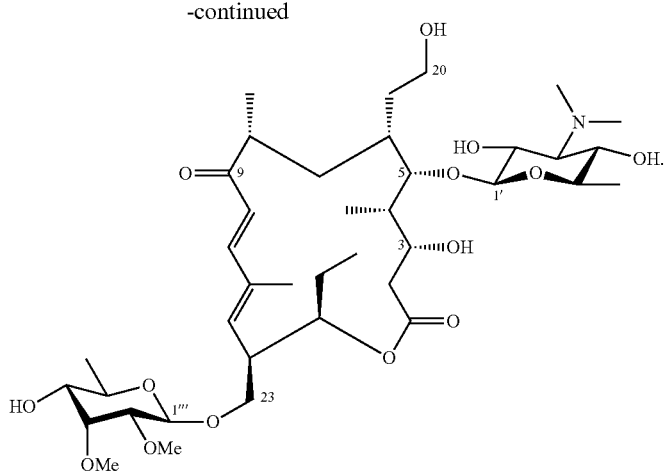

To enhance the reactivity of the 20- or 23-hydroxyl functional group, the starting compounds of formula (II) may, if desired, be halogenized, for example with a halogenating agent such as $I_2$ or $CCl_4$ in the presence of $PPh_3$ in a solvent such as pyridine and/or dichloromethyl at −27 to 40° C., preferably 0° C. to rt, so that a compound of formula (II) wherein A is $CH_2$-halo or R5 is halogen is formed.

By using a compound of formula (II) wherein either A is $CH_2$—R' or R5 is R', which compound may be obtained from any of the preparing methods described above as a starting material, 20,23-bistriazole tylosin derivative, that is a compound of the formula (I) wherein A is $CH_2$—R' and R5 is R' may be prepared by carrying out the other preparing method as described above.

In a detailed example for formula (I), the azidation of step (i) in the preparing methods above can be carried out by reacting azide such as diphenylphosphoryl azide (DPPA) or sodium azide ($NaN_3$) with the starting material in the presence of solvent such as THF or DMSO at −27 to 100° C., preferably at 0 to 80° C.

The reaction of step (ii) and (iv) in the preparing methods for formula (I) and (IIb) above can be carried out in a solvent for example water, tert-butyl alcohol, methanol or acetonitrile or combination thereof, preferably in acetonitrile, preferably in the presence of tris[(1-benzyl-1H-1,2,3-triazol-4-yl)methyl]amine (TBTA), in the presence of a copper catalysis for example $CuSO_4.5H_2O$, $CuOTf.C_6H_6$, [Cu$(NCCH_3)_4$][$PF_6$] or CuI, preferably CuI at 0 to 100° C., preferably 10 to 40° C., more preferably rt.

Still further example for a method for preparing a compound of the formula (I):

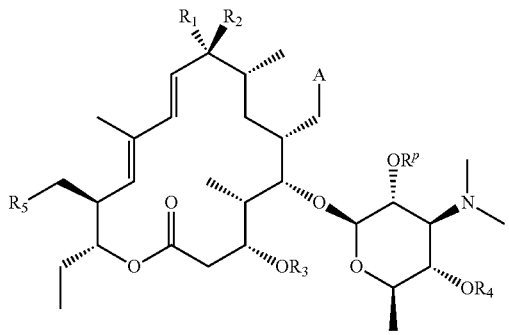

wherein R1 and R2 taken together are =N—O—C0-C3-alkyl-R' and A, R3, R4, R5, R' and $R^p$ are as defined above;
which method comprises following steps:
(i) reacting a compound of the formula (II):

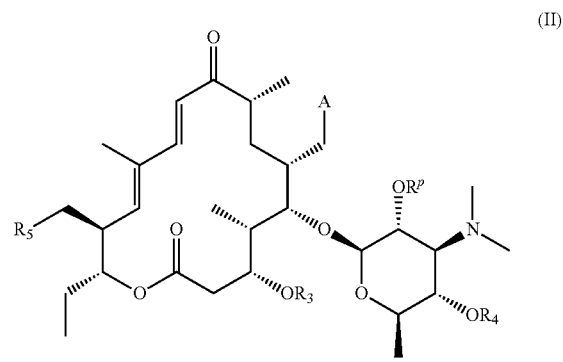

wherein,
the variable groups are as defined in the formula (I), but A is not —CHO, with a CH≡C—$(CH_2)_n$—O—$NH_2$.HCl wherein n is an integer from 1 to 3 to form a compound of the formula (III):

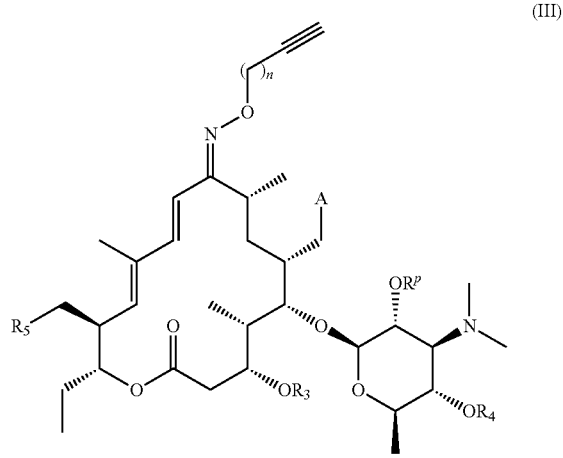

wherein n is an integer from 1 to 3 and A, R3, R4, R5 and R$^p$ are as defined in formula (I), provided that A is not —CHO; and (ii) reacting the compound of the formula (III) resulting from step (i) or (ii) with an R—N$_3$, wherein R is as defined in formula (I) above, in the presence of a copper catalyst to form a compound of the formula (I):

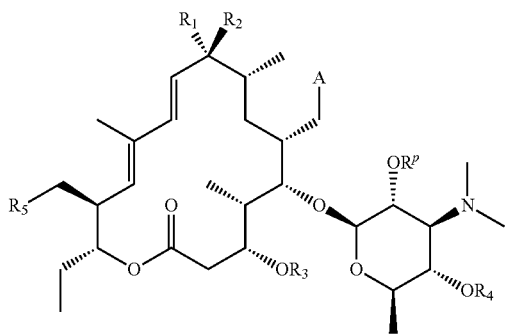
(I)

wherein R1 and R2 taken together are =N—O—C0-C3-alkyl-R' and A, R3, R4, R5, R' and R$^p$ are as defined above.

The starting compound of the formula (II):

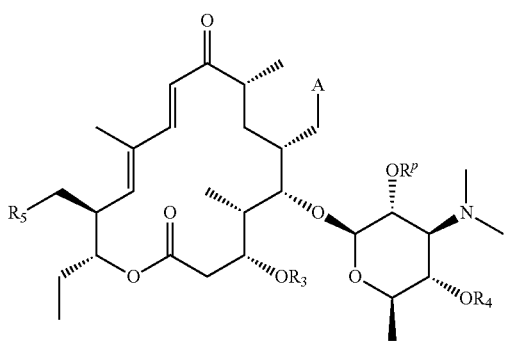
(II)

wherein, the variable groups are as defined in the formula (I), but A is not —CHO can be readily available or prepared according to any conventional process known to the skilled person.

In a detailed embodiment, the introduction of an acetylene moiety of step (i) can be carried out by reacting a CH≡C—(CH$_2$)n-O—NH$_2$.HCl (wherein n is as defined above) with the starting material in a solvent such as pyridine or methanol or combination thereof, preferably in the combination of pyridine and methanol, at 0 to 80° C., preferably rt to 65° C. If desired, an oxo or hydroxyl group which is desired not to participate in the introduction of an acetylene moiety can be protected by any conventional process.

In a detailed example, the reaction of step (ii) and (iv) for formula (I) and (IIb) can be carried out in solvent, for example water, tert-butyl alcohol, methanol or acetonitrile or combination thereof, preferably in acetonitrile, preferably in the presence of tris[(1-benzyl-1H-1,2,3-triazol-4-yl)methyl]amine (TBTA), in the presence of copper catalyst, for example CuSO$_4$.5H$_2$O, CuOTf.C$_6$H$_6$, [Cu(NCCH$_3$)$_4$][PF$_6$] or CuI, preferably CuI at 0 to 100° C., preferably 10 to 40° C., more preferably rt.

The compounds represented by R—N$_3$ and R—C≡CH are commercially available or can be easily prepared by any conventional procedure known to a skilled person.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the H$^+$ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide and Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Intermediates and final products can be worked up and/or purified according to standard methods, e.g., using chromatographic methods, distribution methods, (re-) crystallization, and the like. The compounds, including their salts, may also be obtained in the form of solvates, in particular hydrates. In the context of the invention, solvates refer to those forms of the compounds according to the invention which, in the solid or liquid state, form a complex by coordination with solvent molecules. Hydrates are a specific form of the solvates in which the coordination is with water. Crystals of the present compounds may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

This invention also encompasses pharmaceutical or veterinary compositions containing, and methods of treating bacterial infections through administering, pharmaceutically acceptable prodrugs of the compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently bound through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed.

For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10.

Free amines can also be derivatized as amides, sulfonamides or phosphonamides. All of these prodrug moieties may incorporate groups including but not limited to ether, amine and carboxylic acid functionalities.

The compounds of the present invention have valuable pharmacological properties and thus they can be used for the treatment of diseases. In one embodiment, the compound of the present invention may be used for the treatment or prevention of bacterial infections or disorders associated with bacterial infections in animals, for example mammals, fish or birds.

The term "animal", "patient" or "subject" as used herein is used interchangeably. The term animal typically includes, but is not limited to animals suffering from, at risk of suffering from, or potentially capable of suffering from a bacterial infection, for example humans, cattle, horses, chickens, pigs, sheep, goats, dogs, apes, cats, mice, rabbits, rats, etc.; especially farm animals such as cattle, pigs and poultry.

As used herein, the term "bacterial infection(s)" includes, but is not limited to, bacterial infections that occur in mammals, fish and birds as well as disorders related to bacterial infections that may be treated or prevented by administering antibiotics such as the compounds of the present invention. The compounds of the present invention are useful for treating infections caused by bacteria such as:

*Staphylococcus* spp, *Streptococcus* spp, *Enterococcus* spp, *Neisseria* spp, *Moraxella* spp, *Corynebacterium* spp, *Lactobacillus* spp, *Bacillus* spp, *Listeria* spp, *Erysipelothrix* spp, *Arcanobacterium* spp, *Vibrio* spp *Aeromonas* spp, *Escherichia* spp, *Klebsiella* spp, *Proteus* spp, *Salmonella* spp, *Shigella* spp, *Morganella* spp, *Citrobacter* spp, *Enterobacter* spp, *Serratia* spp, *Erwinia* spp, *Yersinia* spp, *Pseudomonas* spp, *Alcaligenes* spp, *Burkholderia* spp, *Phyllobacterium* spp, *Acinetobacter* spp, *Stenotrophomonas* spp, *Haemophilus* spp, *Actinobacillus* spp, *Bordetella* spp, *Pasteurella* spp, *Brucella* spp, *Campylobacter* spp, *Capnytophaga* spp, *Francisella* spp, *Helicobacter* spp, *Legionella* spp, *Mycoplasma* spp, *Ureaplasma* spp, *Bartonella* spp, *Chlamydia* spp, *Coxiella* spp, *Ehrlichia* spp, *Rickettsia* spp, *Borrelia* spp, *Leptospira* spp, *Treponema* spp, *Brachyspira* spp, *Veillonella* spp, *Peptostreptococcus* spp, *Peptococcus* spp, *Bacteroides* spp, *Porphyromonas* spp, *Prevotella* spp, *Fusobacterium* spp, *Clostridium* spp, *Actinomyces* spp, *Propionibacterium* spp, *Eubacterium* spp, *Lactobacillus* spp, *Bifidobacterium* spp.

More specifically the present compounds can be used in the treatment or prevention of bacterial infections caused by gram-positive bacteria such as staphylococcal, streptococcal, *Lactobacillus acidophilus*, *Corynebacterium diphtheriae*, *Propionibacterium acnes*, *Actinomyces bovis*, *Myco-* bacterium tuberculosis, Mycobacterium leprae, Bacillus or Clostridium or gram-negative bacteria such as Pasteurella, Mannheimia or Mycoplasma infections in animals.

Such bacterial infections and disorders related to such infections include, but are not limited to, the following: acne, rosacea, skin infection, pneumonia, otitis media, sinusitus, bronchitis, tonsillitis, and mastoiditis related to infection by Streptococcus pneumoniae, Haemophilus influenzae, Moraxella catarrhalis, Staphylococcus aureus, Peptostreptococcus spp. or Pseudomonas spp.; pharynigitis, rheumatic fever, and glomerulonephritis related to infection by Streptococcus pyogenes, Groups C and G streptococci, Clostridium diptheriae, or Actinobacillus haemolyticum; respiratory tract infections related to infection by Mycoplasma pneumoniae, Legionella pneumophila, Streptococcus pneumoniae, Haemophilus influenzae, or Chlamydia pneumoniae; uncomplicated skin and soft tissue infections, abscesses and osteomyelitis, and puerperal fever related to infection by Staphylococcus aureus, coagulase-positive staphylococci (i.e., S. epidermidis, S. hemolyticus, etc.), S. pyogenes, S. agalactiae, Streptococcal groups C-F (minute-colony streptococci), viridans streptococci, Corynebacterium spp., Clostridium spp., or Bartonella henselae; uncomplicated acute urinary tract infections related to infection by S. saprophyticus or Enterococcus spp.; urethritis and cervicitis; sexually transmitted diseases related to infection by Chlamydia trachomatis, Haemophilus ducreyi, Treponema pallidum, Ureaplasma urealyticum, or Nesseria gonorrheae; toxin diseases related to infection by S. aureus (food poisoning and Toxic shock syndrome), or Groups A, S. and C streptococci; ulcers related to infection by Helicobacter pylori; systemic febrile syndromes related to infection by Borrelia recurrentis; Lyme disease related to infection by Borrelia burgdorferi; conjunctivitis, keratitis, and dacrocystitis related to infection by C. trachomatis, N. gonorrhoeae, S. aureus, S. pneumoniae, S. pyogenes, H. influenzae, or Listeria spp.; disseminated Mycobacterium avium complex (MAC) disease related to infection by Mycobacterium avium, or Mycobacterium intracellulare; gastroenteritis related to infection by Campylobacter jejuni; intestinal protozoa related to infection by Cryptosporidium spp., odontogenic infection related to infection by viridans streptococci; persistent cough related to infection by Bordetella pertussis; gas gangrene related to infection by Clostridium perfringens or Bacteroides spp.; Skin infection by S. aureus, Propionibacterium acne; atherosclerosis related to infection by Helicobacter pylori or Chlamydia pneumoniae; or the like.

Further bacterial infections and disorders related to such infections that may be treated or prevented in animals include, but are not limited to, the following: bovine respiratory disease related to infection by P. haemolytica., P. multocida, Mycoplasma bovis, or Bordetella spp.; cow enteric disease related to infection by E. coli or protozoa (i.e., coccidia, cryptosporidia, etc.), dairy cow mastitis related to infection by S. aureus, S. uberis, S. agalactiae, S. dysgalactiae, Klebsiella spp., Corynebacterium, or Enterococcus spp.; swine respiratory disease related to infection by A. pleuropneumoniae., P. multocida, or Mycoplasma spp.; swine enteric disease related to infection by E. coli, Lawsonia intracellularis, Salmonella spp., or Serpulina hyodyisinteriae; cow footrot related to infection by Fusobacterium spp.; cow metritis related to infection by E. coli; cow hairy warts related to infection by Fusobacterium necrophorum or Bacteroides nodosus; cow pink-eye related to infection by Moraxella bovis, cow premature abortion related to infection by protozoa (i.e., neosporium); urinary tract infection in dogs and cats related to infection by E. coli; skin and soft tissue infections in dogs and cats related to infection by S. epidermidis, S. intermedius, coagulase neg. Staphylococcus or P. multocida; dental or mouth infections in dogs and goats related to infection by Alcaligenes spp., Bacteroides spp., Clostridium spp., Enterobacter spp., Eubacterium spp., Peptostreptococcus spp., Porphfyromonas spp., Campylobacter spp., Actinomyces spp., Erysipelothrix spp., Rhodococcus spp., Trypanosoma spp., Plasmodium spp., Babesia spp., Toxoplasma spp., Pneumocystis spp., Leishmania spp., Trichomonas spp. or Prevotella spp. Other bacterial infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996). The compounds of the present invention is especially effective to respiratory diseases such as pasteurellosis caused by Gram negative bacillus such as Pasteurella or Mannheimia in farm animals such as cows.

Still further bacterial infections and disorders related to such infections that may be treated or prevented in animals especially by compounds of formula (IIa) as mentioned before include, but are not limited to, mastitis in all non-human milk-producing mammals, such as cattle, camel, buffalo, goat or sheep, and which may be associated with several pathogens including E. coli, Klebsiella spp., Enterobacter spp., Salmonella spp., Citrobacter spp., Serratia spp., Shigella spp., Edwardsiella spp., Hafnia spp., Morganella spp., Providencia spp., Yersinia spp., Staphylococcus aureus, Staphylococcus spp., Pseudomonas spp., Streptococcus agalactiae, Streptococcus dysgalactiae, Streptococcus spp., Enterococci, Corynebacterium spp., Arcanobacterium spp., Actinomyces spp., Mycobacterium spp., Prototheca spp., Mycoplasma spp., and Erwinia spp., among others and in addition to the above mentioned pathogens related to mastitis. Of the mentioned non-human milk-producing mammals, ruminants that are used for milk production for human consumption, such as cattle, buffalo, sheep, and goat, are especially important.

Accordingly, in a certain embodiment, the present invention provides a pharmaceutical or veterinary composition comprising any of the compounds of the present invention. The composition may comprise therapeutically effective amount of the compound of the present invention, and if desired one or more pharmaceutically acceptable excipients or carriers.

The language "therapeutically effective amount" of the compound is that amount necessary or sufficient to treat or prevent a bacterial infection, e.g. prevent the various morphological and somatic symptoms of a bacterial infection, and/or a disease or condition described herein. In an example, an effective amount of the compound of the invention is the amount sufficient to treat a bacterial infection in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of a bacterial infection. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

Compounds of the invention may be used in the treatment of states, disorders or diseases as described herein, or for the manufacture of pharmaceutical or veterinary compositions for use in the treatment of these diseases. Methods of use of compounds of the present invention in the treatment of these diseases, or pharmaceutical or veterinary preparations comprising compounds of the present invention for the treatment of these diseases are also included in embodiments of the present invention.

The language "pharmaceutical or veterinary composition" includes preparations suitable for administration to mammals, e.g., farm animals such as cows. When the compounds of the present invention are administered as pharmaceuticals to mammals, e.g., cows, they can be given per se or as a pharmaceutical or veterinary composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient.

Formulations of the present invention include those known in the art. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Methods of preparing these formulations or compositions are also known in the art.

The term "treat," "treated," "treating" or "treatment" includes the diminishment or alleviation of at least one symptom associated or caused by the state, disorder or disease being treated. In certain embodiments, the treatment comprises the induction of a bacterial infection, followed by the activation of the compound of the invention, which would in turn diminish or alleviate at least one symptom associated or caused by the bacterial infection being treated. For example, treatment can be diminishment of one or several symptoms of a disorder or complete eradication of a disorder.

Especially treatment of mastitis is curing or ameliorating an animal that has contracted mastitis, i.e. reducing at least one symptom of mastitis. Mastitis refers to inflammation of the mammary gland. Physical, chemical and usually bacteriological changes in the milk and pathological changes in the glandular tissue characterize it. The glandular changes often result in a number of symptomatic conditions such as, discoloration of the milk, the presence of clots and the presence of large numbers of leukocytes. Clinically, mastitis is seen as swelling, heat, pain and induration in the mammary gland often resulting in deformation of the udder. An inflamed udder can be visibly seen or determined through palpation of the udder. In many cases the diagnosis of subclinical infections has come to depend largely on indirect tests which depend on the leukocyte content of the milk (flakes, clots, or serous milk), at least 1 bacterium is detected in at least 100 µL of milk from the udder, elevated somatic cell count (SCC) usually higher than 300,000 cells/mL and/or the electrical conductivity of the milk is increased from normal. Prevention of mastitis means preventing the occurrence of the infection. Prevention also includes treatment of cows that do not exhibit any signs of mastitis but are in the presence of other cows that do have at least one sign of mastitis to minimize or prevent the transmission or potential transmission of mastitis from one cow to another.

These compounds may be administered to humans and other animals for therapy by any suitable route of administration.

Regardless of the route of administration selected, the compounds of the present invention, which may be used in a suitable hydrated form, and/or the pharmaceutical or veterinary compositions of the present invention, are formulated into pharmaceutically acceptable dosage forms by conventional methods known to those of skill in the art.

Actual dosage levels of the active ingredients in the pharmaceutical or veterinary compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical or veterinary composition required. For example, the physician or veterinarian could start doses of the compounds of the invention employed in the pharmaceutical or veterinary composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 1.0 to about 100 mg per kg per day. An effective amount is that amount treats a bacterial infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical or veterinary composition.

The antibacterial activity by the compounds of the present invention may be measured using a number of assays available in the art. An example of such an assay is the standard minimum inhibitory concentration (MIC) test conducted according to CSLI guidelines or paper disc test conducted according to Examples below.

Further disclosed are embodiments of compounds represented by the formula (I):

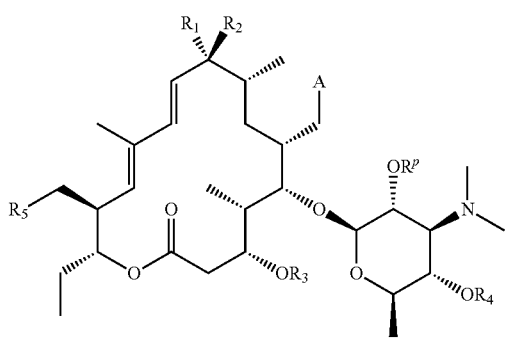

(I)

or a pharmaceutically acceptable salt, ester, prodrug or solvate thereof;
wherein, A is selected from the group consisting of:
(1) —CHO or a protected aldehyde;
(2) CH$_2$—X, wherein X is selected from the group consisting of:
  a. hydroxy or protected hydroxy;
  b. halogen; and
  c. —N$_3$
(3) —CN;
(4) —CH=N—NR7R8, wherein R7 and R8 are each independently selected from hydrogen, C1-C6-alkyl, optionally substituted with one or more substituents selected from the group consisting of halogen, aryl, substituted aryl, heterocyclic and substituted heterocyclic, C2-C6-alkenyl, optionally substituted with one or more substituents selected from the group consisting of halogen, aryl, substituted aryl, heterocyclic and substituted heterocyclic, C2-C6-alkynyl, optionally substituted with one or more substituents selected from the group consisting of halogen, aryl, substituted aryl, heterocyclic and substituted heterocyclic or R7 and R8 taken with the nitrogen atom to which they are connected form a 3- to 7-membered ring which may optionally contain a hetero function selected from the group consisting of —O—, —NH—, —N(C1-C6-alkyl)-, —N(aryl)-, —N(heteroaryl)-, —S—, —S(O)— and —S(O)$_2$—;
(5) —CH=N—OR7, wherein R7 is as previously defined;
(6) C3-C14-cycloalkyl;
(7) substituted C3-C14-cycloalkyl;
(8) aryl;
(9) substituted aryl;
(10) heterocyclic;
(11) substituted heterocyclic;
(12) CH$_2$—R'; and
(13) —CH$_2$—NR7R8, where R7 and R8 are as previously defined;
R1 and R2 are each independently selected from the group consisting of:
(1) hydrogen;
(2) hydroxy;
(3) protected hydroxy;
(4) —OC(O)—C1-C12-alkyl, optionally substituted with one or more substituents selected from the group consisting of halogen, aryl, substituted aryl, heterocyclic, substituted heterocyclic, —O—R7 and —NR7R8 where R7 and R8 are as previously defined;
(5) —O—R7, where R7 is as previously defined;
(6) halogen;
(7) —NR7R8, where R7 and R8 are as previously defined;
(8) R1 and R2 taken together are oxo; and
(9) R1 and R2 taken together are =N—O—C0-C3-alkyl-R';
R3 is selected from the group consisting of:
(1) hydrogen;
(2) a hydroxy protecting group;
(3) —C(O)—C1-C12-alkyl, optionally substituted with one or more substituents selected from the group consisting of halogen, aryl, substituted aryl, heterocyclic, substituted heterocyclic, —O—R7 and —NR7R8 where R7 and R8 are as previously defined;
(4) C1-C6-alkyl, optionally substituted with one or more substituents selected from the group consisting of halogen, aryl, substituted aryl, heterocyclic, substituted heterocyclic, —O—R7 and —NR7R8 where R7 and R8 are as previously defined;
(5) C2-C6-alkenyl, optionally substituted with one or more substituents selected from the group consisting of halogen, aryl, substituted aryl, heterocyclic, substituted heterocyclic, —O—R7 and —NR7R8 where R7 and R8 are as previously defined; and
(6) C2-C6-alkynyl, optionally substituted with one or more substitutents selected from the group consisting of halogen, aryl, substituted aryl, heterocyclic, substituted heterocyclic, —O—R7 and —NR7R8 where R7 and R8 are as previously defined;
R4 is -M-Y, where M is:
(1) absent,
(2) —C(O)—,
(3) —C(O)N(R7)-, where R7 is as previously defined,
(4) —C1-C6-alkyl-N(R7)-, where R7 is as previously defined,
(5) —C2-C6-allcenyl-N(R7)-, where R7 is as previously defined, or
(6) —C2-C6-alkynyl-N(R7)-, where R7 is as previously defined;
and where Y is:
(1) hydrogen,
(2) hydroxy protecting group,
(3) C1-C6-alkyl, optionally substituted with one or more substituents selected from the group consisting of halogen, aryl, substituted aryl, heterocyclic and substituted heterocyclic, —OR7 where R7 is as previously defined,
(4) C2-C6-alkenyl, optionally substituted with one or more substituents selected from the group consisting of halogen, aryl, substituted aryl, heterocyclic and substituted heterocyclic, —OR7 where R7 is as previously defined,
(5) C2-C6-alkynyl, optionally substituted with one or more substituents selected from the group consisting of halogen, aryl, substituted aryl, heterocyclic and substituted heterocyclic, —OR7 where R7 is as previously defined,
(6) aryl,
(7) substituted aryl,
(8) heterocyclic, or
(9) substituted heterocyclic;
R5 is selected from the group consisting of:
(1) hydrogen;
(2) hydroxy;

(3) protected hydroxy;
(4) halogen;
(5) —O—R7, where R7 is as previously defined;
(6) —N$_3$ or R';
R$^P$ is hydrogen or a hydroxy protecting group;
and each R' is independently [1,4]-epi-[1,2,3]-triazoro-R; and where each R is independently selected from the group consisting of:
(1) C1-C9-alkyl, optionally substituted with one or more substituents selected from the group consisting of halogen, aryl, substituted aryl, heterocyclic and substituted heterocyclic, —OR7 where R7 is as previously defined;
(2) C2-C9-alkenyl, optionally substituted with one or more substituents selected from the group consisting of halogen, aryl, substituted aryl, heterocyclic and substituted heterocyclic, —OR7 where R7 is as previously defined;
(3) C2-C9-alkynyl, optionally substituted with one or more substituents selected from the group consisting of halogen, aryl, substituted aryl, heterocyclic and substituted heterocyclic, —OR7 where R7 is as previously defined;
(4) C3-C14-cycloalkyl;
(5) substituted C3-C14-cycloalkyl;
(6) aryl;
(7) substituted aryl;
(8) heterocyclic;
(9) substituted heterocyclic; and
(10) —COOR7, where R7 is as previously defined;
provided that at least one of A, R1 and R2 and R5 comprise R'.

Furthermore, compounds of said formula (I) are disclosed, wherein;
A is selected from halogen, CH$_2$—N$_3$, hydroxy, CHO, hydroxyC$_{1-6}$ alkyl, haloC$_{1-6}$ alkyl, methyl(3,5-di(C1-C3-alkyl)-piperidino), CH$_2$—R', and —CH$_2$—NR7R8;
R1 and R2 taken together are oxo or =N—O—C0-C3-alkyl-R';
R3 is H;
R4 is H;
R5 is selected from hydroxy, N$_3$, halogen, 6-deoxy-2,3-di-O-methyl-b-d-allo-hexapyranosyloxy and R'; and
R' is as defined above;
provided that at least one of A, R1 and R2 and R5 comprises R';
or a pharmaceutically acceptable salt, ester, prodrug or solvate thereof.

Furthermore, compounds of said formula (I) are disclosed, wherein;
A is CH$_2$—R' or —CH$_2$—NR7R8;
R1 and R2 taken together are oxo;
R3 is H;
R4 is H; and
R5 is 6-deoxy-2,3-di-O-methyl-b-d-allo-hexapyranosyloxy.

Furthermore, compounds of said formula (I) are disclosed, wherein;
A is CHO or methyl(3,5-dimethylpiperidino) or —CH$_2$NR7R8;
R1 and R2 taken together are oxo;
R3 is H;
R4 is H; and
R5 is R'.

Furthermore, compounds of said formula (I) are disclosed, wherein;
A is —CH$_2$—NR7R8;
R1 and R2 taken together are oxo;
R3 is H;
R4 is H; and
R5 is hydroxy.

Furthermore, compounds of said formula (I) are disclosed, wherein;
A is CHO, methyl(3,5-dimethylpiperidino), or —CH$_2$—NR7R8;
R1 and R2 taken together are =N—O—C0-C3-alkyl-R'; and
R3 is H;
R4 is H; and
R5 is 6-deoxy-2,3-di-O-methyl-b-d-allo-hexapyranosyloxy.

In the mentioned disclosure of compounds according to formula (I), R is preferably selected from the group consisting of

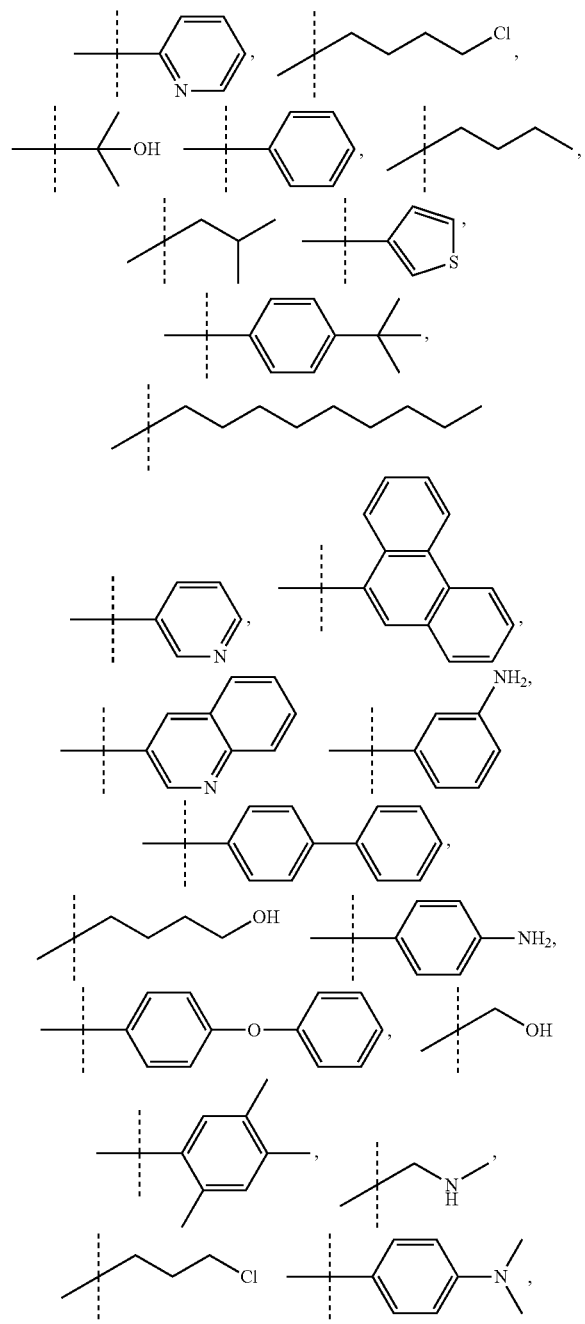

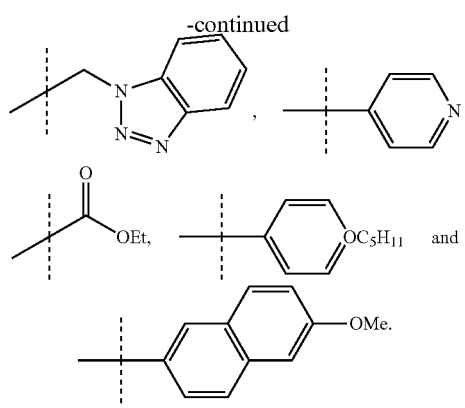

Further disclosed is a method for preparing a compound of the formula (I):

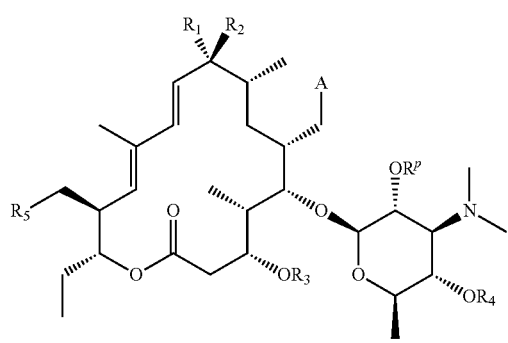

wherein A is CH$_2$—R' and R1, R2, R3, R4, R5, R' and R$^p$ are as defined above;
which method comprises following steps:
(i) reacting a compound of the formula (II):

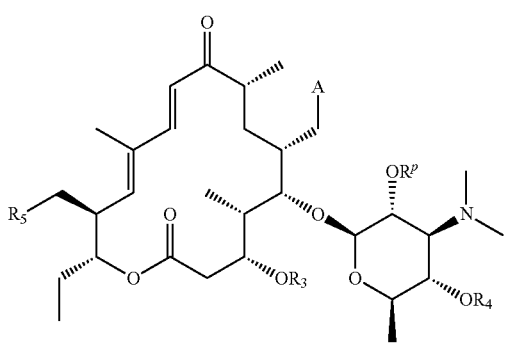

wherein,
A is CH$_2$-hydroxy; and
the other variable groups are as defined in the formula (I), with an azide selected from diphenylphosphoryl azide (DPPA) or sodium azide (NaN$_3$) to form a compound of said formula (II) wherein A is CH$_2$—N$_3$ and the other variable groups are as defined in the formula (I); and
(ii) reacting the resulting compound of the formula (II) wherein A is CH$_2$—N$_3$ and the other variable groups are as defined in the formula (I) with an R—C≡CH, wherein R is as defined in the formula (I) above, in the presence of a copper catalyst to form a compound of the formula (II), wherein A is CH$_2$—R' and R3, R4, R5, R' and R$^p$ are as defined above.

Furthermore, a method for preparing a compound of the formula (I) is disclosed:

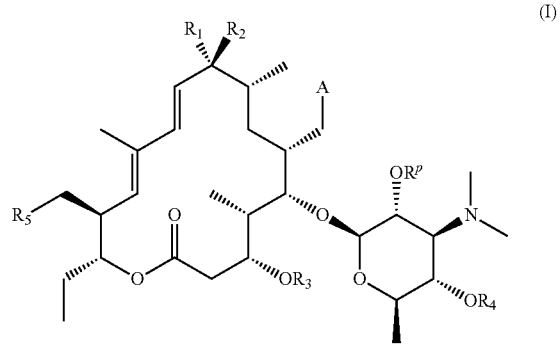

wherein R5 is R' and A, R1, R2, R3, R4, R' and R$^p$ are as defined above;
which method comprises following steps:
(i) reacting a compound of the formula (II):

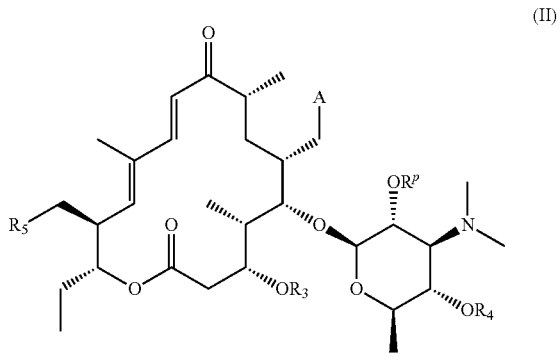

wherein,
R5 is hydroxy; and
the other variable groups are as defined in the formula (I), with an azide selected from diphenylphosphoryl azide (DPPA) or sodium azide (NaN$_3$) to form a compound of said formula (II) wherein R5 is —N$_3$ and the other variable groups are as defined in the formula (I); and
(ii) reacting the resulting compound of the formula (II) wherein R5 is —N$_3$ and the other variable groups are as defined in the formula (I) with an R—C≡CH, wherein R is as defined in the formula (I) above, in the presence of a copper catalyst to form a compound of the formula (II), wherein R5 is R' and A, R3, R4, R' and R$^p$ are as defined above.

Furthermore, a method for preparing a compound of the formula (I) is disclosed:

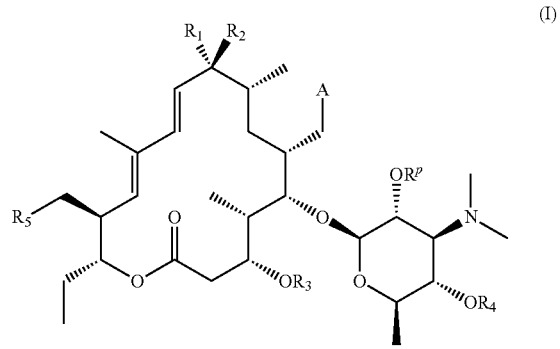

wherein R1 and R2 taken together are =N—O—C0-C3-alkyl-R' and A, R3, R4, R5, R' and R$^p$ are as defined above;

which method comprises following steps:

(i) reacting a compound of the formula (II):

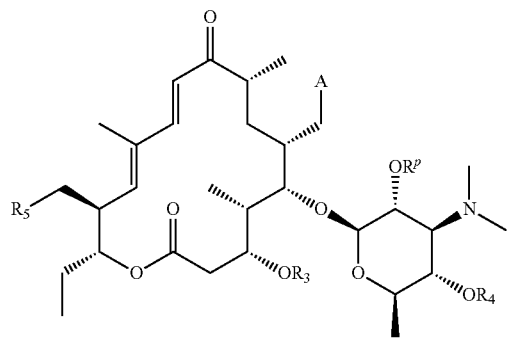

(II)

wherein, the variable groups are as defined in the formula (I), but A is not —CHO, with a CH≡C—(CH$_2$)$_n$—O—NH$_2$.HCl wherein n is an integer from 1 to 3 to form a compound of the formula (III):

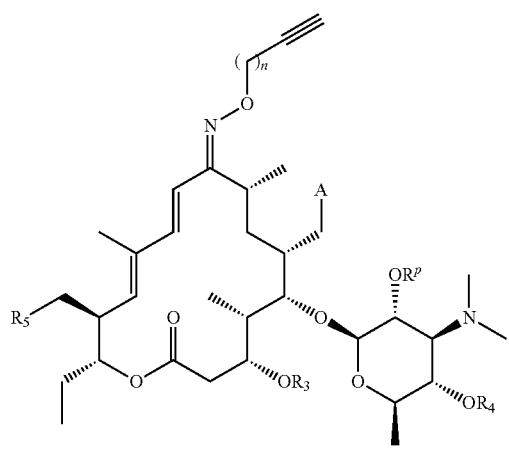

(III)

wherein n is an integer from 1 to 3 and A, R3, R4, R5 and R$^p$ are as defined in formula (I), but A is not —CHO; and (ii) reacting the compound of the formula (III) resulting from step (i) or (ii) with an R—N$_3$, wherein R is as defined in formula (I) above, in the presence of a copper catalyst to form a compound of the formula (I):

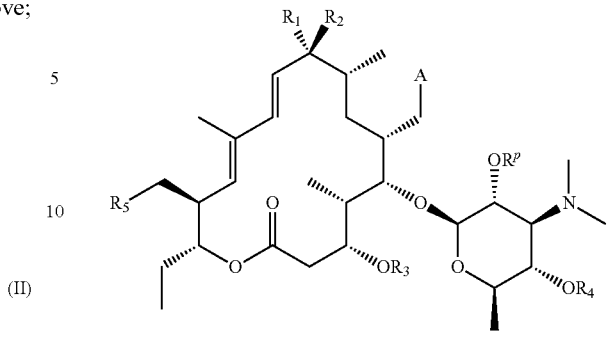

(I)

wherein R1 and R2 taken together are =N—O—C0-C3-alkyl-R' and A, R3, R4, R5, R' and R$^p$ are as defined above.

The invention is further illustrated by the following examples, which should not be construed as further limiting. The practice of the present invention will employ, unless otherwise indicated, conventional techniques of cell biology, cell culture, molecular biology, transgenic biology, microbiology and immunology, which are within the skill of the art.

EXAMPLES

All starting materials, building blocks, reagents, acids, bases, solvents, and catalysts, etc. utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21).

Analytical Methods

Infrared (IR) absorption spectra were determined by using Horiba FT-210 spectrometer.

$^1$H NMR spectra were determined by using JEOL JNM-EX270 (270 MHz), VALIAN-400 NMR System (400 MHz). $^{13}$C NMR spectra were determined by using JEOL JNM-EX270 (67.5 MHz), VARIAN-400 NMR system (100 MHz). Chemical shifts are indicated in δ (ppm) and coupling patterns are indicated by using following abbreviations: s: singlet; d: double; dd: double doublet; t: triplet; q: quartet; m: multiplet; br.d: broad doublet; br.dd: broad double doublet; br.dt: broad double triplet.

Low-resolution mass spectra (LC-MS) were determined by using JEOL JMS-DX300 Mass Spectrometer. High-resolution mass spectra (HRMS) were determined by using JEOL JMS-700 V Mass Spectrometer.

A thin-layer chromatography (TLC) was performed by using silica gel 60 F$_{254}$ (Merck) and compounds were detected by using UV irradiation (254 nm) or color development of phosphomolybden.

Column chromatography was performed by flash chromatography on silica gel 60 (Art. 1.09385) (Mark).

Thirty % of ammonium purchased from Kanto Chemical Co. Ltd. was used as NH$_4$OH Preparation of Compounds of Formula (I)

Preparation of 20-triazole-20-deoxodesmycosins (1) Preparation of Desmycosin (YT6)

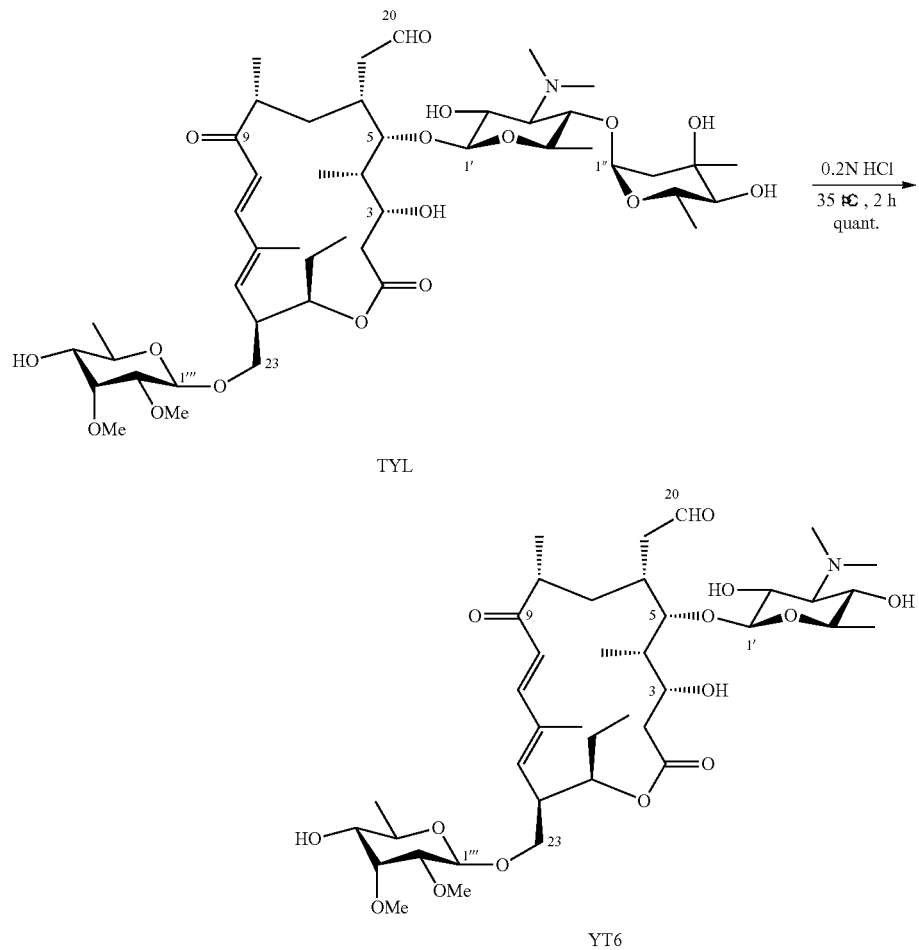

Tylosin (20.0 g, 21.8 mmol) was dissolved in 0.2N HCl aq. (340 mL) and then the mixture was stirred at 35° C. for 2 hours. After confirming complete consumption of the starting material, the reaction mixture was neutralized by adding 1N NaOH aq., extracted with $CHCl_3$ and dried over $Na_2SO_4$. The solvent was removed under reduced-pressure to obtain quantitative amount of desmycosin (YT6).

(2) Preparation of 20-dihydrodesmycosin (YT7)

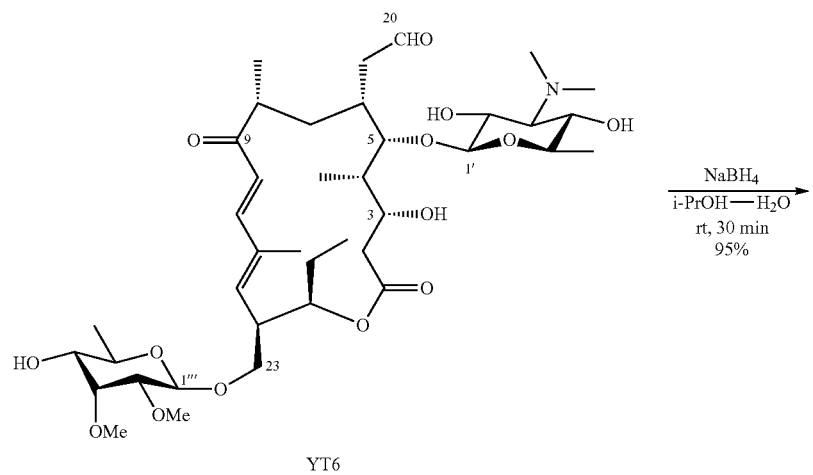

-continued

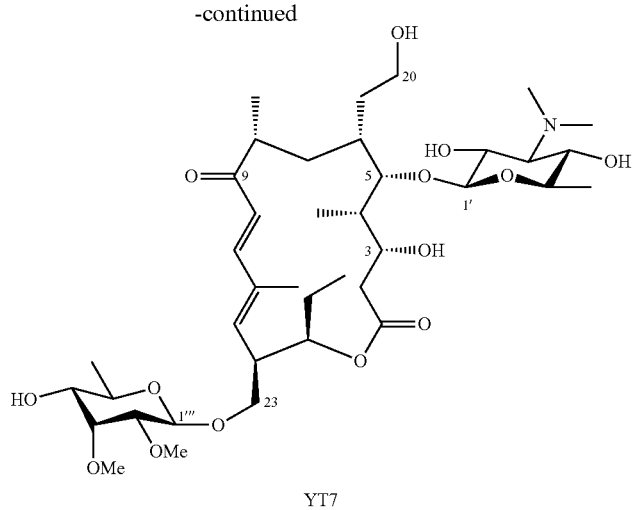
YT7

To a solution of Desmycosin (16.8 g, 21.8 mmol) in i-PrOH:H₂O=3:2 (300 mL) was added NaBH₄ (0.206 g, 5.45 mmol) and then the mixture was stirred at rt for 30 minutes. The reaction mixture was concentrated, neutralized by adding sat. NaHCO₃ aq., extracted with CHCl₃ and dried over Na₂SO₄. The solvent was removed under reduced pressure to obtain YT7 (Yield: 95%).

(3) Preparation of 20-chloro-20-deoxodesmycosin (YT8)

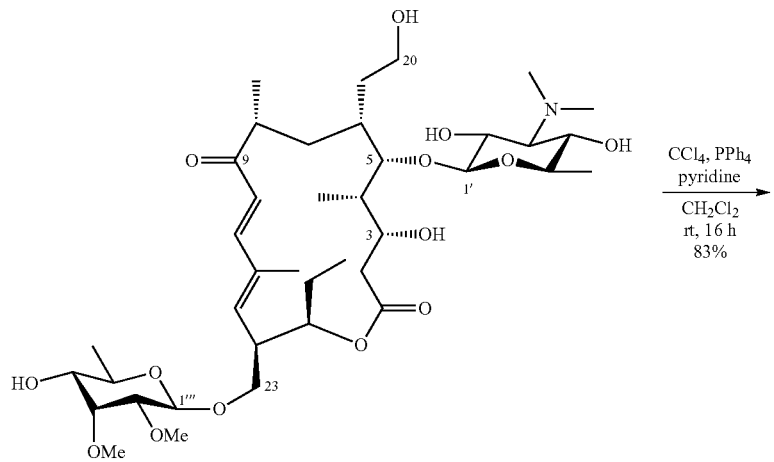
YT7

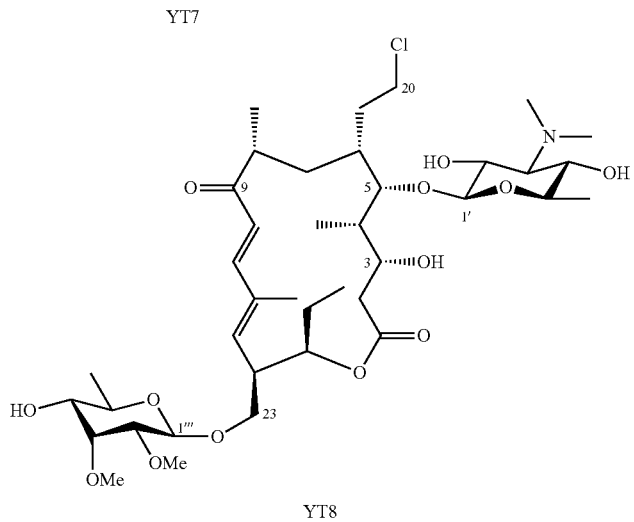
YT8

To a solution of YT7 (16.9 g, 21.8 mmol) in CH$_2$Cl$_2$:pyridine=1:1 (330 mL) were added PPh$_3$ (17.2 g, 65.4 mmol) and CCl$_4$ (3.2 g, 32.7 mmol) under N$_2$ atmosphere and the mixture was stirred for 16 hours at rt. The reaction mixture was diluted with CHCl$_3$, washed sequentially with sat. NaHCO$_3$ aq., brine. The organic layer was dried over Na$_2$SO$_4$ and then the solvent was removed under reduced pressure. The resulting products were purified by flash column chromatography to obtain YT8 (Yield: 83%).

(4) Preparation of 20-azido-20-deoxodesmycosin (YT11)

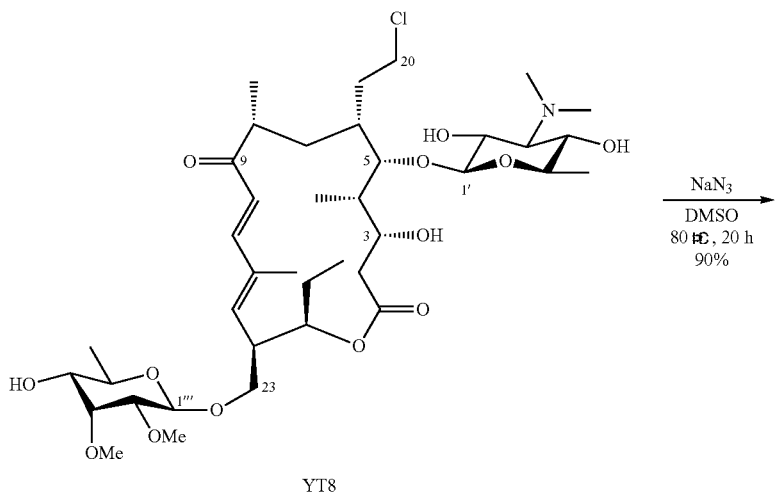

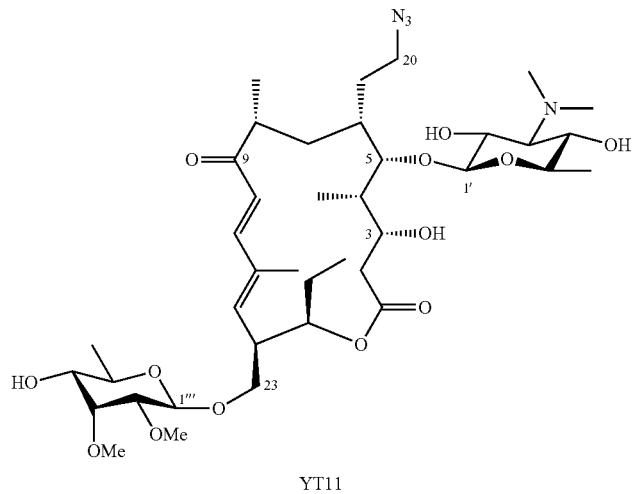

To a solution of YT8 (12.4 g, 15.7 mmol) in DMSO (160 mL, 0.100 M) was added NaN$_3$ (5.10 g, 78.3 mmol) and then the mixture was stirred for 20 hours at 80° C. The reaction mixture was diluted with AcOEt and water. The organic layer was separated, the aqueous layer was extracted with AcOEt and the combined organic layer was washed with water, brine, and then dried over Na$_2$SO$_4$ and concentrated. The resulting products were purified by flash column chromatography to obtain YT11 (Yield: 90%).

(5) Preparation of 20-triazole-20-deoxodesmycosins

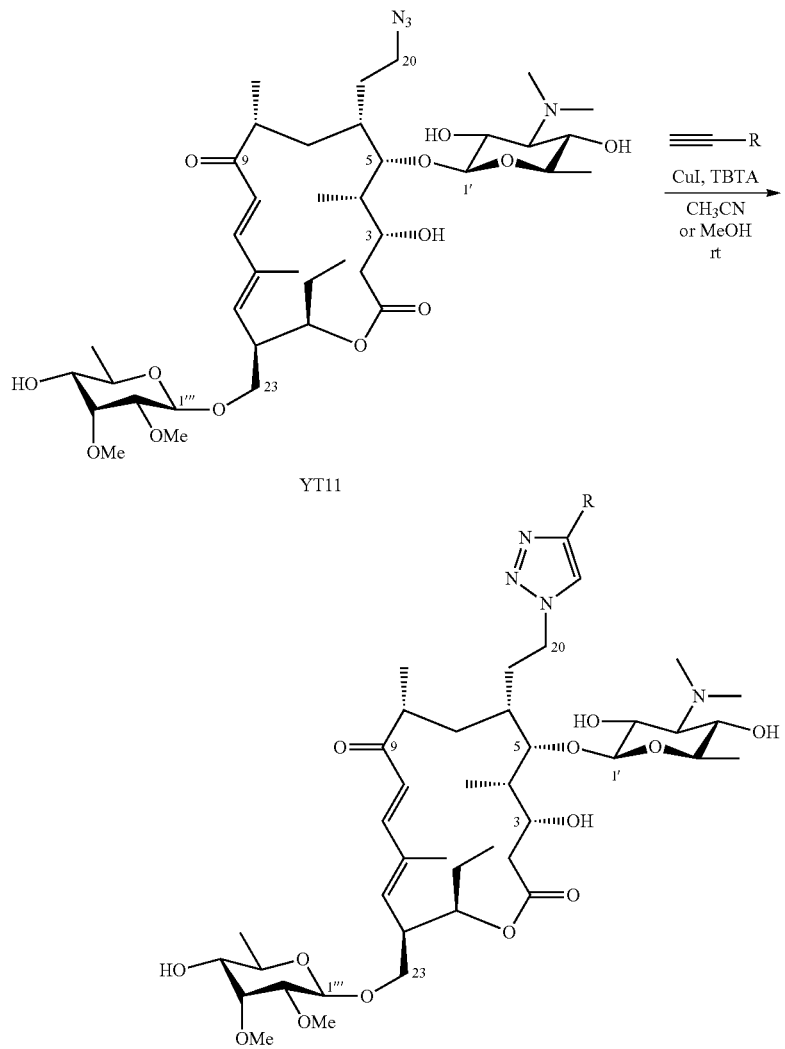

To a solution of YT11 (0.24 g, 0.30 mmol) in $CH_3CN$ or MeOH (3.0 mL) were added copper catalyst (2.9 mg, 0.015 mmol), TBTA (1.6 mg, 3.0 μmol) or 2,6-lutidine (0.01 eq.) and acetylene compound wherein R is p-ethynyl(pentyloxy)benzene or phenyl (0.33 mmol) and the mixture was stirred at rt until the reaction was completed. After completion, the reaction mixture was diluted with $CHCl_3$, washed with 10% $NH_3$ aq. After removing copper catalyst, the filtrate was washed with brine. The organic layer was dried over $Na_2SO_4$ and concentrated. The resulting products were purified by flash column chromatography to obtain the triazole compounds.

The results of the step (5) are shown in Table 1 below.

TABLE 1

| | | | Reaction times* | |
|---|---|---|---|---|
| Entry | Conditions | Solvents (0.1M) | R = p-ethynyl (pentyloxy) benzene | R = Ph |
| 1 | CuI (0.05 eq.) 2,6-lutidine (0.01 eq.), rt | $CH_3CN$ | 2 days | 2 days |
| 2 | $Cu(CH_3CN)_4PF_6$ (0.05 eq.) TBTA (0.01 eq.), rt | MeOH | 2 days | 2 days |
| 3 | $Cu(CH_3CN)_4PF_6$ (0.05 eq.) TBTA (0.01 eq.), rt | $CH_3CN$ | 30 min | 30 min |
| 4 | CuI (0.05 eq.) TBTA (0.01 eq.), rt | MeOH | 50 min | 120 min |
| 5 | CuI (0.05 eq.) TBTA (0.01 eq.), rt | $CH_3CN$ | 90 min | 120 min |

*Time for consumption of the starting material.

Under the conditions of Entry 4 or 5 above, with the following nineteen compounds:

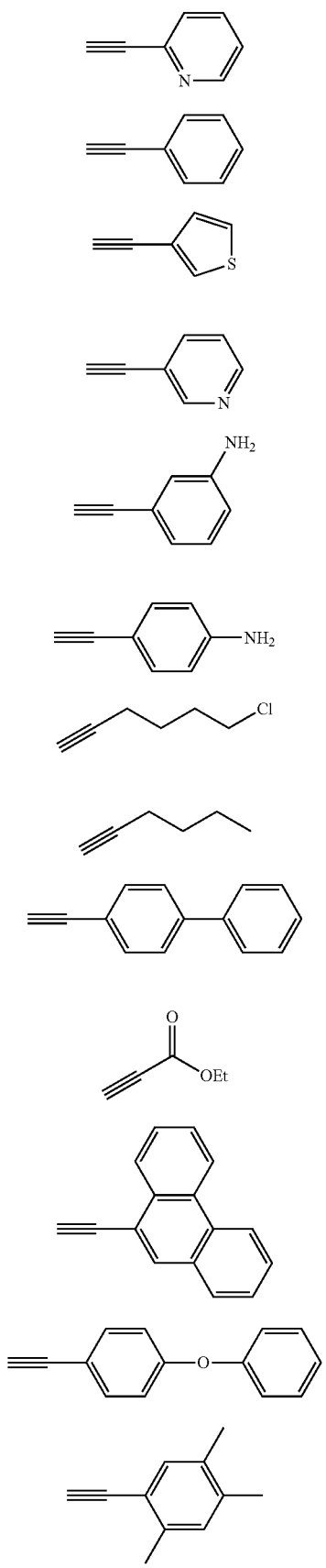
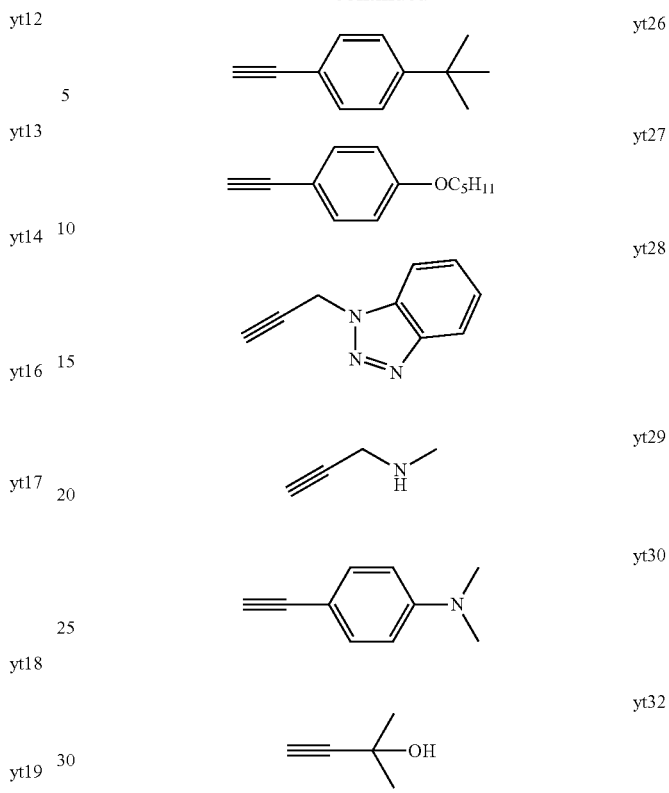
as the acetylene compound, the step (5) above was repeated to obtain the 20-triazole-20-deoxodesmycosins, which are shown below.
20-(4-(pyridine-2-yl)-1H-1,2,3-triazol-1-yl)-20-deoxodesmycosin (YT12)
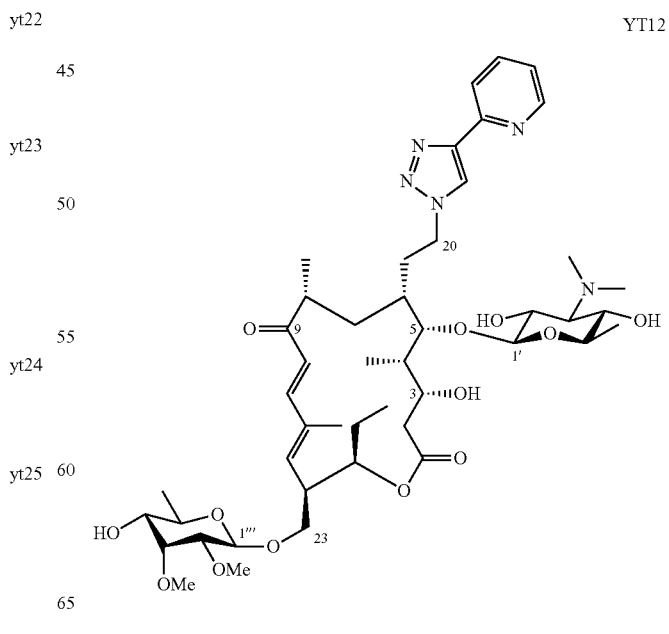
Yield: 85%

49
20-(4-phenyl-1H-1,2,3-triazol-1-yl)-20-deoxodesmycosin (YT13)
50
20-(4-(pyridine-3-yl)-1H-1,2,3-triazol-1-yl)-20-deoxodesmycosin (YT16)
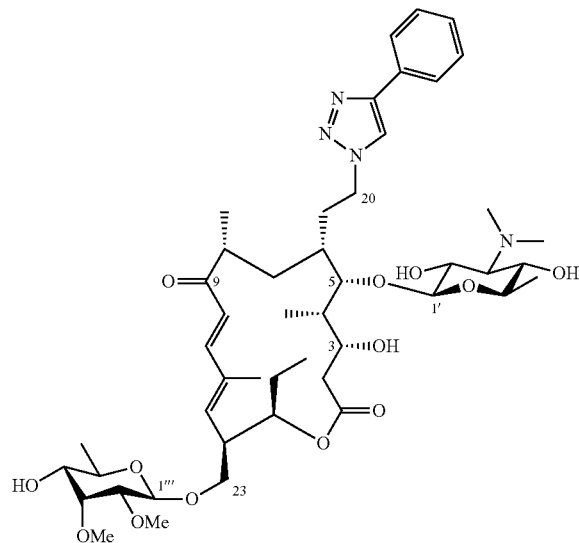
Yield: 98%
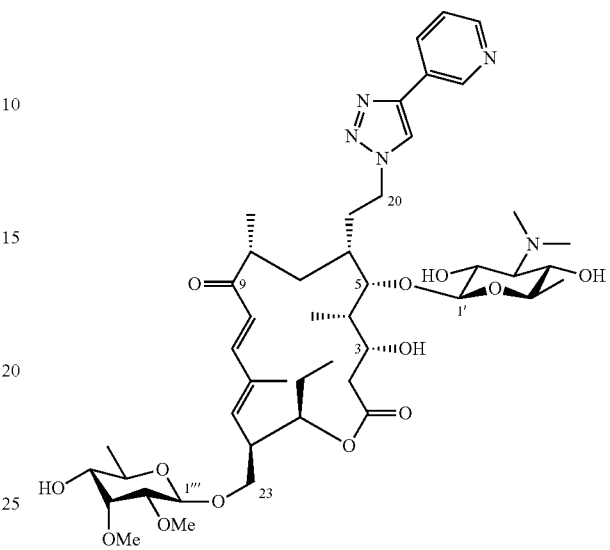
Yield: 82%
20-(4-(thiophene-3-yl)-1H-1,2,3-triazol-1-yl)-20-deoxodesmycosin (YT14)
20-(4-(3-aminophenyl-1H-1,2,3-triazol-1-yl)-20-deoxodesmycosin (YT17)
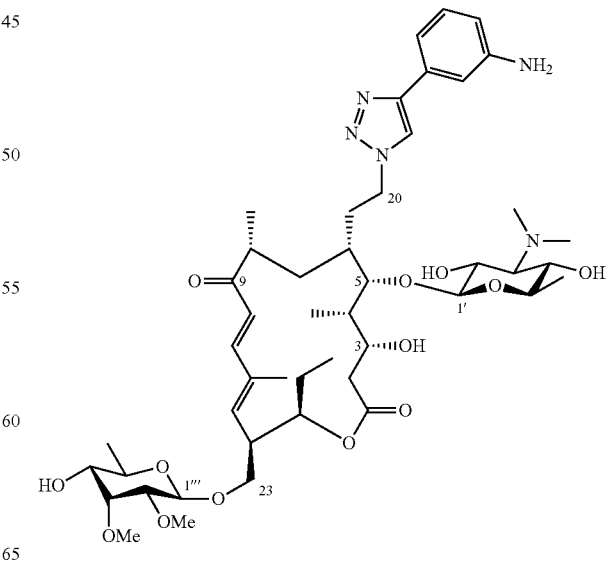
Yield: 81%
Yield: 91%

51
20-(4-(3-aminophenyl-1H-1,2,3-triazol-1-yl)-20-deoxodesmycosin (YT18)
52
20-(4-butyl-1H-1,2,3-triazol-1-yl)-20-deoxodesmycosin (YT20)
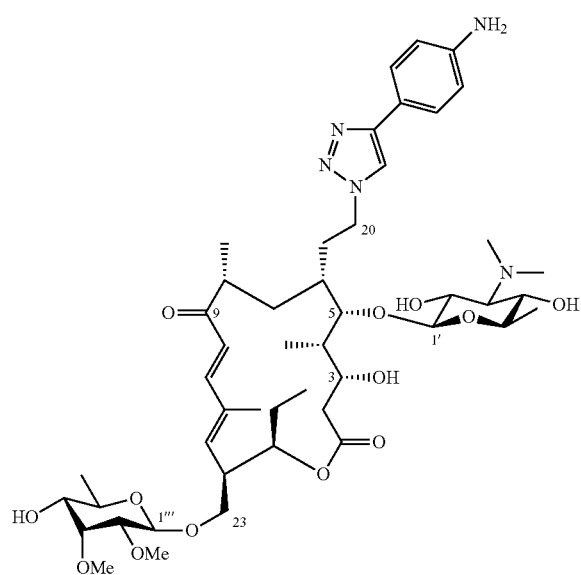
Yield: 67%
Yield: 83%
20-(4-phenyl-1H-1,2,3-triazol-1-yl)-20-deoxodesmycosin (YT21)
20-(4-(4-chlorobutyl)-1H-1,2,3-triazol-1-yl)-20-deoxodesmycosin (YT19)
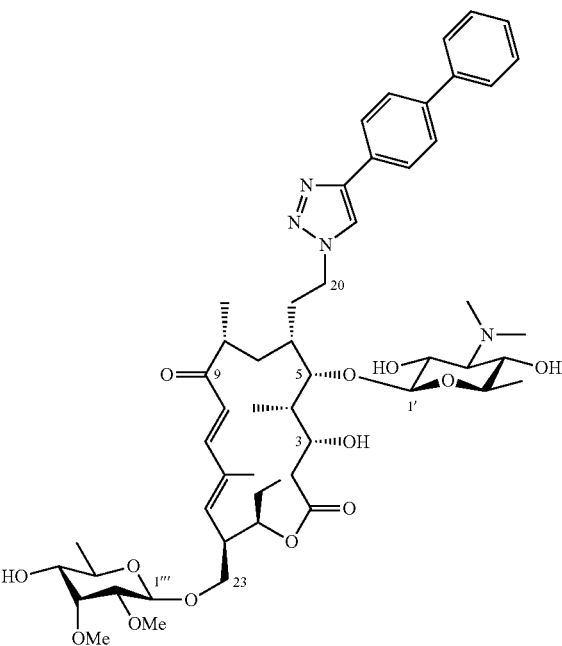
Yield: 54%
Yield: 86%

53
20-(4-ethoxycarbonyl-1H-1,2,3-triazol-1-yl)-20-deoxodesmycosin (YT22)
54
20-(4-(4-phenoxyphenyl)-1H-1,2,3-triazol-1-yl)-20-deoxodesmycosin (YT24)
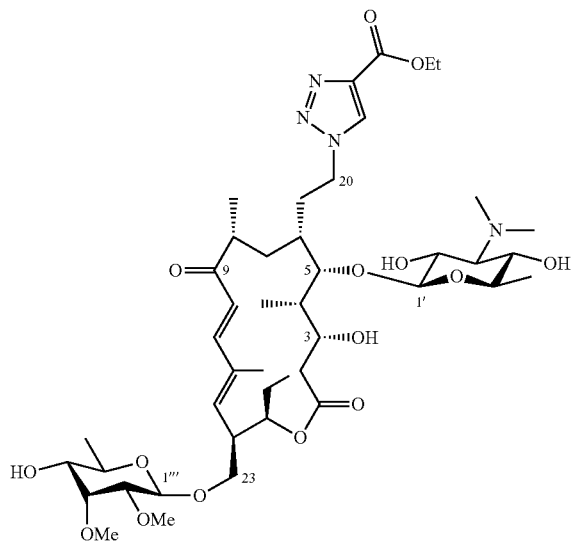
Yield: 86%
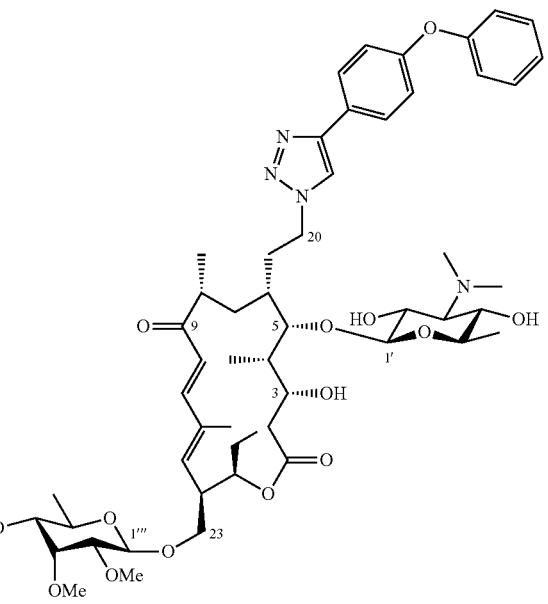
Yield: 85%
20-(4-(phenanthrene-8-yl)-1H-1,2,3-triazol-1-yl)-20-deoxodesmycosin (YT23)
20-(4-(2,4,5-trimethylphenyl)-1H-1,2,3-triazol-1-yl)-20-deoxodesmycosin (YT25)
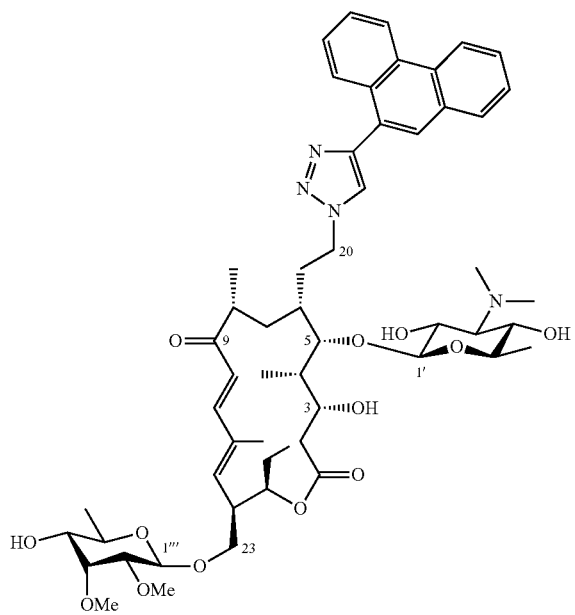
Yield: 93%
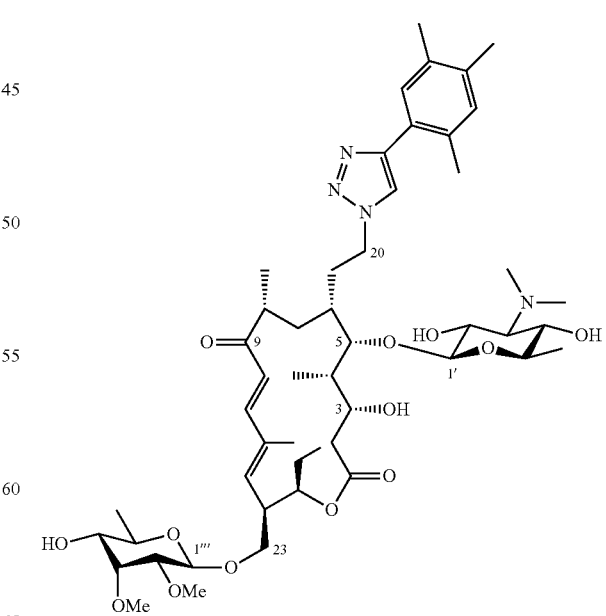
Yield: 73%

55
20-(4-(4-t-butylphenyl)-1H-1,2,3-triazol-1-yl)-20-deoxodesmycosin (YT26)
56
20-(4-(1-methyl-1H-benzotriazole)-1H-1,2,3-triazol-1-yl)-20-deoxodesmycosin (YT28)
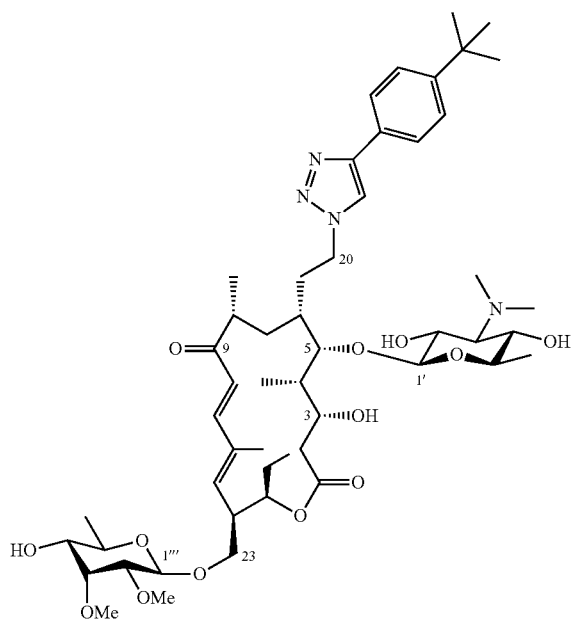
Yield: 88%
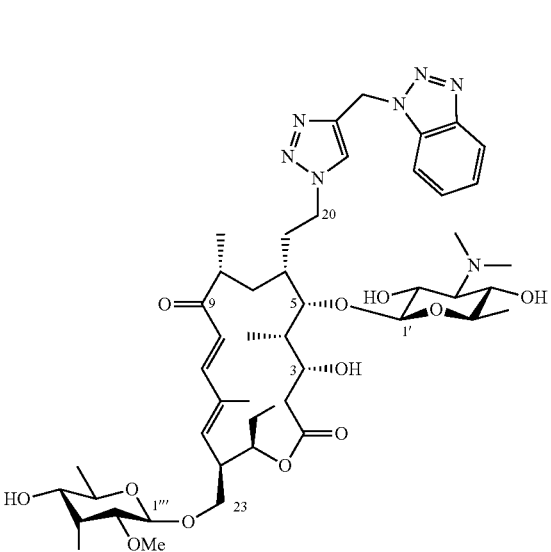
Yield: 96%
20-(4-(4-pentyloxyphenyl)-1H-1,2,3-triazol-1-yl)-20-deoxodesmycosin (YT27)
20-(4-(4-dimethylaminophenyl)-1H-1,2,3-triazol-1-yl)-20-deoxodesmycosin (YT29)
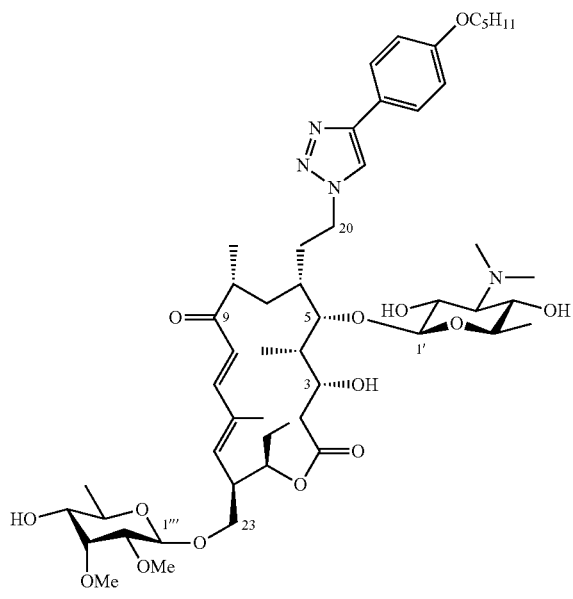
Yield: 86%
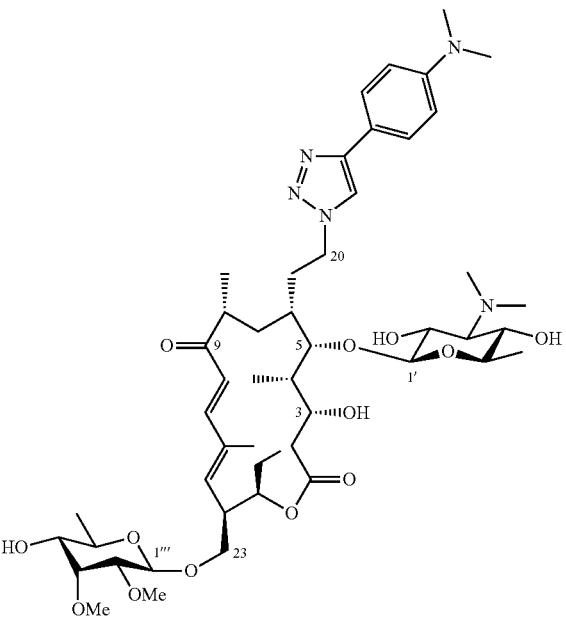
Yield: 89%

57
20-(4-(N-methy-methylamine)-1H-1,2,3-triazol-1-yl)-20-deoxodesmycosin (YT30)
58
20-(4-(2-methy-propyl)-1H-1,2,3-triazol-1-yl)-20-deoxodesmycosin (YT33)
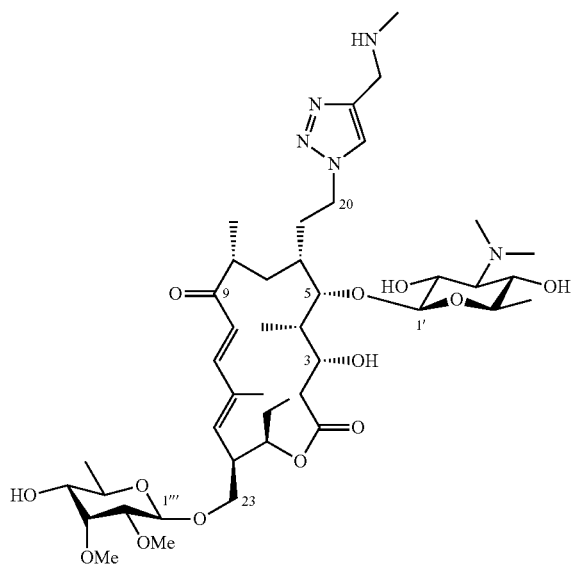
Yield: 80%
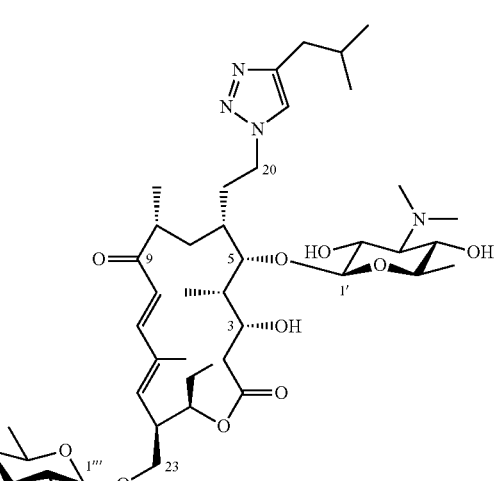
Yield: 89%
20-(4-(1-methy-1-hydroxylethyl)-1H-1,2,3-triazol-1-yl)-20-deoxodesmycosin (YT32)
20-(4-nonyl-1H-1,2,3-triazol-1-yl)-20-deoxodesmycosin (YT34)
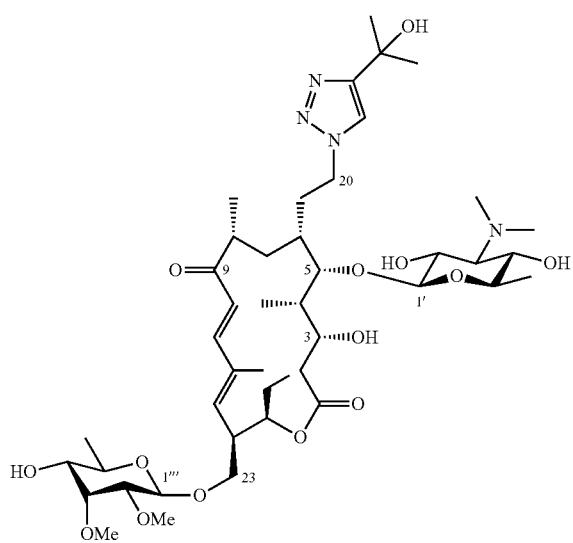
Yield: 92%
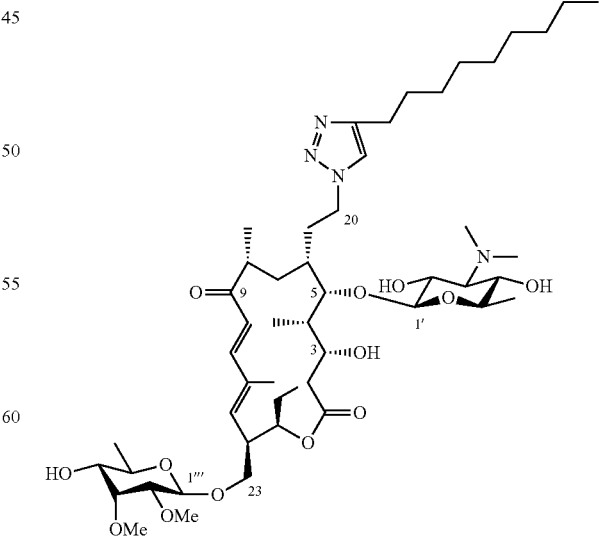
Yield: 97%

59
20-(4-(3-quinoline)-1H-1,2,3-triazol-1-yl)-20-deox-
odesmycosin (YT35)
60
20-(4-(methanol)-1H-1,2,3-triazol-1-yl)-20-deox-
odesmycosin (YT37)
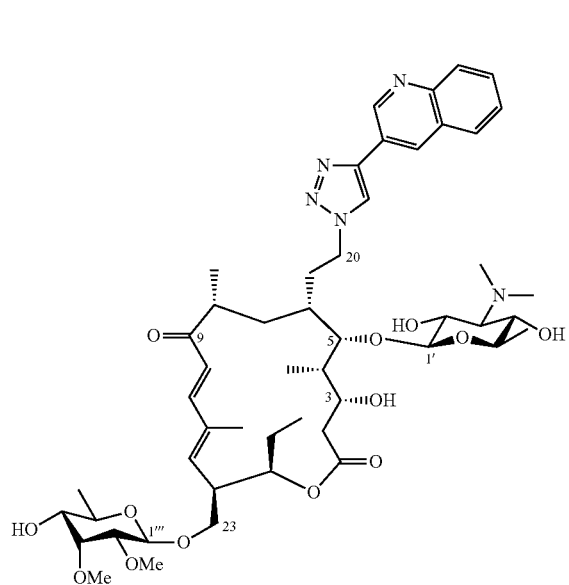
Yield: 93%
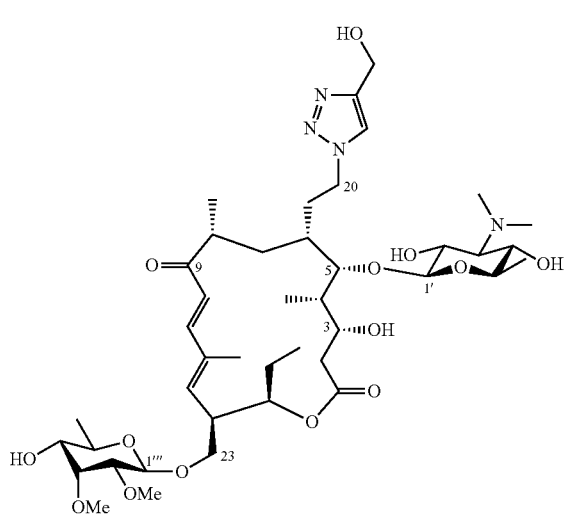
Yield: 100%
20-(4-(4-butanol)-1H-1,2,3-triazol-1-yl)-20-deox-
odesmycosin (YT36)
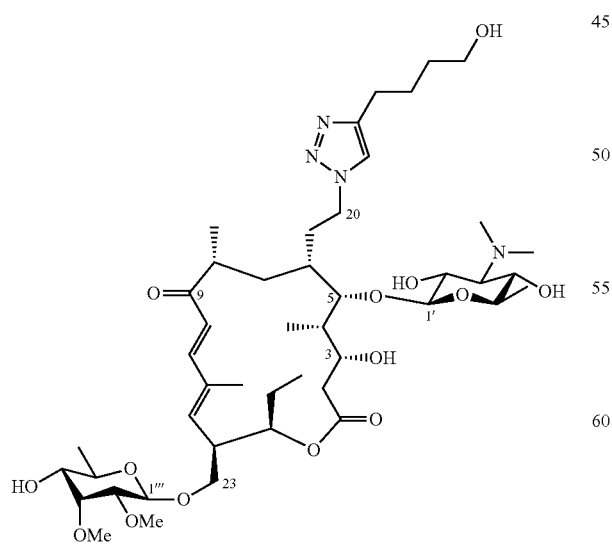
Yield: 97%

Preparation of
23-triazole-23-deoxo-5-O-mycaminosyltylonolides (1) Preparation of 5-O-mycaminosyltylonolide
(YT106)

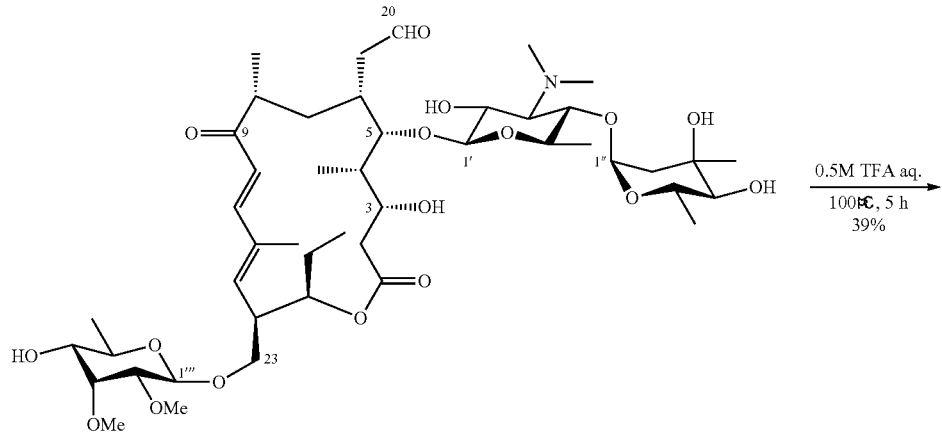

TYL

YT106

Tylosin (9.16 g, 10.0 mmol) was dissolved to 0.5 M TFA solution (300 mL) and then the mixture was stirred for 5 hours at 100° C. After confirming complete consumption of the starting material, the reaction mixture was neutralized by adding $NaHCO_3$ sat. aq., extracted with $CHCl_3$ and dried over $Na_2SO_4$. The solvent was removed under reduced-pressure. The resulting products were purified by flash column chromatography to obtain YT106 (Yield: 39%).

(2) Preparation of
23-azido-23-deoxo-5-O-mycaminosyltylonolide
(YT107)

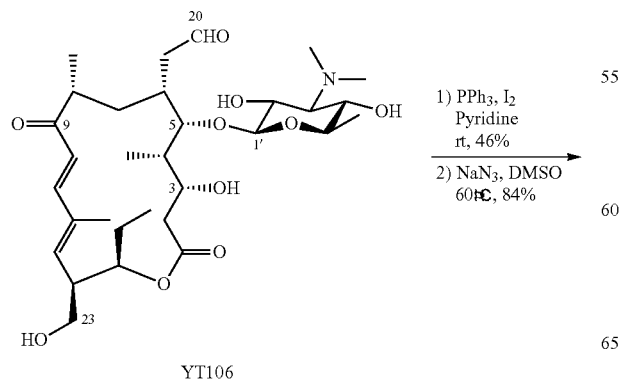

YT106

-continued

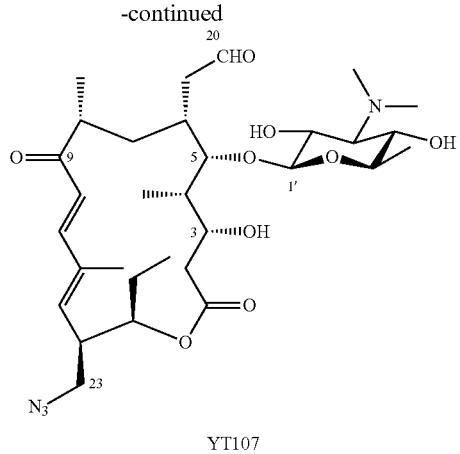

YT107

To a solution of $PPh_3$ (787 mg, 3.0 mmol) and $I_2$ (381 mg, 3.0 mmol) in pyridine (4.0 mL) was added YT106 (300 mg, 0.50 mmol) under $N_2$ atmosphere and then stirred for 4 hours at rt. After confirming complete consumption of the starting material, the reaction mixture was diluted with $CHCl_3$. The organic layer was washed with $Na_2S_2O_3$ sat. aq. and dried over Na$_2$SO$_4$. The solvent was then removed under reduced pressure. The resulting products were purified by flash column chromatography to obtain 23-I-23-deoxo-5-O-mycaminosyltylonolide (Yield: 46%).

To a solution of 23-I-23-deoxo-5-O-mycaminosyltylonolide (155 mg, 0.22 mmol) in DMSO (2.0 mL) was added NaN$_3$ (50 mg, 0.77 mmol) and then the mixture was stirred for 90 minutes at 60° C. After confirming complete consumption of the starting material by mass spectrometry, the reaction mixture was diluted with CHCl$_3$. The organic layer was washed with water and dried over Na$_2$SO$_4$. The solvent was removed under reduced pressure. The resulting products were purified by flash column chromatography to obtain YT107 (Yield: 84%).

(3) Preparation of
23-triazole-23-deoxy-5-O-mycaminosyltylonolides

To a solution of YT107 (0.24 g, 0.30 mmol) in CH$_3$CN or MeOH (3.0 mL) were added CuI (2.9 mg, 0.015 mmol), TBTA (1.6 mg, 3.0 µmol) and a suitable acetylene compound, and then the mixture was stirred at rt until the reaction was completed. After completion, the reaction mixture was diluted with CHCl$_3$, and washed with 10% NH$_3$ aq. After removing CuI, the filtrate was washed with brine. The organic layer was dried over Na$_2$SO$_4$ and concentrated. The resulting products were purified by flash column chromatography to obtain the following triazole compounds:

23-(4-phenyl-1H-1,2,3-triazol-1-yl)-23-Deoxy-5-O-mycaminosyltylonolide (YT101)

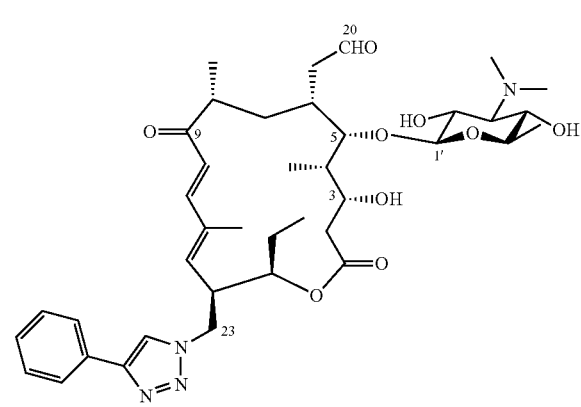

Yield: 64%

Rf: 0.5 (CHCl$_3$:MeOH:NH$_4$OH=8:1:0.008).

23-(4-butyl-1H-1,2,3-triazol-1-yl)-23-Deoxo-5-O-mycaminosyltylonolide (YT102)

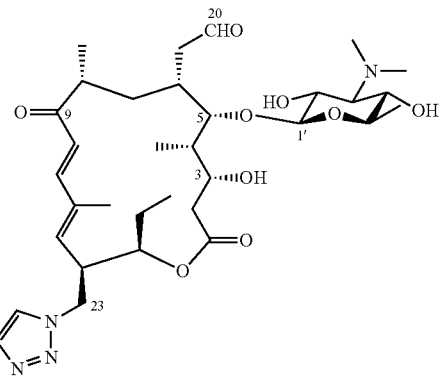

Yield: 77%

23-(4-(3-quinoline-3-yl)-1H-1,2,3-triazol-1-yl)-23-Deoxo-5-O-mycaminosyltylonolide (YT103)

Yield: 100%

23-(4-biphenyl-1H-1,2,3-triazol-1-yl)-23-Deoxy-5-O-mycaminosyltylonolide (YT104)
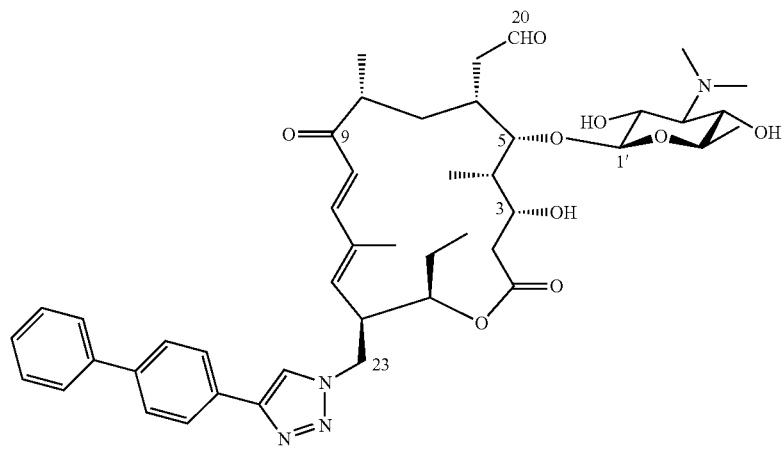
Yield: 100%
23-(4-(pyridine-3-yl)-1H-1,2,3-triazol-1-yl)-23-Deoxo-5-O-mycaminosyltylonolide (YT109)
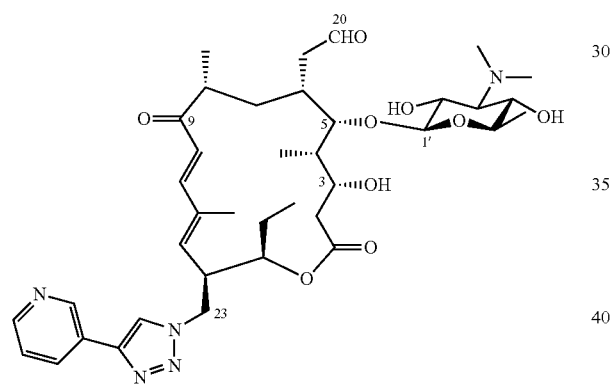
Yield: 94%
23-(4-(methyl-1H-benzotriazolyl)-1H-1,2,3-triazol-1-yl)-23-deoxo-5-O-mycaminosyltylonolide (YT110)
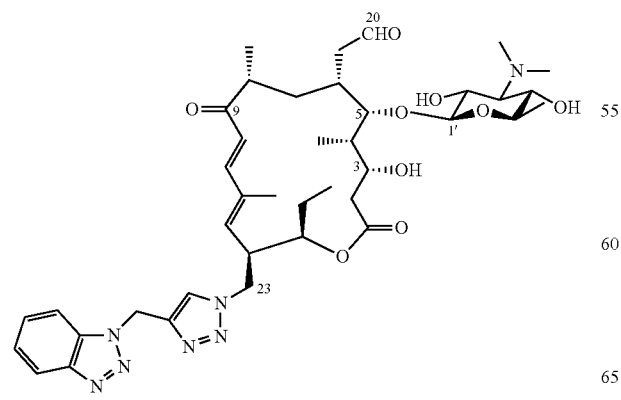
Yield: 94%

Preparation of 20-(4-phenyl-1H-1,2,3-triazol-1-yl)-20-deoxo-23-triazole-23-deoxy-5-O-mycaminosyltylonolides (1) Preparation of 20-(4-phenyl-1H-1,2,3-triazol-1-yl)-20-deoxo-5-O-mycaminosyltylonolide (YT112)

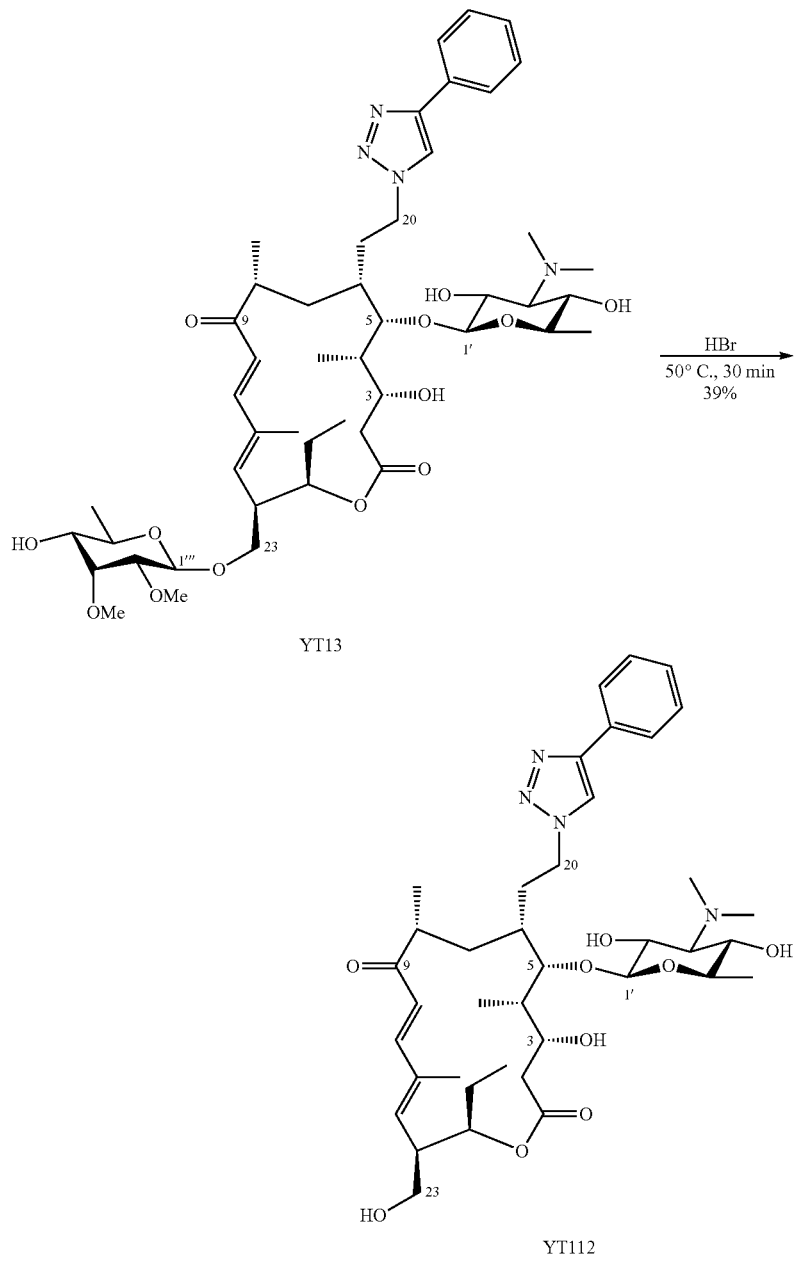

YT13 (0.5 g, 0.56 mmol) was dissolved in HBr (3.0 mL) and then the mixture was stirred for 30 minutes at 50° C. After confirming complete consumption of the starting material, the reaction mixture was neutralized by adding NaHCO$_3$ sat. aq., extracted with CHCl$_3$ and dried over Na$_2$SO$_4$. The solvent was removed under reduced pressure. The resulting products were purified by flash column chromatography to obtain YT112 (Yield: 39%).

(2) Preparation of 20-(4-phenyl-1H-1,2,3-triazol-1-yl)-20-deoxo-23-azido-23-deoxy-5-O-mycaminosyltylonolide (YT114)

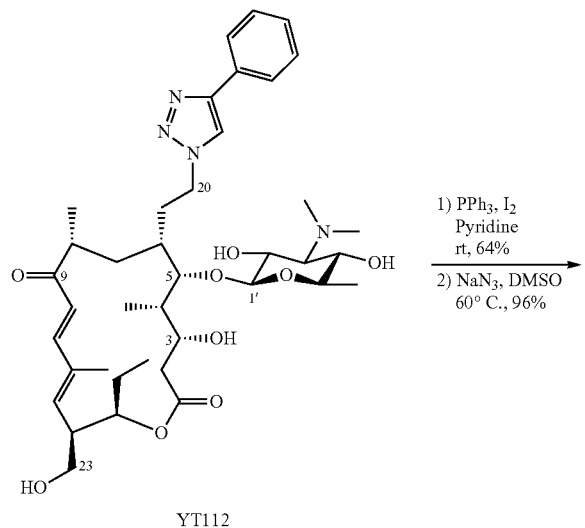

To a solution of PPh₃ (144 mg, 0.55 mmol) and I₂ (70 mg, 0.55 mmol) in pyridine (1.0 mL) was added YT112 (80 mg, 0.11 mmol) under N₂ atmosphere and then the mixture was stirred for 4 hours at rt. After confirming complete consumption of the starting material, the reaction mixture was diluted with CHCl₃. The organic layer was washed with Na₂S₂O₃ sat. aq. and dried over Na₂SO₄. The solvent was removed under reduced pressure. The resulting products were purified by flash column chromatography to obtain 20-(4-phenyl-1H-1,2,3-triazol-1-yl)-20-deoxo-23-I-23-deoxy-5-O-mycaminosyltylonolide (Yield: 64%).

To a solution of 20-(4-phenyl-1H-1,2,3-triazol-1-yl)-20-deoxo-23-I-23-deoxy-5-O-mycaminosyltylonolide (57 mg, 0.068 mmol) in DMSO (0.6 mL) was added NaN₃ (13 mg, 0.20 mmol) and then the mixture was stirred for 30 minutes at 60° C. After confirming complete consumption of the starting material by LC Mass, the reaction mixture was diluted with CHCl₃. The organic layer was washed with water and dried over Na₂SO₄. The solvent was removed under reduced pressure. The resulting products were purified by flash column chromatography to obtain YT114 (Yield: 96%).

(3) Preparation of 20-(4-phenyl-1H-1,2,3-triazol-1-yl)-20-deoxo-23-triazole-23-deoxy-5-O-mycaminosyltylonolides To a solution of YT114 (0.24 g, 0.30 mmol) in CH₃CN or MeOH (3.0 mL) were added CuI (2.9 mg, 0.015 mmol), TBTA (1.6 mg, 3.0 μmol) and a suitable acetylene compound, and then the mixture was stirred at rt until the reaction was completed. After completion, the reaction mixture was diluted with CHCl₃, washed with 10% NH₃ aq. After removing CuI, the filtrate was washed with brine. The organic layer was dried over Na₂SO₄ and concentrated. The resulting products were purified by flash column chromatography to obtain the following triazole compounds:

20-(4-phenyl-1H-1,2,3-triazol-1-yl)-20-deoxo-23-(4-phenyl-1H-1,2,3-triazol-1-yl)-23-deoxy-5-O-mycaminosyltylonolide (YT115)

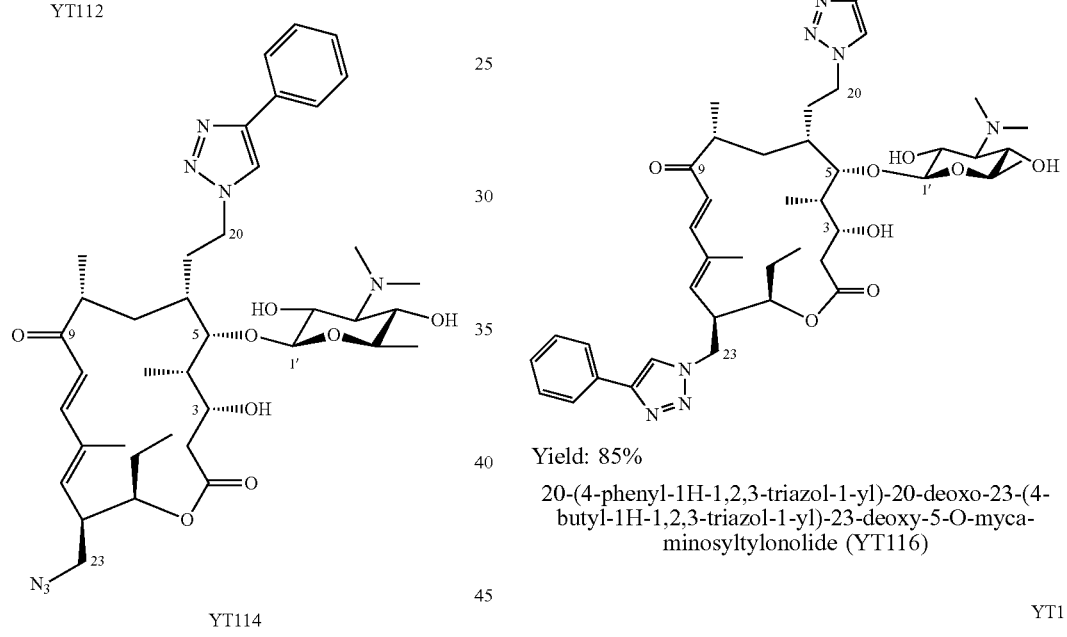

Yield: 85%

20-(4-phenyl-1H-1,2,3-triazol-1-yl)-20-deoxo-23-(4-butyl-1H-1,2,3-triazol-1-yl)-23-deoxy-5-O-mycaminosyltylonolide (YT116)

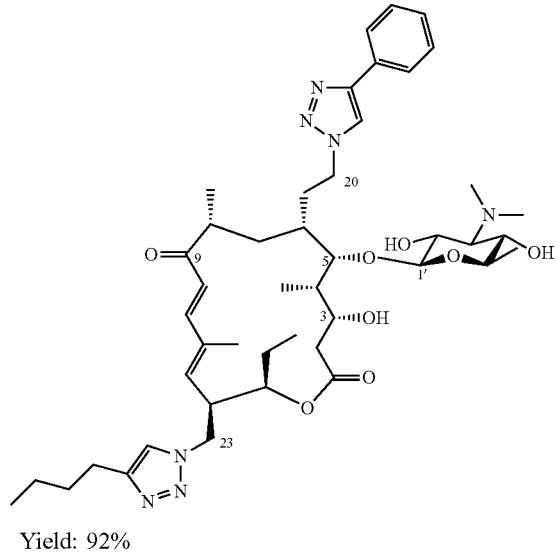

Yield: 92%

Preparation of Compounds of Formula (IIa)

General Procedure for Reductive Amination from O-Mycaminosyltylonolide (OMT)

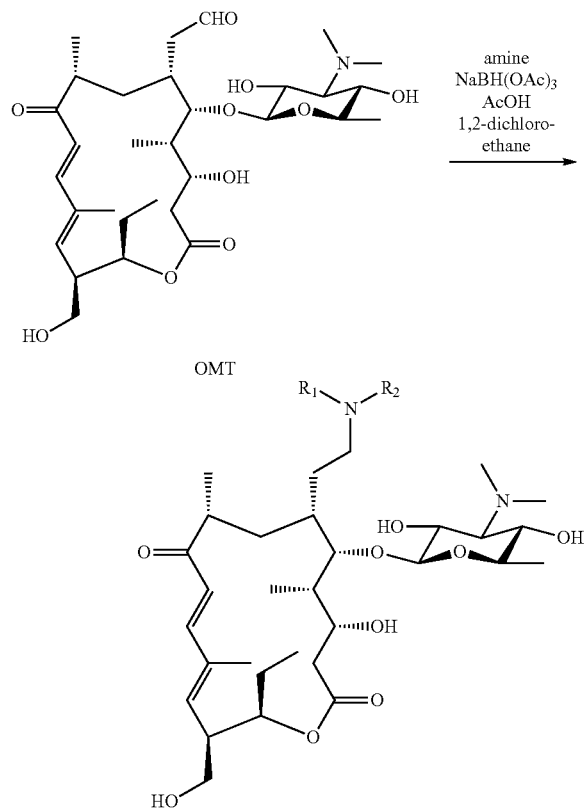

To a solution of O-mycaminosyltylonolide (OMT) in 1,2-dichloroethane (0.1 M) at room temperature was added amines (1.5 to 2.0 equiv.), NaBH(OAc)$_3$ (1.5 equiv.), and AcOH (3.0 equiv.). The reaction mixture was stirred at room temperature until OMT was consumed. After the reaction was quenched with sat. NH$_4$Cl aq., the resulting mixture was extracted with CHCl$_3$ (3 times). The combined organic layers were dried over Na$_2$SO$_4$ and concentrated in vacuo. The crude product was purified by silica gel chromatography (CHCl$_3$/MeOH/NH$_4$OH=100/1/0.1 to 10/1/0.1) to afford desired compounds.

YT615

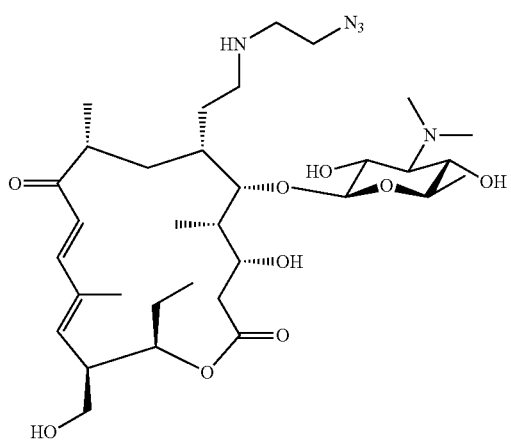

YT615

According to the general procedure for reductive amination with OMT, OMT (200.0 mg, 0.335 mmol) with 2-azidoethylamine in 1.0 M solution of H$_2$O (669.0 mL, 0.669 mmol) was converted to YT615 (124.3 mg, 56%) as a colorless solid.

HRMS (ESI) m/z: 690.4041 [M+Na]$^+$, calcd for C$_{33}$H$_{57}$N$_5$O$_9$Na: 690.4054.

YT646

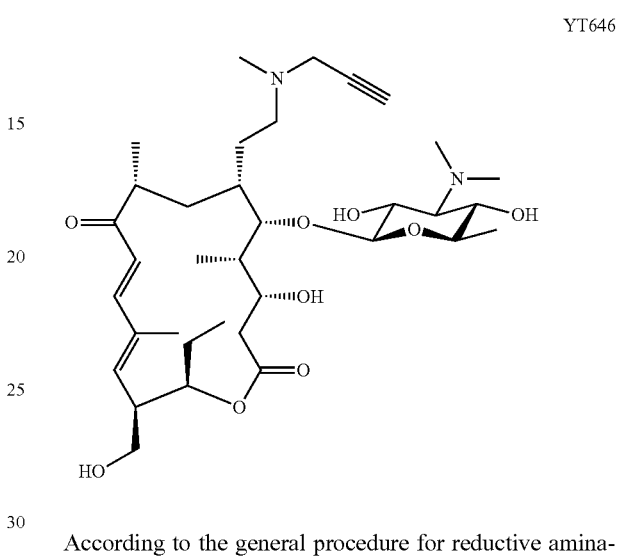

According to the general procedure for reductive amination with OMT, OMT (1.0 g, 1.67 mmol) with N-methylpropargyl amine (209.0 mL, 2.51 mmol) was converted to YT646 (1.01 g, 93%) as a colorless solid. HRMS (ESI) m/z: 651.4202 [M+H]$^+$, calcd for C$_{35}$H$_{59}$N$_2$O$_9$: 651.4221.

YT649

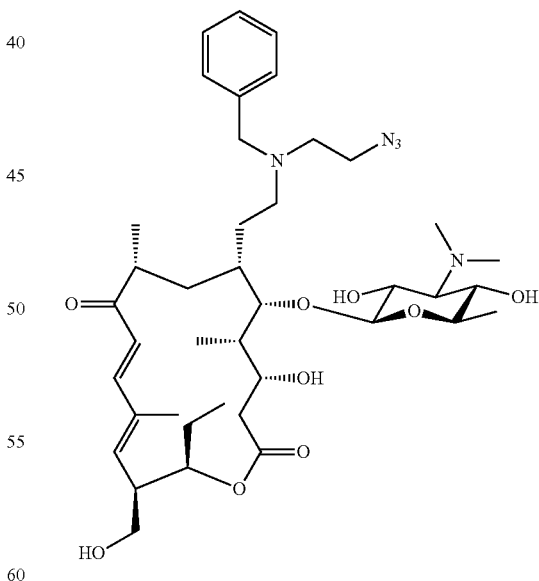

According to the general procedure for reductive amination with OMT, OMT (100 mg, 0.167 mmol) with N-(2-azidoethyl)benzylamine (32.6 μL, 0.251 mmol) was converted to YT649 (98.7 mg, 82%) as a colorless solid. HRMS (ESI) m/z: 758.4700 [M+H]$^+$, calcd for C$_{40}$H$_{64}$N$_5$O$_9$: 758.4704.

YT699

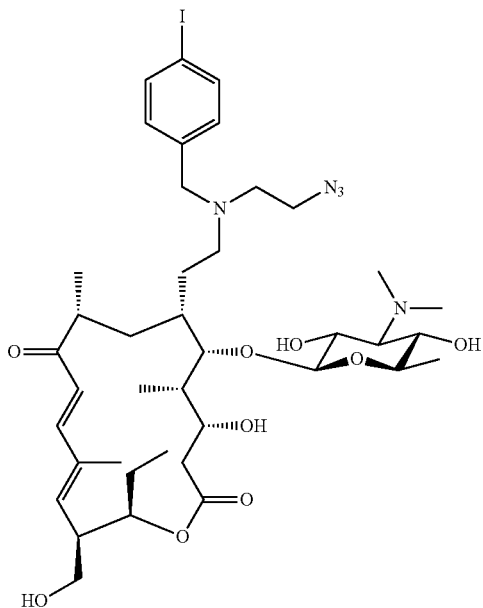

According to the general procedure for reductive amination with OMT, OMT (1.99 g, 3.33 mmol) with N-(2-azidoethyl)-4-iodobenzylamine (1.51 g, 5.00 mmol) was converted to YT699 (2.44 g, 83%) as a colorless solid. HRMS (ESI) m/z: 884.3669 [M+H]$^+$, calcd for $C_{40}H_{63}IN_5O_9$: 884.3670.

YT711

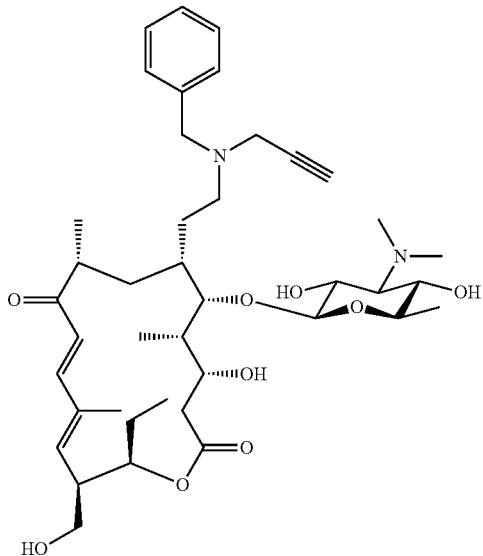

According to the general procedure for reductive amination with OMT, OMT (1.63 g, 2.72 mmol) with N-benzylpropargyl amine (1.66 g, 4.08 mmol) was converted to YT711 (1.49 g, 75%) as a colorless solid. HRMS (ESI) m/z: 727.4532 [M+H]$^+$, calcd for $C_{41}H_{63}N_2O_9$: 727.4534.

YT712

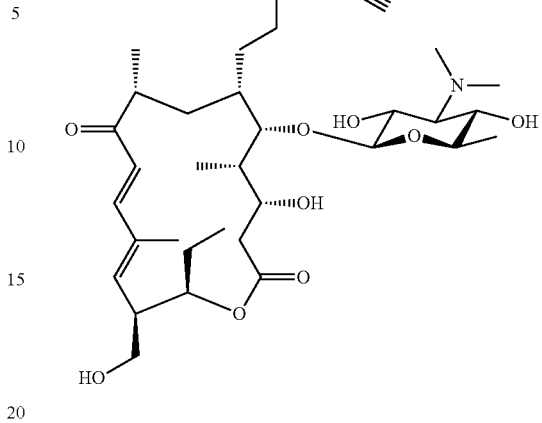

According to the general procedure for reductive amination with OMT, OMT (100.0 mg, 0.167 mmol) with N-propargyl amine (16.1 mL, 0.251 mmol) was converted to YT712 (50.4 mg, 47%) as a colorless solid. HRMS (ESI) m/z: 637.4073 [M+H]$^+$, calcd for $C_{34}H_{57}N_2O_9$: 637.4064.

Synthesis of YT616

YT616

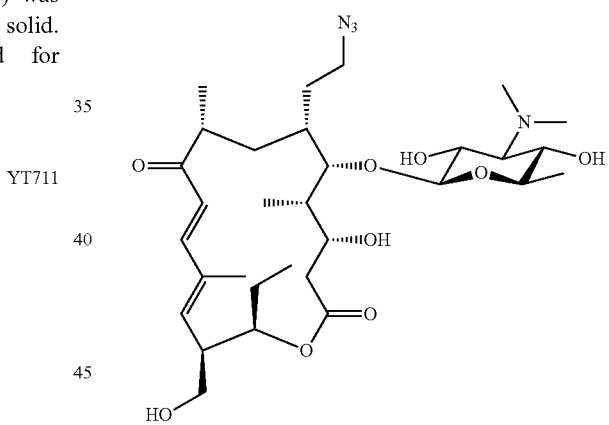

To a solution of OMT (500.0 mg, 0.836 mmol) in pyridine (5 mL) was added AcOH (2.4 mL, 41.8 mmol). The reaction was stirred at room temperature for 1 h. After to the reaction mixture was added water, the solvent was evaporated with toluene. The residue was dissolved in CHCl$_3$ (10 mL), the organic layer was washed with water (5 mL). The organic layer was dried over Na$_2$SO$_4$ and concentrated in vacuo. The crude product was used next step without further purification. To a solution of the crude product in MeOH (6.2 mL) was added NaBH$_4$ (15.8 mg, 0.418 mmol). The reaction was stirred at room temperature for 30 min. After addition of water (3 mL), the mixture was extracted with EtOAc (10 mL, ×3). The combined organic layers were dried over Na$_2$SO$_4$ and concentrated in vacuo. The crude product was used next step without further purification. To a solution of the crude product in toluene (10 mL) was DPPA (215.0 mL, 1.00 mmol) and DBU (140.9 mL, 1.00 mmol). The reaction was stirred at 0° C. for 1 h 15 min. After addition of brine (3 mL), the mixture was extracted with EtOAc (10 mL, ×3). The combined organic layers were dried over Na$_2$SO$_4$ and concentrated in vacuo. The crude product was used next step without further purification. To a solution of the crude product in DMF (6.8 mL) was added NaN$_3$ (108.7 mg, 1.672 mmol). The reaction was stirred at 80° C. for 19 h. After the reaction was cooled to room temperature and diluted with EtOAc, the reaction mixture was washed with H$_2$O. The organic layer was dried over Na$_2$SO$_4$ and concentrated in vacuo. The crude product was used next step without further purification. To a solution of the crude product in MeOH (5.0 mL) was added a solution of 10% K$_2$CO$_3$ in water (3.0 mL). The reaction was stirred at room temperature for 16 h. The reaction mixture was extracted with AcOEt (10 mL, ×3). The combined organic layers were dried over Na$_2$SO$_4$ and concentrated in vacuo. The crude product was purified by silica gel chromatography (CHCl$_3$/MeOH/NH$_4$OH=100/1/0.1 to 10/1/0.1) to afford YT616 (91.7 mg, 18% over 6 steps) as a colorless solid. HRMS (ESI) m/z: 625.3803 [M+H]$^+$, calcd for C$_{31}$H$_{53}$N$_4$O$_9$: 625.3813.

General Procedure for Triazole Reaction.

Method A) To a solution of azide- or acetylene-tylosin analogues in MeOH (0.1 M) at room temperature was added acetylenes or azide building blocks (1.0-2.0 equiv.), tetrakis(acetonitrile)copper(I) hexafluorophosphate (Cu(MeCN)$_4$PF$_6$, 0.1-0.5 mol %), and tris[(1-benzyl-1H-1,2,3-triazol-4-yl)methyl]amine (TBTA, 0.1-0.5 mol %). The reaction mixture was stirred at room temperature until a starting material was consumed. After the reaction was added sat. NH$_4$Cl aq., the resulting mixture was extracted with CHCl$_3$ (3 times). The combined organic layers were dried over Na$_2$SO$_4$ and concentrated in vacuo. The crude product was purified by silica gel chromatography (CHCl$_3$/MeOH/NH$_4$OH=100/1/0.1 to 10/1/0.1) to afford desired compounds.

Method B) To a solution of azide- or acetylene-tylosin analogues in MeOH (0.1 M) at room temperature was added acetylenes or azide building blocks (1.0-2.0 equiv.), tetrakis(acetonitrile)copper(I) hexafluorophosphate (Cu(MeCN)$_4$PF$_6$, 0.1-0.5 mol %), and tris[(1-benzyl-1H-1,2,3-triazol-4-yl)methyl]amine (TBTA, 0.1-0.5 mol %). The reaction mixture was stirred at 70° C. for 15 to 30 min under microwave irradiation until a starting material was consumed. After the reaction was cooled to room temperature and added sat. NH$_4$Cl aq., the resulting mixture was extracted with CHCl$_3$ (3 times).

The combined organic layers were dried over Na$_2$SO$_4$ and concentrated in vacuo. The crude product was purified by silica gel chromatography (CHCl$_3$/MeOH/NH$_4$OH=100/1/0.1 to 10/1/0.1) to afford desired compounds.

Method C) To a solution of azide- or acetylene-tylosin analogues in t-BuOH/H$_2$O (0.03 M) at room temperature was added acetylenes or azide building blocks (1.0-2.0 equiv.), CuSO$_4$ (0.1 mol %), and sodium ascorbate (0.5 equiv.). The reaction mixture was stirred at room temperature until a starting material was consumed. After the reaction was added sat. Rochelle salt aq., the resulting mixture was extracted with AcOEt (3 times). The combined organic layers were dried over Na$_2$SO$_4$ and concentrated in vacuo. The crude product was purified by silica gel chromatography (CHCl$_3$/MeOH/NH$_4$OH=100/1/0.1 to 10/1/0.1) to afford desired compounds.

YT617

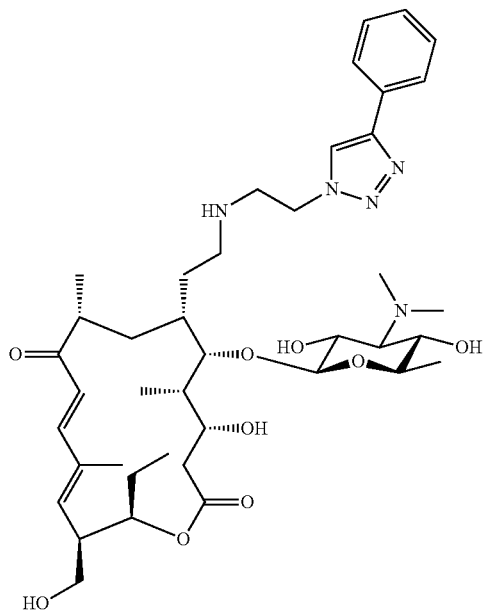

According to the general procedure (method A) for synthesis of triazole analogues, YT615 (67.5 mg, 0.101 mmol) with ethynylbenzene (25.0 μL, 0.228 mmol) was converted to YT617 (41.8 mg, 53%) as a colorless solid. HRMS (ESI) m/z: 770.4676 [M+H]$^+$, calcd for C$_{41}$H$_{64}$N$_5$O$_9$: 770.4704.

YT620

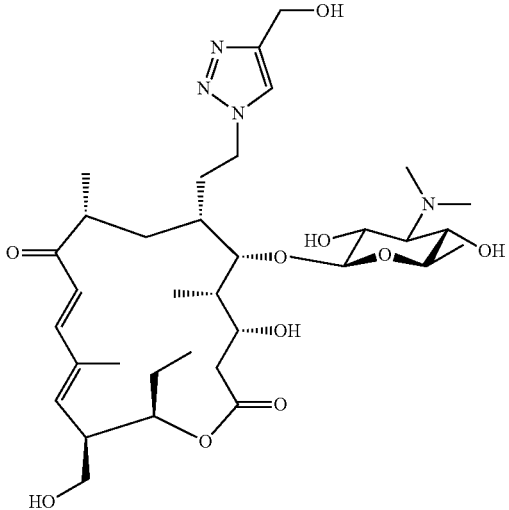

According to the general procedure (method A) for synthesis of triazole analogues, YT616 (47.0 mg, 0.0752 mmol) with 2-propyn-1-ol (9.0 µL, 0.155 mmol) was converted to YT620 (30.5 mg, 61%) as a colorless solid. HRMS (ESI) m/z: 703.3891 [M+Na]$^+$, calcd for $C_{34}H_{56}N_4O_{10}Na$: 703.3894.

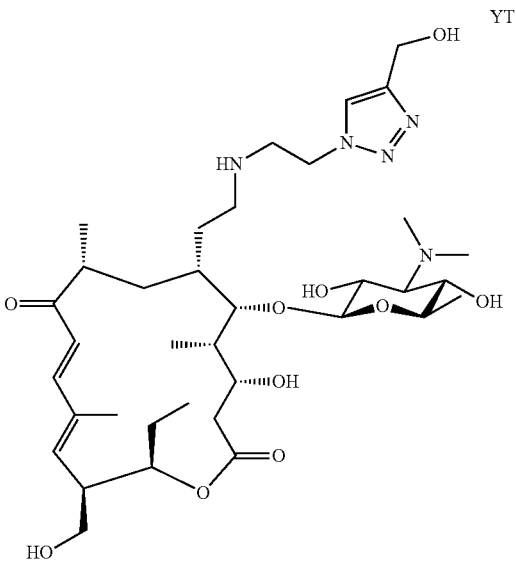

YT625

According to the general procedure (method A) for synthesis of triazole analogues, YT615 (121.3 mg, 0.182 mmol) with 2-propyn-1-ol (21.0 µL, 0.361 mmol) was converted to YT625 (62.9 mg, 48%) as a colorless solid. HRMS (ESI) m/z: 724.4486 [M+H]$^+$, calcd for $C_{36}H_{62}N_5O_{10}$: 724.4497.

According to the general procedure (method A) for synthesis of triazole analogues, YT646 (100.0 mg, 0.154 mmol) with tetra-OAc-β-D-glucopyranosyl azide (86.0 mg, 0.230 mmol) was converted to YT647 (92 mg, 58%) as a colorless solid. HRMS (ESI) m/z: 1024.5336 [M+H]$^+$, calcd for $C_{49}H_{78}N_5O_{18}$: 1024.5342.

According to the general procedure (method A) for synthesis of triazole analogues, YT646 (100.0 mg, 0.154 mmol) with tri-OAc-6-$N_3$-β-D-methylglucopyranoside (79.0 mg, 0.229 mmol) was converted to YT647 (51.8 mg, 50%) as a colorless solid. HRMS (ESI) m/z: 996.5378 [M+H]$^+$, calcd for $C_{48}H_{78}N_5O_{17}$: 996.5393.

According to the general procedure (method B) for synthesis of triazole analogues, YT646 (1.0 g, 1.54 mmol) with 3-azidoquinoline (392.0 mg, 2.30 mmol) using method B) was converted to YT650 (1.21 g, 95%) as a colorless solid. $[\alpha]^{31}_D$ –114.1 (c 1.0, $CHCl_3$); $^1$H NMR (500 MHz, $CD_3OD$) δ (ppm): 9.49 (d, J=2.3 Hz, 1H), 8.90 (d, J=2.3 Hz, 1H), 8.89 (s, 1H), 8.17 (d, J=8.0 Hz, 1H), 8.13 (d, J=8.6 Hz, 1H), 7.89 (app t, J=8.0 Hz, 1H), 7.75 (app t, J=7.7 Hz, 1H), 7.14 (d, J=15.5 Hz, 1H), 6.47 (d, J=15.5 Hz, 1H), 5.51 (d, J=10.3 Hz, 1H), 4.51 (app t, J=8.9 Hz, 1H), 4.23 (d, J=8.0 Hz, 1H), 3.94 (d, J=14.3 Hz, 1H), 3.85 (dd, J=1.7, 9.7 Hz, 1H), 3.59 (d, J=10.3 Hz, 1H), 3.52 (d, J=13.8 Hz, 1H), 3.42 (dd, J=4.0, 10.9 Hz, 1H), 3.35 (dd, J=8.0, 10.9 Hz, 1H), 3.26-3.19 (complex m, 2H), 3.13 (app t, J=9.5 Hz, 1H), 2.86 (m, 1H), 2.76 (m, 1H), 2.66 (m, 1H), 2.50 (s, 6H), 2.45-2.29 (complex m, 3H), 2.23 (s, 3H), 2.05 (d, J=17.2 Hz, 1H), 1.88-1.73 (complex m, 3H), 1.80 (s, 3H), 1.72-1.63 (complex m, 2H), 1.59-1.42 (complex m, 3H), 1.24 (d, J=5.7 Hz, 3H), 1.21 (d, J=6.9 Hz, 3H), 1.20 (d, J=6.9 Hz, 3H), 0.84 (t, J=7.5 Hz, 3H). $^{13}$C NMR (125 MHz, CD$_3$OD) δ (ppm): 206.5, 174.3, 149.6, 148.4, 146.8, 145.2, 144.9, 136.5, 132.2, 132.0, 129.9, 129.7, 129.4, 129.1, 128.9, 124.3, 119.4, 105.7, 80.6, 76.1, 74.3, 72.6, 71.73, 71.66, 68.4, 62.4, 56.0 52.7, 48.3, 46.7, 43.1, 42.7, 42.2 (2C), 40.3, 34.9, 34.1, 26.2, 26.1, 18.3, 17.9, 13.2, 9.9, 9.7; HRMS (ESI) m/z: 821.4812 [M+H]$^+$, calcd for C$_{44}$H$_{65}$N$_6$O$_9$: 821.4813.

YT651

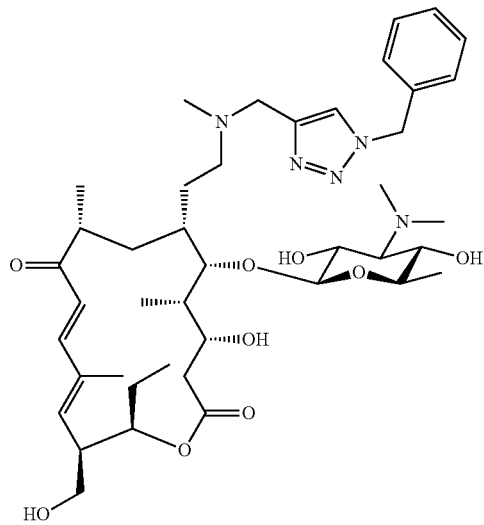

According to the general procedure (method C) for synthesis of triazole analogues, YT646 (100.0 mg, 0.154 mmol) with azidomethyl benzene (30.8 mg, 0.230 mmol) was converted to YT651 (86.1 mg, 71%) as a pale yellow solid. HRMS (ESI) m/z: 784.4851 [M+H]$^+$, calcd for C$_{42}$H$_{66}$N$_5$O$_9$: 784.4861.

YT652

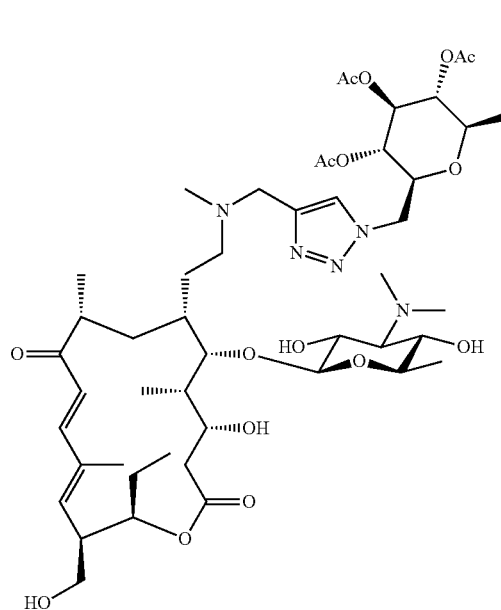

According to the general procedure (method A) for synthesis of triazole analogues, YT646 (100.0 mg, 0.154 mmol) with 2-acetamido-4,6-O-benzylidene-2-deoxy-β-D-glucopyranosylazide (62.0 mg, 0.185 mmol) was converted to YT652 (117.8 mg, 78%) as a pale yellow solid. HRMS (ESI) m/z: 985.5477 [M+H]$^+$, calcd for C$_{50}$H$_{77}$N$_6$O$_{14}$: 985.5498.

YT653

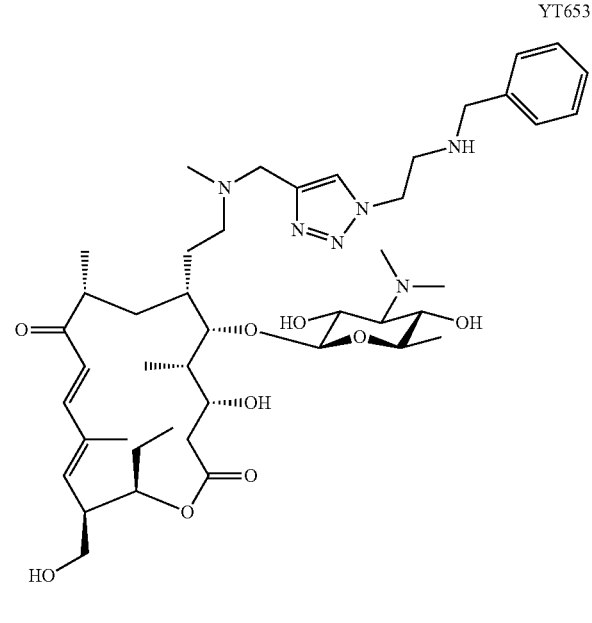

According to the general procedure (method C) for synthesis of triazole analogues, YT646 (100.0 mg, 0.154 mmol) with N-(2-azidoethyl)-benzylamine (40.6 mg, 0.230 mmol) was converted to YT653 (103.9 mg, 82%) as a pale yellow solid. HRMS (ESI) m/z: 827.5277 [M+H]$^+$, calcd for C$_{44}$H$_7$N$_6$O$_9$: 827.5283.

YT654

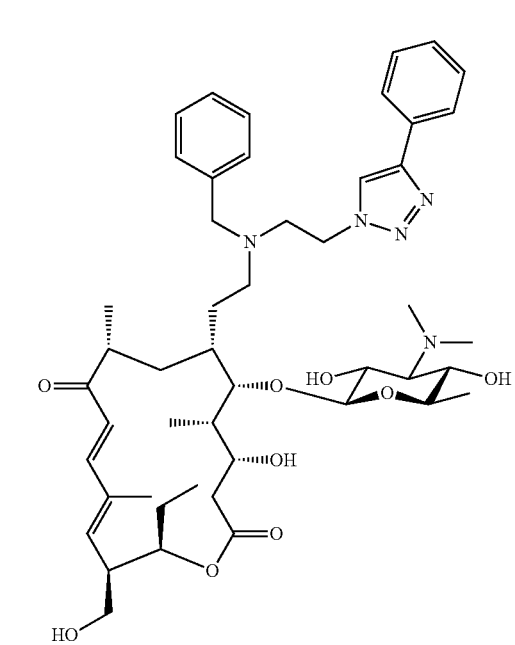

According to the general procedure (method C) for synthesis of triazole analogues, YT649 (100.0 mg, 0.132 mmol) with ethynylbenzene (21.7 μL, 0.198 mmol) was converted to YT654 (106.6 mg, 94%) as a pale yellow solid. HRMS (ESI) m/z: 860.5157 [M+H]$^+$, calcd for $C_{48}H_{70}N_5O_9$: 860.5174.

with 3-ethynylpyridine (27.0 mg, 0.262 mmol) was converted to YT664 (46.9 mg, 41%) as a pale yellow solid. HRMS (ESI) m/z: 861.5110 [M+Na]$^+$, calcd for $C_{45}H_{70}N_6O_9Na$: 861.5102.

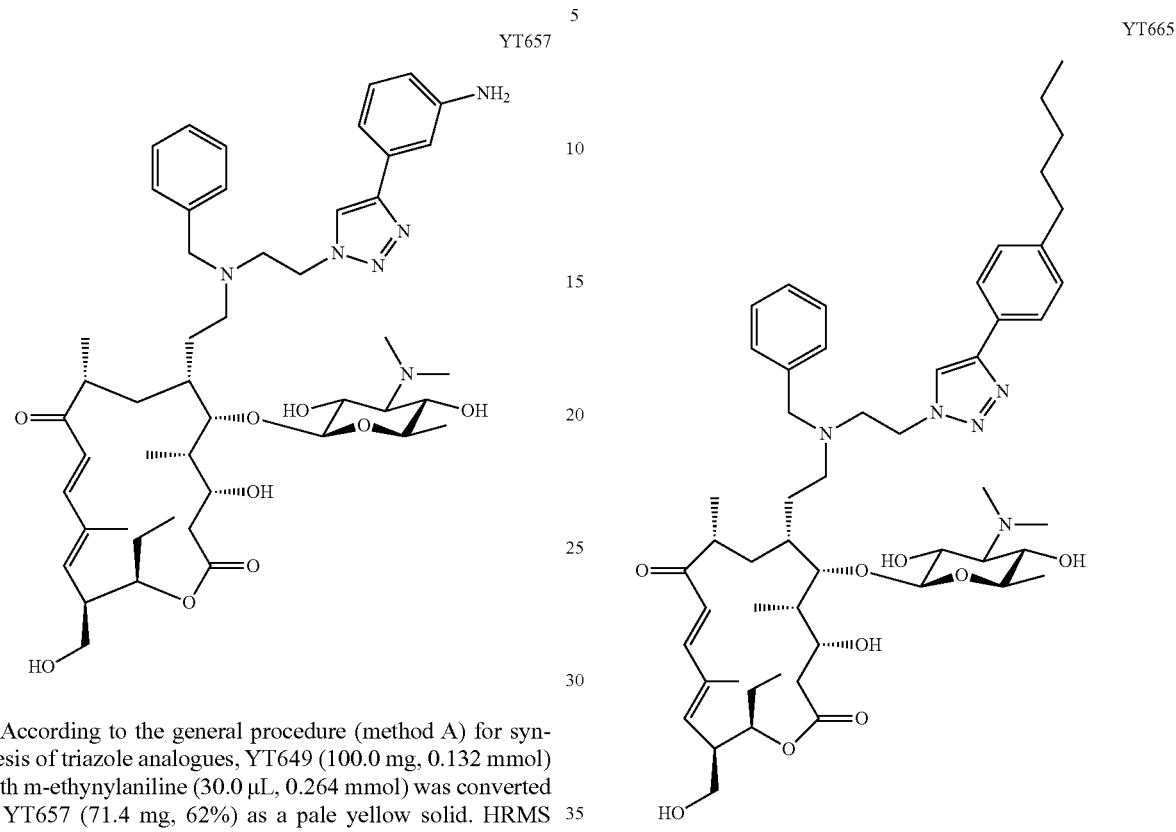

According to the general procedure (method A) for synthesis of triazole analogues, YT649 (100.0 mg, 0.132 mmol) with m-ethynylaniline (30.0 µL, 0.264 mmol) was converted to YT657 (71.4 mg, 62%) as a pale yellow solid. HRMS (ESI) m/z: 875.5262 [M+H]$^+$, calcd for $C_{48}H_{71}N_6O_9$: 875.5283.

According to the general procedure (method A) for synthesis of triazole analogues, YT649 (100.0 mg, 0.132 mmol) with 1-ethynyl-4-pentylbenzene (51.0 µL, 0.263 mmol) was converted to YT665 (46.6 mg, 38%) as a pale yellow solid. HRMS (ESI) m/z: 952.5767 [M+Na]$^+$, calcd for $C_{53}H_{79}N_5O_9Na$: 952.5776.

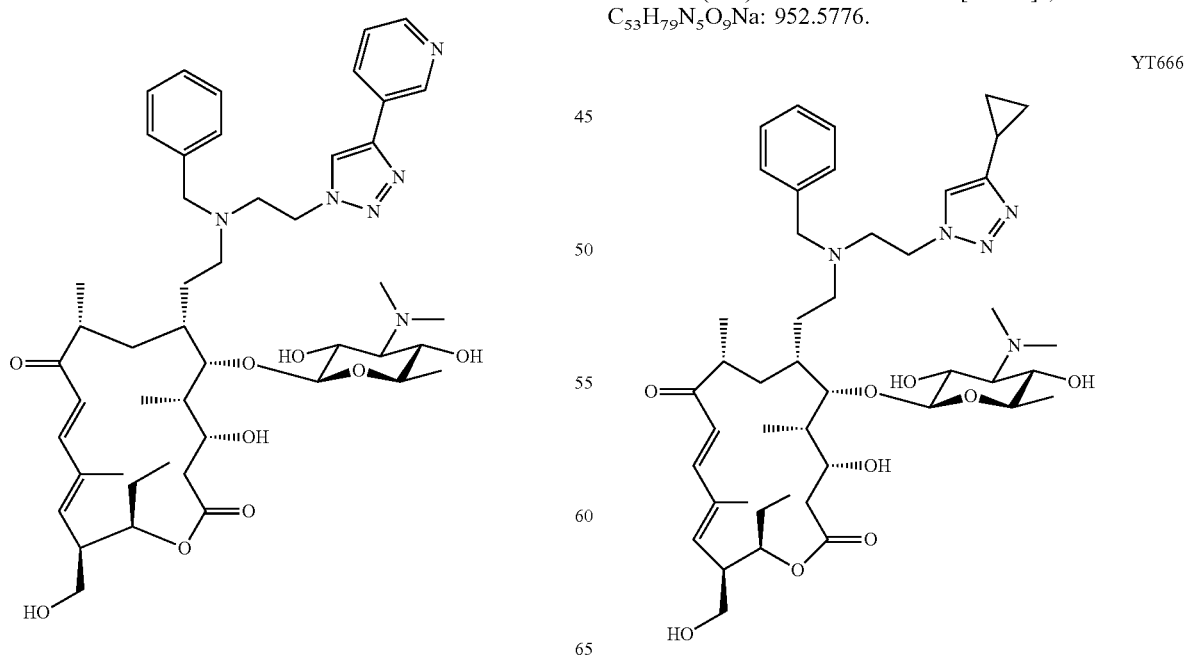

According to the general procedure (method A) for synthesis of triazole analogues, YT649 (100.0 mg, 0.132 mmol)

According to the general procedure (method A) for synthesis of triazole analogues, YT649 (100.0 mg, 0.132 mmol)

with cyclopropylacetylene (22.0 µL, 0.260 mmol) was converted to YT666 (30.4 mg, 28%) as a pale yellow solid. HRMS (ESI) m/z: 846.4986 [M+Na]+, calcd for $C_{45}H_{69}N_5O_9Na$: 846.4993.

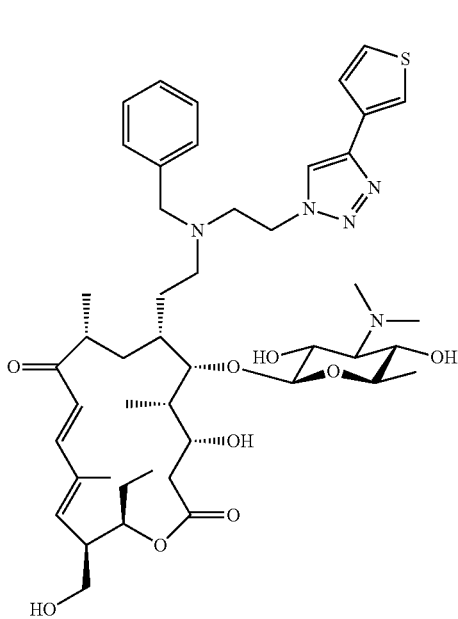

YT674

According to the general procedure (method A) for synthesis of triazole analogues, YT649 (100 mg, 0.132 mmol) with 3-ethynylthiophene (19.5 µL, 0.198 mmol) was converted to YT674 (49.2 mg, 43%) as a pale yellow solid. HRMS (ESI) m/z: 866.4738 [M+H]+, calcd for $C_{46}H_{68}N_5O_9S$: 866.4738.

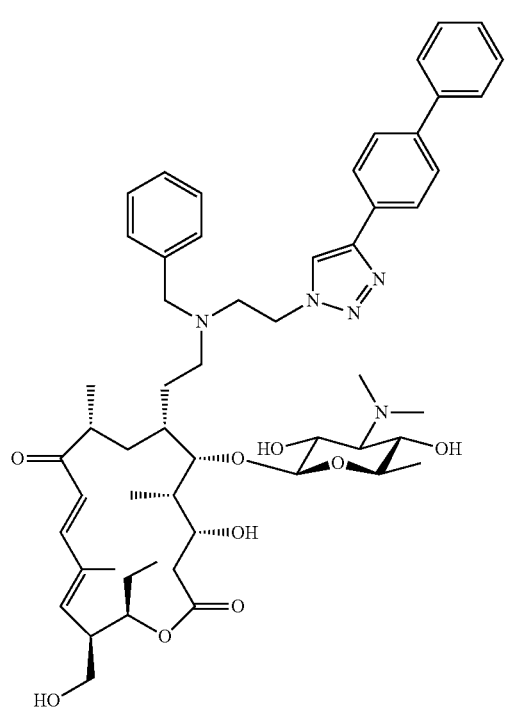

YT680

According to the general procedure (method A) for synthesis of triazole analogues, YT649 (100 mg, 0.132 mmol) with 4-ethynylbiphenyl (35.3 mg, 0.198 mmol) was converted to YT680 (48.2 mg, 39%) as a pale yellow solid. HRMS (ESI) m/z: 936.5478 [M+H]+, calcd for $C_{54}H_{74}N_5O_9$: 936.5487.

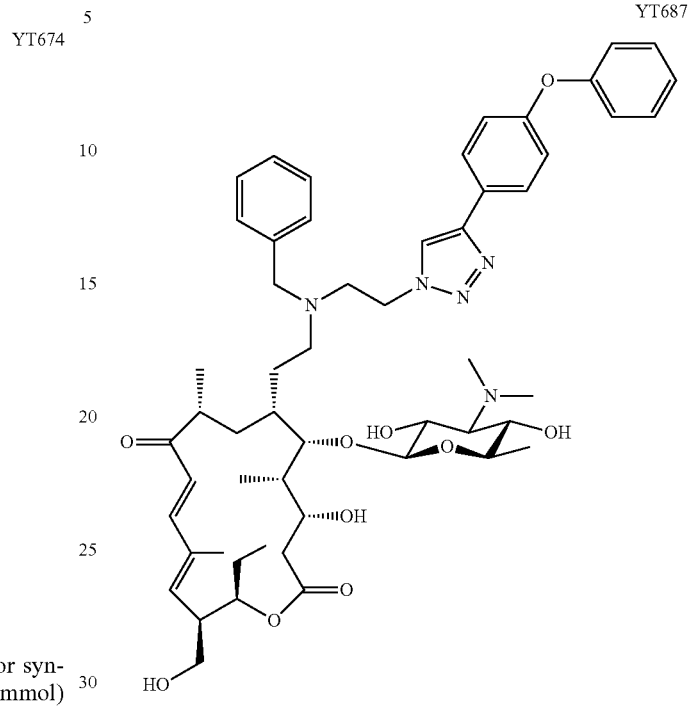

YT687

According to the general procedure (method C) for synthesis of triazole analogues, YT649 (100 mg, 0.132 mmol) with 1-ethynyl-4-phenoxybenzene (35.9 µL, 0.198 mmol) was converted to YT687 (57.6 mg, 46%) as a pale yellow solid. HRMS (ESI) m/z: 952.5444 [M+H]+, calcd for $C_{54}H_{74}N_5O_{10}$: 952.5434.

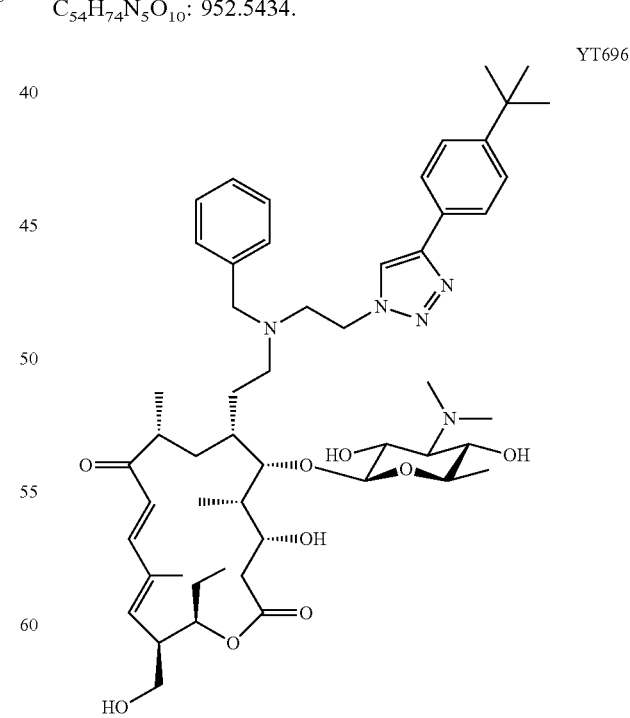

YT696

According to the general procedure (method A) for synthesis of triazole analogues, YT649 (100 mg, 0.132 mmol) with p-t-butylphenylacetylene (47.0 µL, 0.264 mmol) was converted to YT696 (55.7 mg, 46%) as a pale yellow solid. HRMS (ESI) m/z: 916.5784 [M+H]+, calcd for $C_{52}H_{78}N_5O_9$: 916.5800.

verted to YT701 (102.9 mg, 86%) as a pale yellow solid. HRMS (ESI) m/z: 1062.4446 [M+H]+, calcd for $C_{54}H_{73}IN_5O_9$: 1062.4453.

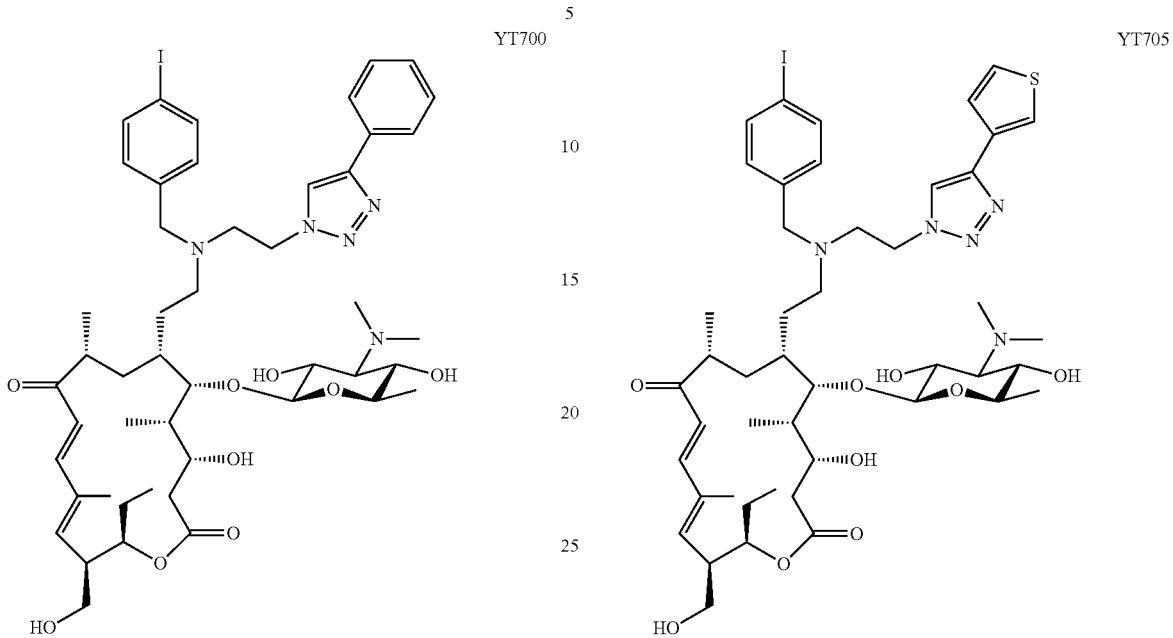

According to the general procedure (method B) for synthesis of triazole analogues, YT699 (100.0 mg, 0.133 mmol) with ethynyl benzene (18.7 μL, 0.170 mmol) was converted to YT700 (92.7 mg, 83%) as a pale yellow solid. HRMS (ESI) m/z: 986.4143 [M+H]+, calcd for $C_{48}H_{69}IN_5O_9$: 986.4140.

According to the general procedure (method B) for synthesis of triazole analogues, YT699 (100.0 mg, 0.133 mmol) with 3-ethynylthiophene (17.4 μL, 0.170 mmol) was converted to YT705 (100.5 mg, 71%) as a pale yellow solid. HRMS (ESI) m/z: 992.3687 [M+H]+, calcd for $C_{46}H_{67}IN_5O_9S$: 992.3704.

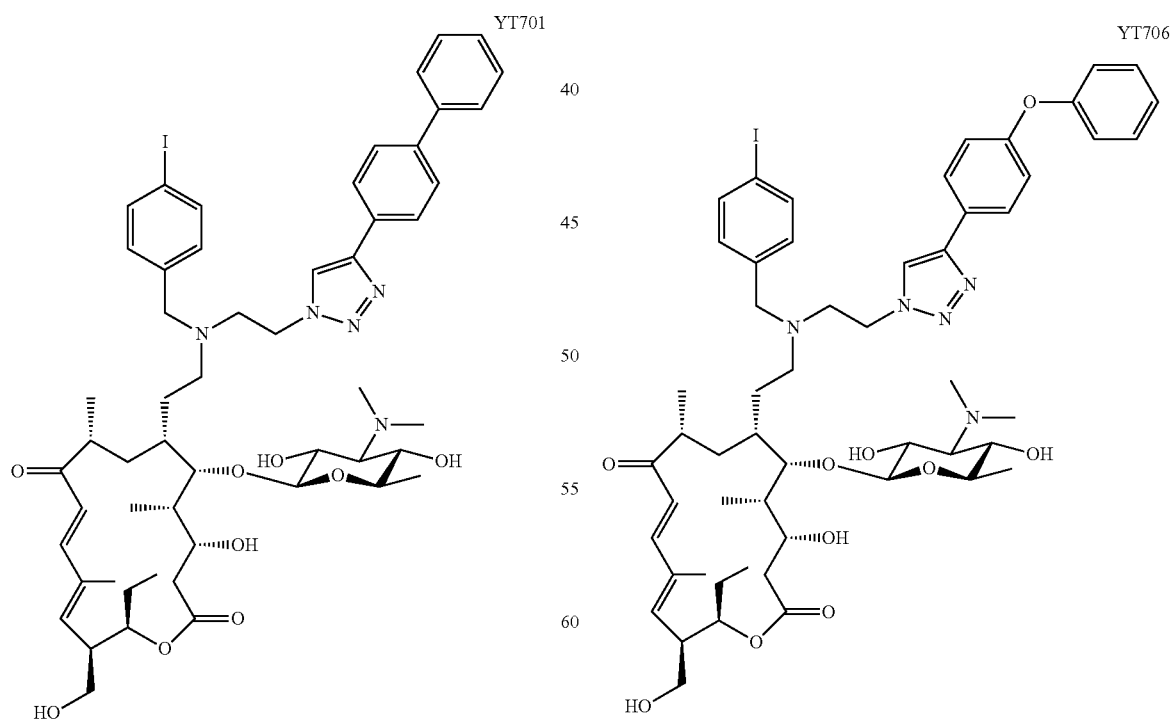

According to the general procedure (method B) for synthesis of triazole analogues, YT699 (100.0 mg, 0.133 mmol) with 4-ethynyl biphenyl (30.3 mg, 0.170 mmol) was con- According to the general procedure (method B) for synthesis of triazole analogues, YT699 (100.0 mg, 0.133 mmol) with 1-ethynyl-4-phenoxybenzene (31.8 μL, 0.170 mmol)

was converted to YT706 (97.2 mg, 68%) as a pale yellow solid. HRMS (ESI) m/z: 1078.4388 [M+H]$^+$, calcd for $C_{54}H_{73}IN_5O_{10}$: 1078.4402.

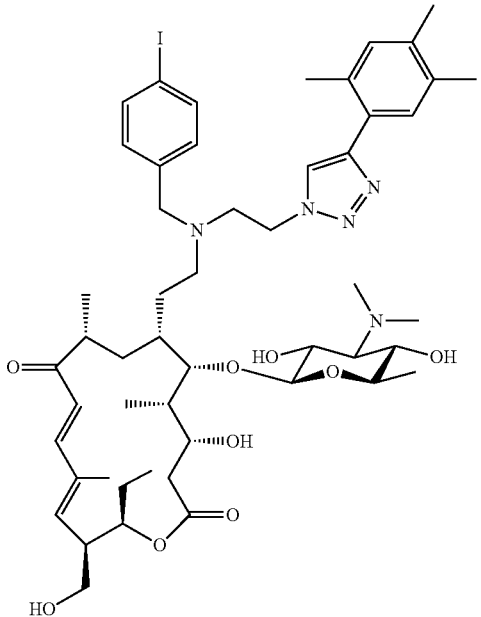

YT707

According to the general procedure (method B) for synthesis of triazole analogues, YT699 (100.0 mg, 0.133 mmol) with 1-ethynyl-2,4,5-trimethyl benzene (25.3 mg, 0.170 mmol) was converted to YT707 (99.8 mg, 73%) as a pale yellow solid. HRMS (ESI) m/z: 1028.4588 [M+H]$^+$, calcd for $C_{51}H_{75}IN_5O_9$: 1028.4609.

YT708

HRMS (ESI) m/z: 694.4379 [M+H]$^+$, calcd for $C_{35}H_{60}N_5O_9$: 694.4391.

YT709

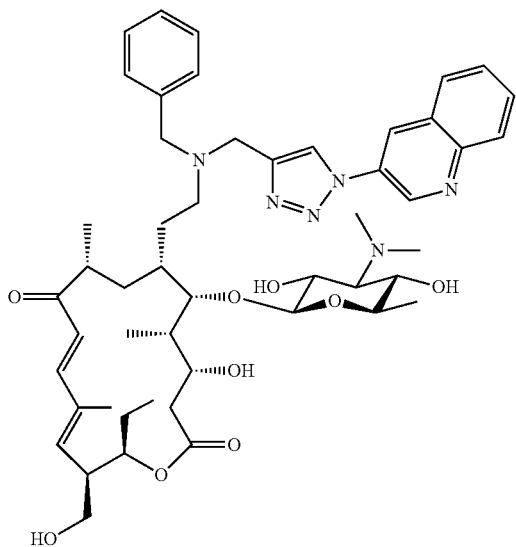

According to the general procedure (method B) for synthesis of triazole analogues, YT711 (100.0 mg, 0.138 mmol) with 3-azidoquinoline (30.4 mg, 0.179 mmol) was converted to YT709 (113.9 mg, 92%) as a colorless solid. [α]$^{31}_D$ −124.7 (c 1.0, CHCl$_3$); $^1$H NMR (500 MHz, CD$_3$OD) δ (ppm): 9.49 (d, J=2.3 Hz, 1H), 8.95 (s, 1H), 8.89 (d, J=2.3 Hz, 1H), 8.16 (d, J=8.6 Hz, 1H), 8.12 (d, J=8.6 Hz, 1H), 7.88 (app t, J=8.0 Hz, 1H), 7.74 (app t, J=8.0 Hz, 1H), 7.44 (d, J=7.5 Hz, 2H), 7.38 (app t, J=7.5 Hz, 2H), 7.27 (t, J=7.5 Hz, 1H), 7.10 (d, J=15.5 Hz, 1H), 6.48 (d, J=15.5 Hz, 1H), 5.72 (d, J=10.9 Hz, 1H), 4.78 (m, 1H), 4.01-3.67 (complex m, 3H), 3.94 (d, J=7.5 Hz, 1H), 3.57-3.43 (complex m, 4H), 3.26 (dd, J=10.3, 8.0 Hz, 1H), 3.20 (d, J=12.6 Hz, 1H), 3.02 (t, 9.7 Hz, 1H), 2.97 (m, 1H), 2.87-2.78 (complex m, 2H), 2.67 (m, 1H), 2.54 (dd, J=17.2, 10.3 Hz, 1H), 2.45 (s, 6H), 2.22-2.15 (complex m, 2H), 2.08 (d, J=17.2 Hz, 1H), 1.94 (m, 1H), 1.84 (s, 3H), 1.83-1.46 (complex m, 7H), 1.21 (d, J=6.9 Hz, 3H), 1.04 (d, J=6.3 Hz, 3H), 1.03 (d, J=6.9 Hz, 3H), 0.91 (t, J=7.5 Hz, 3H). $^{13}$C NMR (125 MHz, CD$_3$OD) δ (ppm): 206.7, 174.6, 149.5, 148.4, 147.7, 144.7, 144.5, 139.6, 136.6, 132.2, 131.9, 130.8 (2C), 129.8, 129.6, 129.5 (2C), 129.4, 129.0, 128.4, 128.2, 124.2, 119.6, 105.6, 80.5, 76.3, 74.2, 72.5, 71.7, 71.6, 68.6, 62.5, 59.8, 52.4, 50.4, 48.3, 46.5, 42.9, 42.1 (2C), 40.5, 34.9, 34.2, 26.2 (2C), 18.1, 17.9, 13.3, 10.0, 9.8. HRMS (ESI) m/z: 897.5111 [M+H]$^+$, calcd for $C_{50}H_{69}N_6O_9$: 897.5126.

YT710

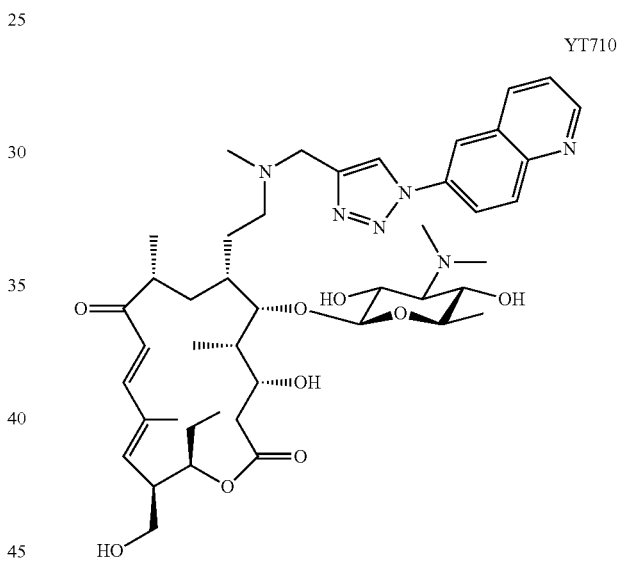

According to the general procedure (method B) for synthesis of triazole analogues, YT650 (100.0 mg, 0.154 mmol) with 6-azidoquinoline (39.1 mg, 0.230 mmol) was converted to YT710 (115.3 mg, 91%) as a pale yellow solid.

$^1$H NMR (500 MHz, CD$_3$OD) δ (ppm): 8.96 (dd, J=1.7, 4.0 Hz, 1H), 8.85 (s, 1H), 8.56-8.53 (m, 2H), 8.42 (dd, J=2.3, 9.2 Hz, 1H), 8.27 (d, J=9.2 Hz, 1H), 7.66 (dd, J=4.3, 8.0 Hz, 1H), 7.18 (d, J=14.9 Hz, 1H), 6.49 (d, J=15.5 Hz, 1H), 5.63 (d, J=10.9 Hz, 1H), 4.68 (m, 1H), 4.21 (d, J=7.5 Hz, 1H), 3.91 (d, J=13.8 Hz, 1H), 3.86 (d, J=9.7 Hz, 1H), 3.59-3.53 (complex m, 2H), 3.47 (dd, J=3.4, 10.9 Hz, 1H), 3.36-3.30 (complex m, 2H), 3.20 (m, 1H), 3.12 (app t, J=9.5 Hz, 1H), 2.87-2.76 (complex m, 2H), 2.67 (m, 1H), 2.50 (s, 6H), 2.47-2.26 (complex m, 3H), 2.24 (s, 3H), 1.82 (s, 3H), 2.06 (d, J=16.6 Hz, 1H), 1.82-1.67 (complex m, 5H), 1.58-1.50 (complex m, 3H), 1.22 (app d, J=6.3 Hz, 6H), 1.02 (d, J=6.9 Hz, 3H), 0.89 (t, J=7.5 Hz, 3H). $^{13}$C NMR (125 MHz, CD$_3$OD) δ (ppm): 206.6, 174.3, 152.4, 149.6, 148.2, 146.5, 144.7, 138.8, 136.5, 136.4, 131.3, 129.9, 124.6, 123.9, 123.8, 120.4, 119.5, 105.7, 80.6, 76.1, 74.3, 72.6, 71.7 (2C), 68.4, 62.4, 55.8, 52.9, 48.2, 46.6, 43.1, 42.5, 42.2 (2C), 40.5, 35.0, 34.2, 26.2, 26.0, 18.2, 17.9, 13.2, 10.0, 9.7. HRMS (ESI) m/z: 821.4815 [M+H]$^+$, calcd for $C_{44}H_{65}N_6O_9$: 821.4813.

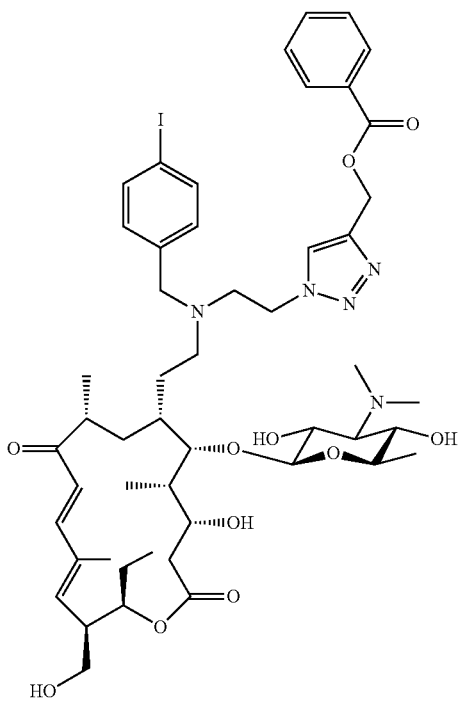
YT713

According to the general procedure (method B) for synthesis of triazole analogues, YT699 (100.0 mg, 0.133 mmol) with propargyl benzoate (24.6 μL, 0.170 mmol) was converted to YT713 (93.3 mg, 67%) as a pale yellow solid. HRMS (ESI) m/z: 1044.4190 [M+H]$^+$, calcd for $C_{50}H_{71}IN_5O_{11}$: 1044.4195.

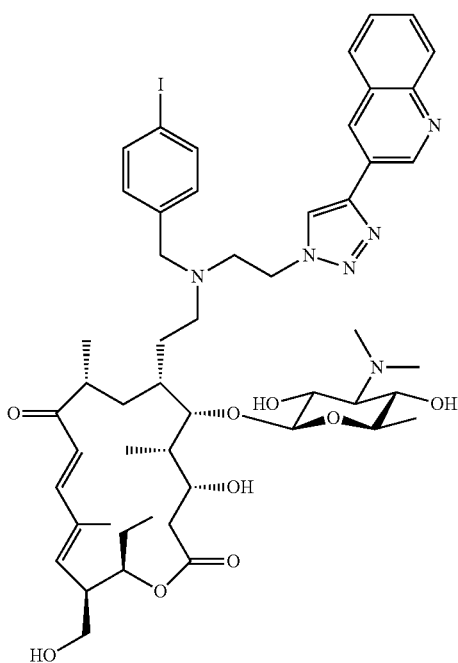
YT714

According to the general procedure (method A) for synthesis of triazole analogues, YT699 (100.0 mg, 0.113 mmol) with 3-ethynylquinoline (26.0 mg, 0.170 mmol) was converted to YT714 (64.8 mg, 56%) as a pale yellow solid. HRMS (ESI) m/z: 1037.4252 [M+H]$^+$, calcd for $C_{51}H_{70}IN_6O_9$: 1037.4249.

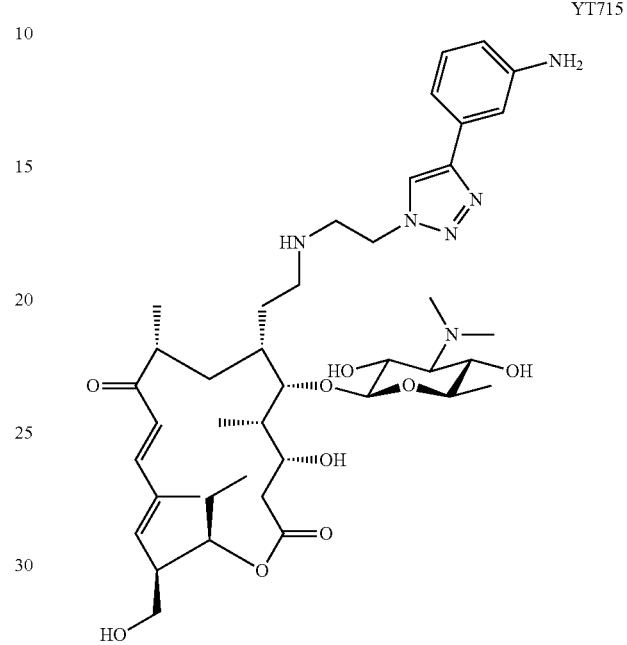
YT715

According to the general procedure (method B) for synthesis of triazole analogues, YT615 (100.0 mg, 0.150 mmol) with m-ethynyl aniline (35.1 mg, 0.299 mmol) was converted to YT715 (33.0 mg, 28%) as a pale yellow solid. HRMS (FAB, NBA matrix) m/z: 785.4808 [M+H]$^+$, calcd for $C_{41}H_{65}N_6O_9$: 785.4813.

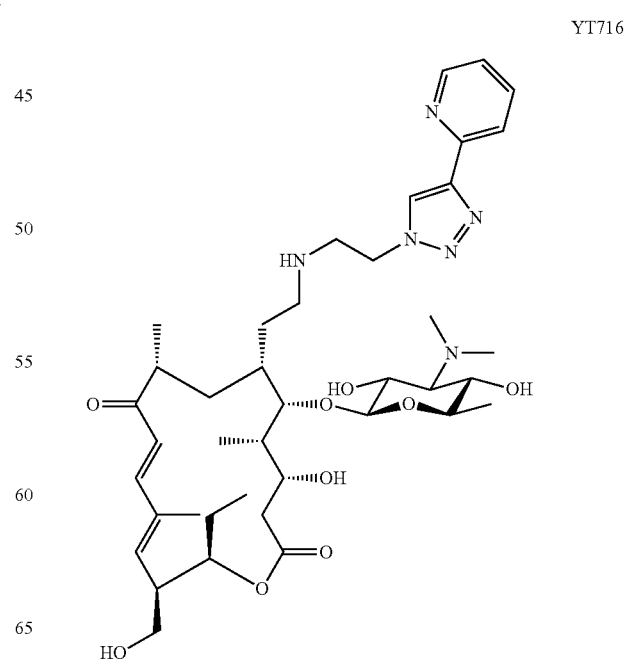
YT716

According to the general procedure (method A) for synthesis of triazole analogues, YT615 (100.0 mg, 0.150 mmol) with 2-ethynylpyridine (30.8 mg, 0.299 mmol) was converted to YT716 (50.9 mg, 44%) as a pale yellow solid. HRMS (FAB, NBA matrix) m/z: 771.4676 [M+H]$^+$, calcd for $C_{40}H_{63}N_6O_9$: 771.4657.

According to the general procedure (method A) for synthesis of triazole analogues, YT615 (100.0 mg, 0.150 mmol) with 1-ethynyl-2-nitrobenzene (44.0 mg, 0.299 mmol) was converted to YT718 (55.4 mg, 45%) as a pale yellow solid. HRMS (FAB, NBA matrix) m/z: 815.4567 [M+H]$^+$, calcd for $C_{41}H_{63}N_6O_{11}$: 815.4555.

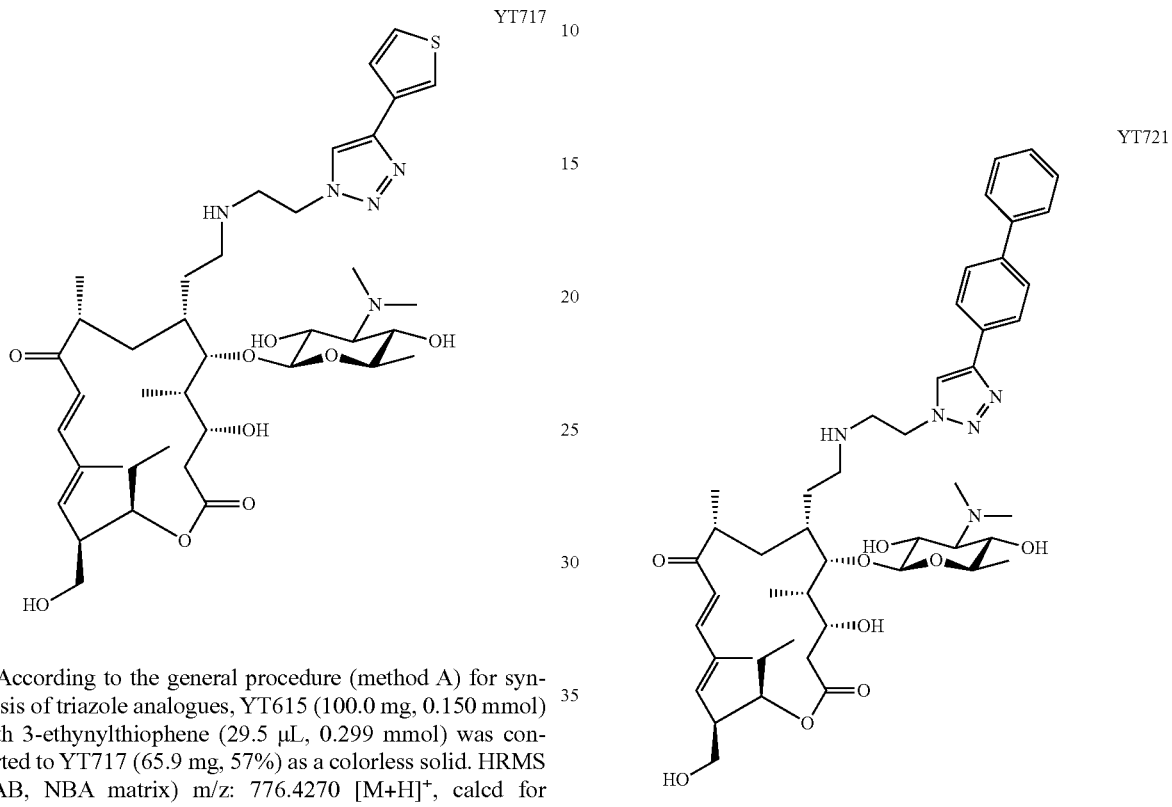

According to the general procedure (method A) for synthesis of triazole analogues, YT615 (100.0 mg, 0.150 mmol) with 3-ethynylthiophene (29.5 μL, 0.299 mmol) was converted to YT717 (65.9 mg, 57%) as a colorless solid. HRMS (FAB, NBA matrix) m/z: 776.4270 [M+H]$^+$, calcd for $C_{39}H_{62}N_5O_9S$: 776.4268.

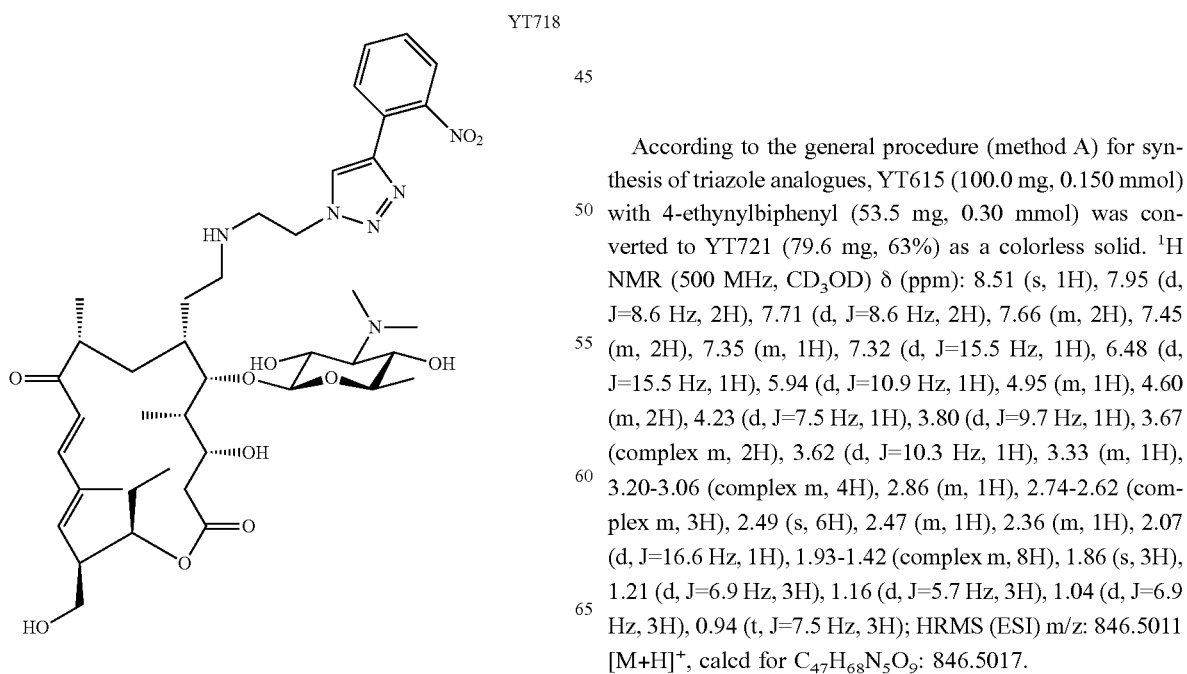

According to the general procedure (method A) for synthesis of triazole analogues, YT615 (100.0 mg, 0.150 mmol) with 4-ethynylbiphenyl (53.5 mg, 0.30 mmol) was converted to YT721 (79.6 mg, 63%) as a colorless solid. $^1$H NMR (500 MHz, CD$_3$OD) δ (ppm): 8.51 (s, 1H), 7.95 (d, J=8.6 Hz, 2H), 7.71 (d, J=8.6 Hz, 2H), 7.66 (m, 2H), 7.45 (m, 2H), 7.35 (m, 1H), 7.32 (d, J=15.5 Hz, 1H), 6.48 (d, J=15.5 Hz, 1H), 5.94 (d, J=10.9 Hz, 1H), 4.95 (m, 1H), 4.60 (m, 2H), 4.23 (d, J=7.5 Hz, 1H), 3.80 (d, J=9.7 Hz, 1H), 3.67 (complex m, 2H), 3.62 (d, J=10.3 Hz, 1H), 3.33 (m, 1H), 3.20-3.06 (complex m, 4H), 2.86 (m, 1H), 2.74-2.62 (complex m, 3H), 2.49 (s, 6H), 2.47 (m, 1H), 2.36 (m, 1H), 2.07 (d, J=16.6 Hz, 1H), 1.93-1.42 (complex m, 8H), 1.86 (s, 3H), 1.21 (d, J=6.9 Hz, 3H), 1.16 (d, J=5.7 Hz, 3H), 1.04 (d, J=6.9 Hz, 3H), 0.94 (t, J=7.5 Hz, 3H); HRMS (ESI) m/z: 846.5011 [M+H]$^+$, calcd for $C_{47}H_{68}N_5O_9$: 846.5017.

YT722

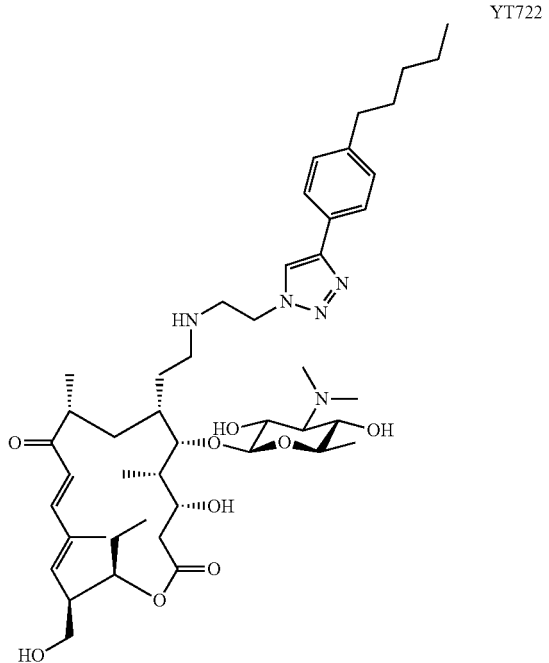

According to the general procedure (method B) for synthesis of triazole analogues, YT615 (100.0 mg, 0.150 mmol) with 1-ethynyl-4-pentylbenzene (51.5 mg, 0.299 mmol) was converted to YT722 (57.6 mg, 46%) as a colorless solid. HRMS (ESI) m/z: 840.5508 [M+H]$^+$, calcd for $C_{46}H_{74}N_5O_9$: 840.5487.

YT723

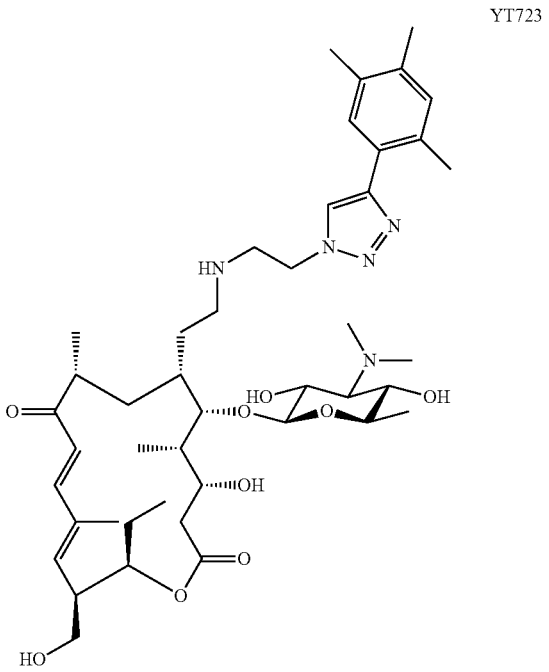

According to the general procedure (method B) for synthesis of triazole analogues, YT615 (36.0 mg, 0.054 mmol) with 1-ethynyl-2,4,5-trimethylbenzene (15.5 mg, 0.108 mmol) was converted to YT723 (31 mg, 71%) as a colorless solid. HRMS (ESI) m/z: 834.4984 [M+Na]$^+$, calcd for $C_{44}H_{69}N_5O_9Na$: 834.4993.

YT724

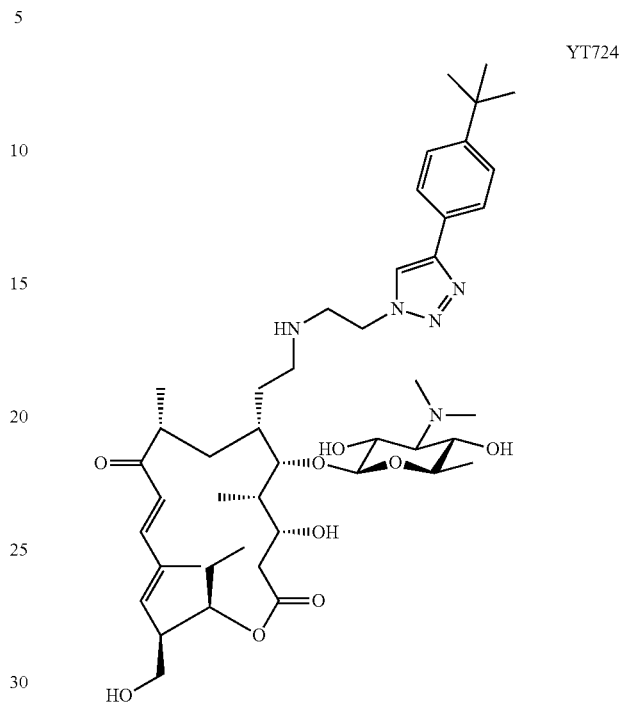

According to the general procedure (method B) for synthesis of triazole analogues, YT615 (100.0 mg, 0.150 mmol) with p-t-butylphenylacetylene (53.4 μL, 0.299 mmol) was converted to YT724 (70.5 mg, 57%) as a colorless solid. HRMS (FAB, NBA matrix) m/z: 826.5333 [M+H]$^+$, calcd for $C_{45}H_{72}N_5O_9$: 826.5330.

YT726

According to the general procedure (method A) for synthesis of triazole analogues, YT616 (20.0 mg, 0.0321 mmol) with 3-ethynylthiophene (4.7 μL, 0.0481 mmol) was converted to YT726 (18.8 mg, 80%) as a colorless solid. HRMS (ESI) m/z: 733.3838 [M+H]+, calcd for $C_{37}H_{57}N_4O_9S$: 733.3846.

verted to YT728 (67.7 mg, 73%) as a colorless solid. HRMS (ESI) m/z: 800.4222 [M+H]+, calcd for $C_{42}H_{59}N_5O_9Na$: 800.4211.

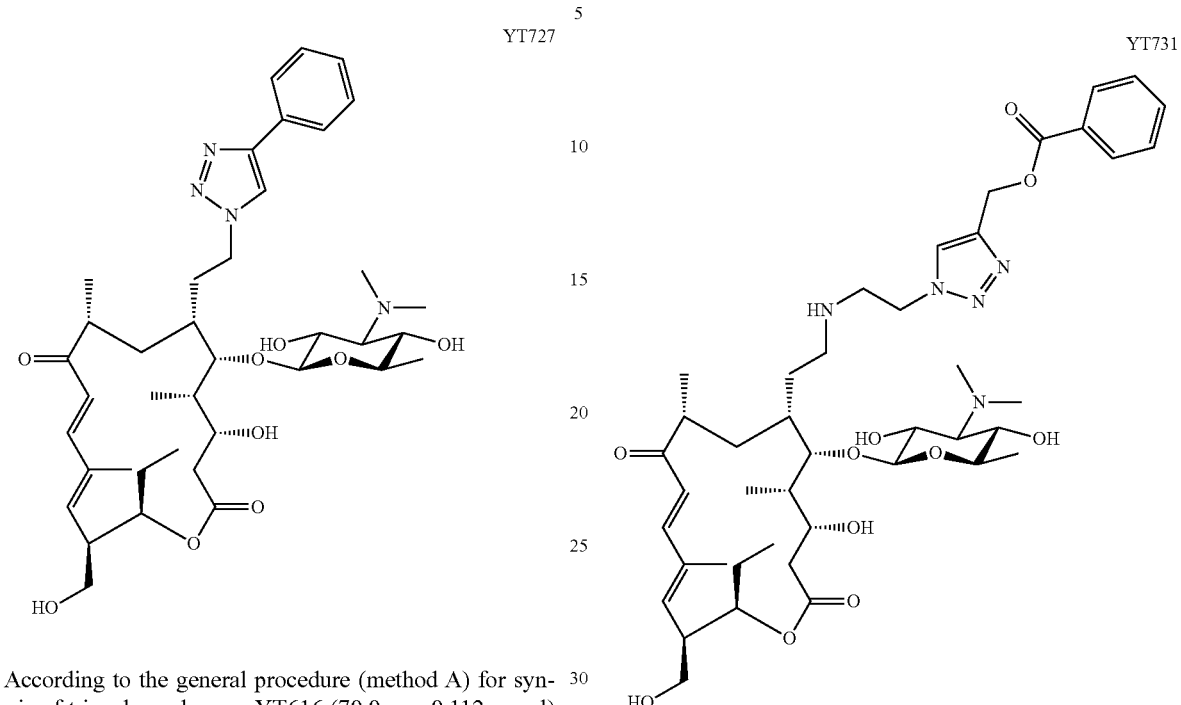

According to the general procedure (method A) for synthesis of triazole analogues, YT616 (70.0 mg, 0.112 mmol) with ethynylbenzene (18.5 µL, 0.168 mmol) was converted to YT727 (54.6 mg, 67%) as a colorless solid. HRMS (ESI) m/z: 749.4109 [M+Na]+, calcd for $C_{39}H_{58}N_4O_9Na$: 749.4102.

According to the general procedure (method B) for synthesis of triazole analogues, YT699 (100.0 mg, 0.150 mmol) with propargyl benzoate (47.9 mg, 0.299 mmol) was converted to YT731 (64.0 mg, 52%) as a colorless solid. HRMS (FAB, NBA matrix) m/z: 828.4774 [M+H]+, calcd for $C_{43}H_{66}N_5O_{11}$: 828.4779.

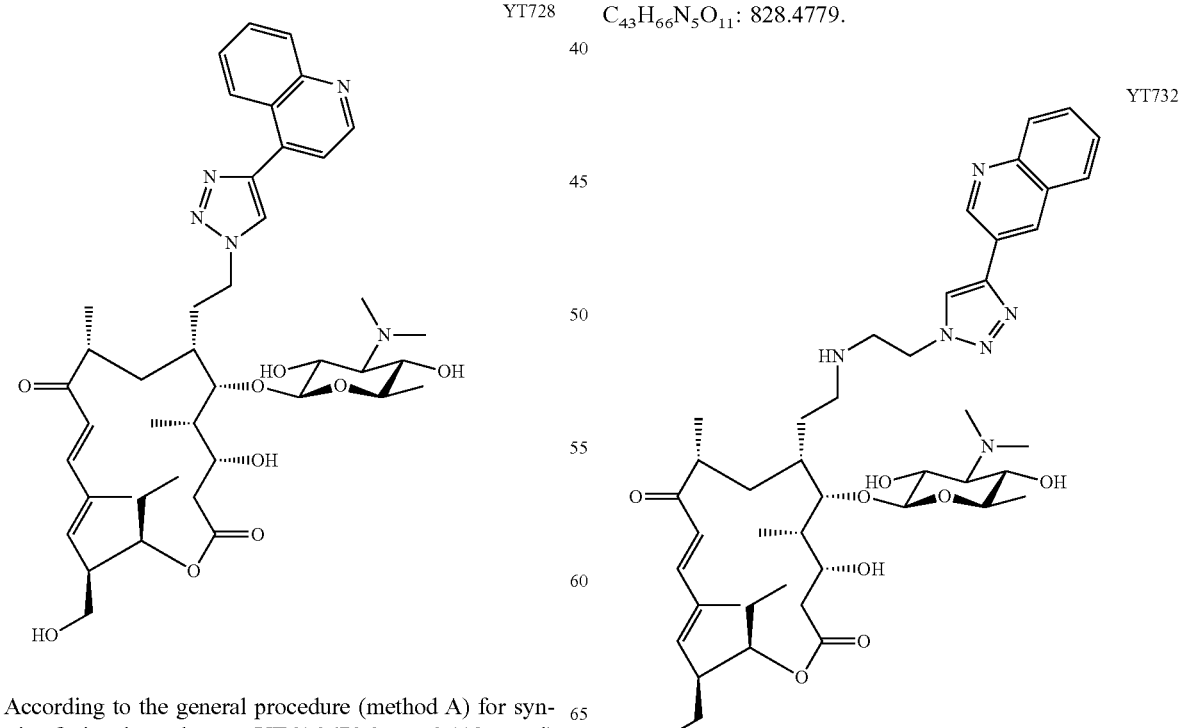

According to the general procedure (method A) for synthesis of triazole analogues, YT616 (70.0 mg, 0.112 mmol) with 4-ethynylquinoline (25.8 mg, 0.168 mmol) was con- According to the general procedure (method A) for synthesis of triazole analogues, YT615 (100.0 mg, 0.149 mmol) with 1-ethynyl-3-quinoline (45.8 mg, 0.299 mmol) was converted to YT732 (66.0 mg, 54%) as a colorless solid. $^1$H NMR (500 MHz, CD$_3$OD) δ (ppm): 9.39 (d, J=2.3 Hz, 1H), 8.81 (d, J=2.3 Hz, 1H), 8.75 (s, 1H), 8.06 (d, J=8.6 Hz, 1H), 8.02 (d, J=8.0 Hz, 1H), 7.79 (m, 1H), 7.65 (app. t, J=7.5 Hz, 1H), 7.28 (d, J=15.5 Hz, 1H), 6.47 (d, J=15.5 Hz, 1H), 5.92 (d, J=10.3 Hz, 1H), 4.92 (m, 1H), 4.65 (m, 2H), 4.23 (d, J=7.5 Hz, 1H), 3.79 (d, J=9.7 Hz, 1H), 3.65-3.61 (complex m, 3H), 3.33 (m, 1H), 3.23-3.08 (complex m, 4H), 2.85 (m, 1H), 2.75 (m, 1H), 2.69-2.63 (complex m, 2H), 2.50 (s, 6H), 2.48-2.35 (complex m, 2H), 2.06 (d, J=16.6 Hz, 1H), 1.91-1.43 (complex m, 8H), 1.85 (s, 3H), 1.21 (d, J=6.9 Hz, 3H), 1.18 (d, J=6.3 Hz, 3H), 1.03 (d, J=6.3 Hz, 3H), 0.93 (t, J=7.5 Hz, 3H); HRMS (ESI) m/z: 821.4808 [M+H]$^+$, calcd for C$_{44}$H$_{65}$N$_6$O$_9$: 821.4813.

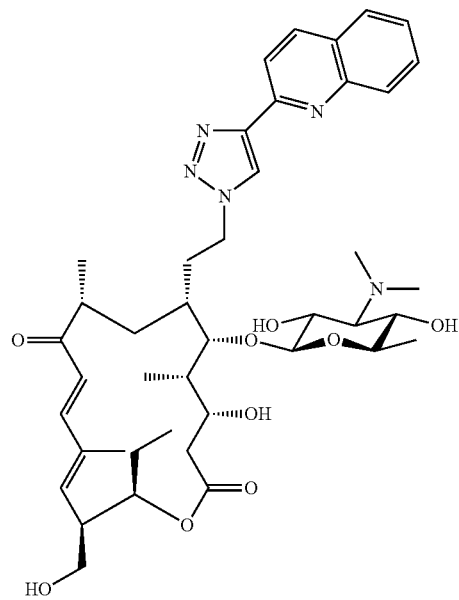

YT734

According to the general procedure (method A) for synthesis of triazole analogues, YT616 (77.0 mg, 0.123 mmol) with 2-ethynylquinoline (28.4 mg, 0.185 mmol) was converted to YT734 (90.2 mg, 94%) as a colorless solid. HRMS (ESI) m/z: 800.4221 [M+Na]$^+$, calcd for C$_{42}$H$_{59}$N$_5$O$_9$Na: 800.4211.

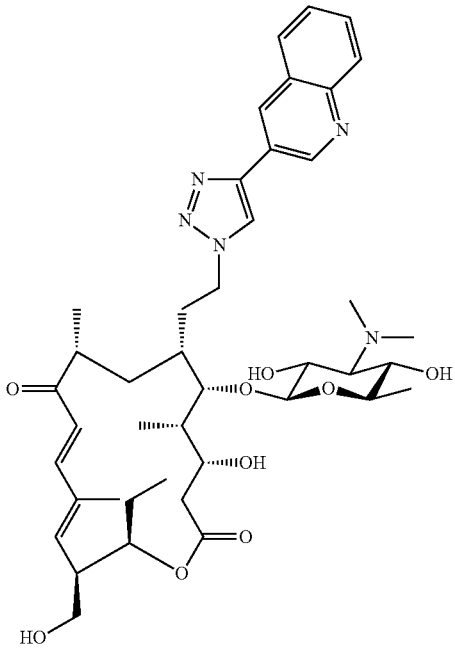

YT733

According to the general procedure (method A) for synthesis of triazole analogues, YT616 (70.0 mg, 0.112 mmol) with 3-ethynylquinoline (25.8 mg, 0.168 mmol) was converted to YT733 (55.1 mg, 58%) as a colorless solid. HRMS (ESI) m/z: 800.4220 [M+Na]$^+$, calcd for C$_{42}$H$_{59}$N$_5$O$_9$Na: 800.4211.

According to the general procedure (method A) for synthesis of triazole analogues, YT616 (66.6 mg, 0.107 mmol) with 4-ethynylpyridine (16.5 mg, 0.160 mmol) was converted to YT735 (52.4 mg, 68%) as a colorless solid. HRMS (ESI) m/z: 750.4058 [M+Na]$^+$, calcd for C$_{38}$H$_{57}$N$_5$O$_9$Na: 750.4054.

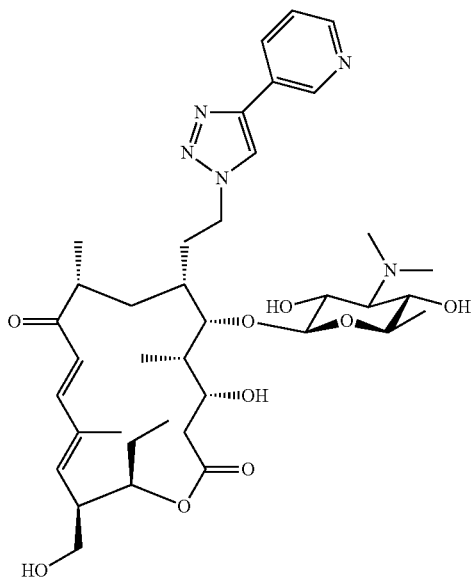

YT736

According to the general procedure (method A) for synthesis of triazole analogues, YT616 (70 mg, 0.112 mmol) with 3-ethynylpyridine (17.4 mg, 0.168 mmol) was converted to YT736 (61.2 mg, 69%) as a colorless solid. ¹³C NMR (125 MHz, CD₃OD) δ (ppm): 206.4, 175.6, 150.2, 150.0, 148.4, 146.0, 144.8, 137.3, 136.1, 129.6, 126.5, 123.7, 120.3, 105.8, 80.2, 79.3, 77.1, 75.1, 73.3, 72.5, 72.4, 68.8, 63.4, 50.0, 49.0, 47.0, 43.0 (2C), 41.5, 35.4, 34.3, 30.0, 27.0, 19.0, 18.4, 14.0, 10.8, 10.2.

YT737

According to the general procedure (method B) for synthesis of triazole analogues, YT711 (100.0 mg, 0.138 mmol) with 6-azidoquinoline (35.1 mg, 0.206 mmol) was converted to YT737 (92.5 mg, 75%) as a pale yellow solid. HRMS (ESI) m/z: 897.5116 [M+H]⁺, calcd for $C_{50}H_{69}N_6O_9$: 897.5126.

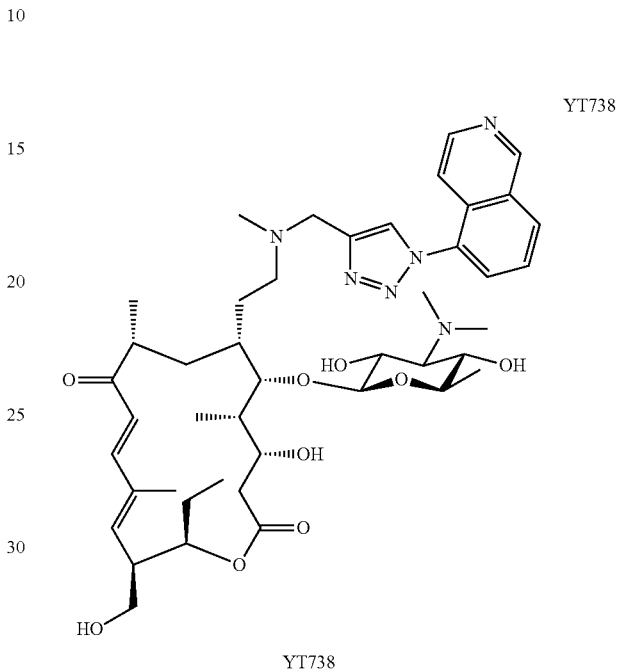

YT738

YT738

According to the general procedure (method B) for synthesis of triazole analogues, YT646 (100.0 mg, 0.154 mmol) with 5-azidoisoquinoline (39.1 mg, 0.230 mmol) was converted to YT738 (89.2 mg, 71%) as a pale yellow solid. ¹H NMR (500 MHz, CD₃OD) δ (ppm): 9.44 (d, J=1.2 Hz, 1H), 8.71 (s, 1H), 8.57 (d, J=6.3 Hz, 1H), 8.40 (d, J=8.6 Hz, 1H), 8.13 (dd, J=1.2, 7.5 Hz, 1H), 8.13 (t, J=7.7 Hz, 1H), 7.74 (d, J=5.7 Hz, 1H), 7.07 (d, J=15.5 Hz, 1H), 6.44 (d, J=15.5 Hz, 1H), 5.21 (d, J=10.3 Hz, 1H), 4.25 (d, J=7.5 Hz, 1H), 4.15 (m, 1H), 3.95 (dd, J=1.7, 9.7 Hz, 1H), 3.86 (d, J=13.8 Hz, 1H), 3.80 (d, J=10.3 Hz, 1H), 3.58-3.53 (m, 2H), 3.49 (dd, J=4.0, 10.9 Hz, 1H), 3.38-3.23 (complex m, 2H), 3.14 (app t, J=9.5 Hz, 1H), 2.86 (m, 1H), 2.74-2.63 (complex m, 2H), 2.51 (s, 6H), 2.42-2.28 (complex m, 3H), 2.25 (s, 3H), 1.97 (d, J=17.2 Hz, 1H), 1.91-1.42 (complex m, 8H), 1.76 (s, 3H), 1.26 (d, J=6.3 Hz, 3H), 1.21 (d, J=6.9 Hz, 3H), 0.99 (d, J=6.9 Hz, 3H), 0.74 (t, J=7.2 Hz, 3H). ¹³C NMR (125 MHz, CD₃OD) δ (ppm): 206.5, 173.9, 153.7, 149.6, 145.8, 145.0, 144.8, 136.2, 134.3, 132.7, 131.4, 130.5, 129.9, 128.6, 128.1, 119.2, 117.6, 105.7, 80.7, 76.1, 74.3, 72.6, 71.7 (2C), 68.3, 62.4, 56.1, 52.5, 48.3, 46.7, 43.0, 42.7, 42.2 (2C), 40.1, 35.0, 34.1, 26.2, 25.9, 18.3, 17.9, 13.1, 9.9, 9.6. HRMS (ESI) m/z: 821.4813 [M+H]$^+$, calcd for $C_{44}H_{65}N_6O_9$: 821.4813.

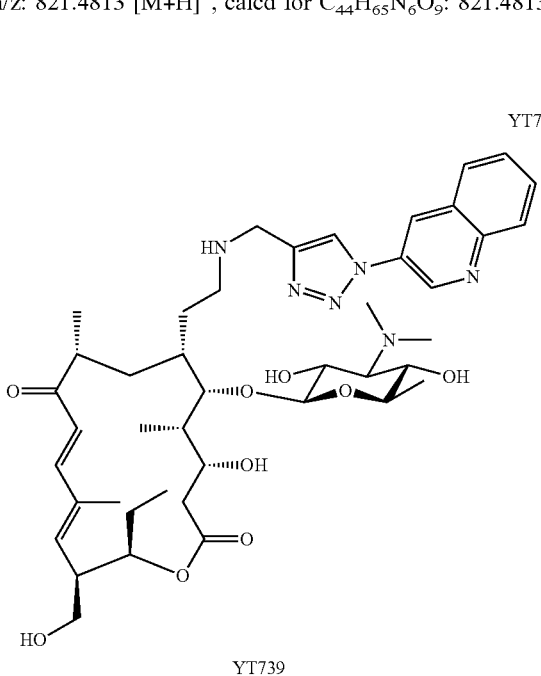

YT739

According to the general procedure (method B) for synthesis of triazole analogues, YT712 (100.0 mg, 0.157 mmol) with 3-azidoquinoline (40.1 mg, 0.236 mmol) was converted to YT739 (97.9 mg, 77%) as a colorless solid. $[\alpha]^{26}_D$ −111.2 (c 1.0, CHCl$_3$); $^1$H NMR (500 MHz, CD$_3$OD) δ (ppm): 9.48 (d, J=2.9 Hz, 1H), 8.89 (d, J=2.3 Hz, 1H), 8.82 (s, 1H), 8.16 (d, J=8.6 Hz, 1H), 8.13 (d, J=8.6 Hz, 1H), 7.88 (dt, J=1.2, 8.0 Hz, 1H), 7.74 (dt, J=1.2, 8.0 Hz, 1H), 7.23 (d, J=14.9 Hz, 1H), 6.48 (d, J=15.5 Hz, 1H), 5.70 (d, J=10.3 Hz, 1H), 4.63 (app t, J=8.6 Hz, 1H), 4.26 (d, J=7.5 Hz, 1H), 4.00 (d, J=14.3 Hz, 1H), 3.86 (d, J=13.8 Hz, 1H), 3.80 (d, J=10.3 Hz, 1H), 3.65 (d, J=10.3 Hz, 1H), 3.51 (dd, J=3.4, 11.2 Hz, 1H), 3.41-3.22 (complex m, 3H), 3.14 (t, J=9.2, 9.7 Hz, 1H), 2.92 (m, 1H), 2.83-2.73 (complex m, 2H), 2.66 (m, 1H), 2.51 (s, 6H), 2.45-2.38 (complex m, 2H), 2.04 (d, J=17.2 Hz, 1H), 1.89-1.66 (complex m, 5H), 1.82 (s, 3H), 1.60-1.45 (complex m, 3H), 1.24 (d, J=6.3 Hz, 3H), 1.22 (d, J=6.9 Hz, 3H), 1.03 (d, J=6.9 Hz, 3H), 0.84 (t, J=7.5 Hz, 3H). $^{13}$C NMR (125 MHz, CD$_3$OD) δ (ppm): 206.7, 174.6, 149.7, 148.4, 148.3, 144.8 (2C), 136.6, 132.2, 131.9, 129.8, 129.6, 129.4, 129.0, 128.4, 123.2, 119.6, 105.7, 80.6, 76.2, 74.3, 72.6, 71.73, 71.69, 68.3, 62.5, 48.3, 47.1, 46.6, 44.5, 42.8, 42.2 (2C), 40.4, 34.7, 34.1, 27.8, 26.1, 18.2, 17.9, 13.2, 10.0, 9.7. HRMS (ESI) m/z: 829.4478 [M+Na]$^+$, calcd for $C_{43}H_{62}N_6O_9Na$: 829.4476.

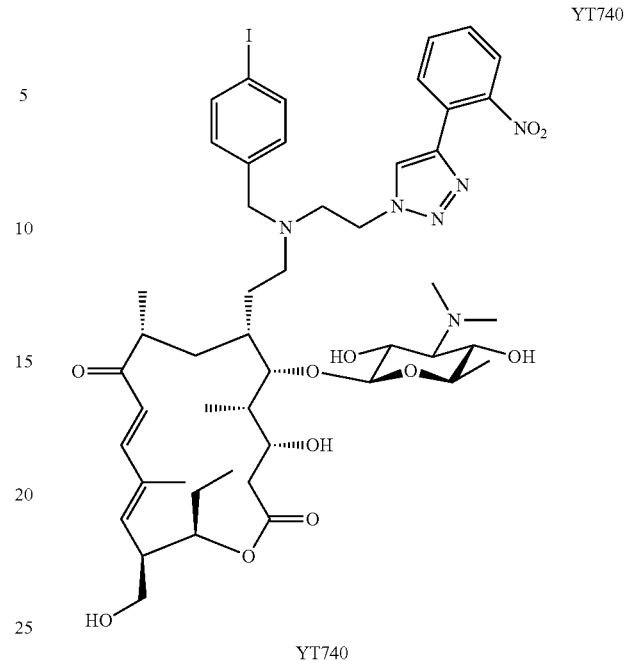

YT740

According to the general procedure (method A) for synthesis of triazole analogues, YT699 (100.0 mg, 0.113 mmol) with 1-ethynyl-2-nitrobenzene (33.3 mg, 0.226 mmol) was converted to YT740 (62.2 mg, 53%) as a colorless solid. HRMS (ESI) m/z: 1053.3832 [M+Na]$^+$, calcd for $C_{48}H_{67}IN_6O_{11}Na$: 1053.3810.

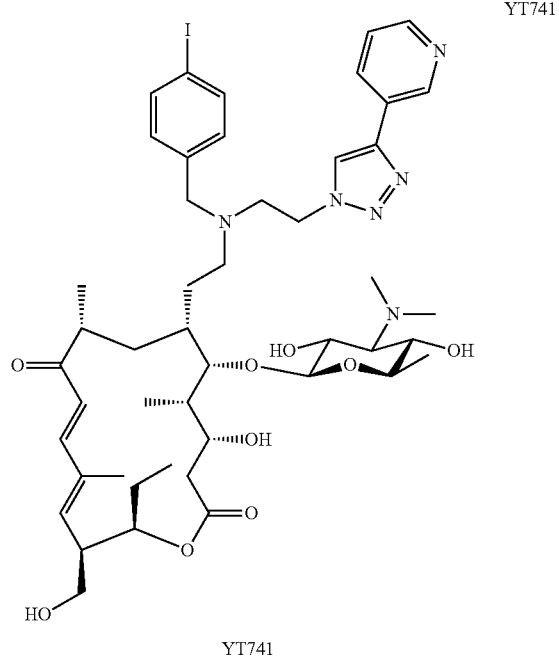

YT741

According to the general procedure (method A) for synthesis of triazole analogues, YT699 (100.0 mg, 0.113 mmol) with 3-ethynylpyridine (23.3 mg, 0.226 mmol) was converted to YT741 (71.7 mg, 64%) as a colorless solid. HRMS (ESI) m/z: 1009.3934 [M+H]$^+$, calcd for $C_{49}H_{66}IN_6O_9$: 1009.3936.

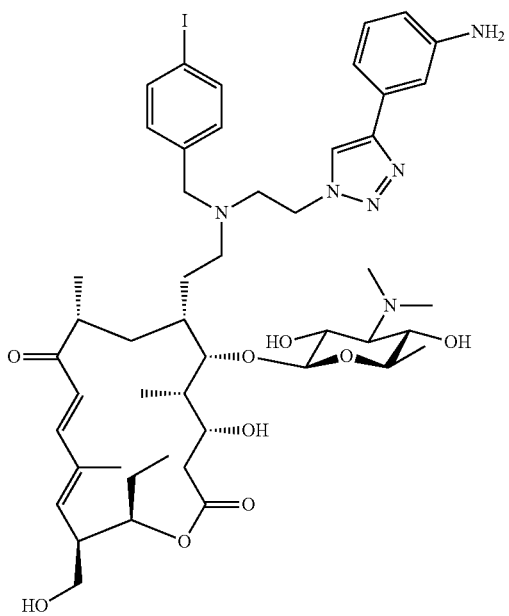

YT742

According to the general procedure (method A) for synthesis of triazole analogues, YT699 (100.0 mg, 0.113 mmol) with m-ethynylaniline (25.5 mL, 0.226 mmol) was converted to YT742 (75.6 mg, 67%) as a colorless solid. HRMS (ESI) m/z: 1023.4071 [M+Na]$^+$, calcd for $C_{48}H_{69}IN_6O_9Na$: 1023.4068.

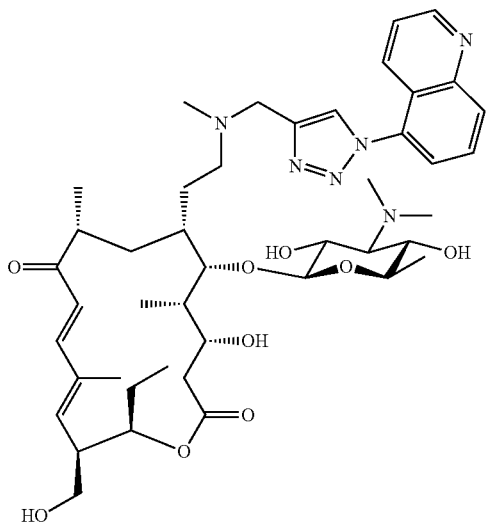

YT743

According to the general procedure (method B) for synthesis of triazole analogues, YT646 (100.0 mg, 0.154 mmol) with 5-azidoquinoline (39.1 mg, 0.230 mmol) was converted to YT743 (113.2 mg, 90%) as a pale yellow solid. $^1$H NMR (500 MHz, CD$_3$OD) δ (ppm): 9.00 (dd, J=1.7, 4.0 Hz, 1H), 8.69 (s, 1H), 8.30 (d, J=8.6 Hz, 1H), 8.25 (d, J=8.6 Hz, 1H), 8.02 (app t, J=8.0 Hz, 1H), 7.94 (d, J=7.5 Hz, 1H), 7.66 (dd, J=4.0, 8.6 Hz, 1H), 7.06 (d, J=15.5 Hz, 1H), 6.43 (d, J=15.5 Hz, 1H), 5.11 (d, J=10.3 Hz, 1H), 4.25 (d, J=7.5 Hz, 1H), 4.03 (m, 1H), 3.95 (d, J=13.8 Hz, 1H), 3.79 (dd, J=1.2, 9.7 Hz, 1H), 3.58-3.47 (complex m, 3H), 3.36 (dd, J=7.5, 10.9 Hz, 1H), 3.30-3.23 (complex m, 2H), 3.14 (app t, J=9.5 Hz, 1H), 2.86 (m, 1H), 2.72-2.62 (complex m, 2H), 2.51 (s, 6H), 2.41-2.26 (complex m, 3H), 2.25 (s, 3H), 1.95 (d, J=17.2 Hz, 1H), 1.92-1.40 (complex m, 8H), 1.75 (s, 3H), 1.26 (d, J=6.3 Hz, 3H), 1.20 (d, J=6.9 Hz, 3H), 0.99 (d, J=6.9 Hz, 3H), 0.76 (t, J=7.2 Hz, 3H). $^{13}$C NMR (125 MHz, CD$_3$OD) δ (ppm): 206.4, 173.8, 152.5, 149.6, 148.9, 145.7, 136.2, 135.2, 133.9, 131.7, 130.4, 128.2, 125.8, 125.5, 124.1, 119.1, 105.7, 80.7, 76.0, 74.3, 72.3, 72.6, 71.72, 71.65, 68.2, 62.3, 56.0, 52.4, 48.4, 46.7, 42.9, 42.8, 42.2 (2C), 40.1, 35.0, 34.0, 26.1, 28.9, 18.3, 17.9, 13.1, 10.0, 9.6. HRMS (ESI) m/z: 821.4814 [M+H]$^+$, calcd for $C_{44}H_{65}N_6O_9$: 821.4813.

YT744

According to the general procedure (method B) for synthesis of triazole analogues, YT646 (100.0 mg, 0.154 mmol) with 1-azidonaphthalene (39.1 mg, 0.230 mmol) was converted to YT744 (110 mg, 87%) as a pale yellow solid. $^1$H NMR (500 MHz, CD$_3$OD) δ (ppm): 8.62 (s, 1H), 8.15 (d, J=8.0 Hz, 1H), 8.07 (m, 1H), 7.76 (dd, J=1.2, 7.5 Hz, 1H), 7.70 (m, 1H), 7.66-7.58 (complex m, 3H), 7.09 (d, J=15.5 Hz, 1H), 6.43 (d, J=14.9 Hz, 1H), 5.06 (d, J=10.3 Hz, 1H), 4.25 (d, J=7.5 Hz, 1H), 4.15 (app t, J=8.6 Hz, 1H), 3.96 (dd, J=1.2, 9.7 Hz, 1H), 3.58 (d, J=10.3 Hz, 1H), 3.52 (d, J=13.8 Hz, 1H), 3.45 (dd, J=4.6, 10.9 Hz, 1H), 3.35 (dd, J=7.5, 10.3 Hz, 1H), 3.28-3.20 (complex m, 2H), 3.14 (app t, J=9.5 Hz, 1H), 2.87 (m, 1H), 2.72-2.63 (complex m, 2H), 2.51 (s, 6H), 2.41-2.26 (complex m, 3H), 2.25 (s, 3H), 1.95 (d, J=17.2 Hz, 1H), 1.91-1.38 (complex m, 8H), 1.74 (s, 3H), 1.26 (d, J=5.7 Hz, 3H), 1.20 (d, J=6.9 Hz, 3H), 0.99 (d, J=6.9 Hz, 3H), 0.76 (t, J=7.2 Hz, 3H). $^{13}$C NMR (125 MHz, CD$_3$OD) δ (ppm): 206.4, 173.7, 149.7, 145.4, 145.2, 136.2, 135.5, 135.3, 131.6, 130.1, 129.4, 129.0, 128.4, 128.3, 126.3, 125.4, 123.7, 119.0, 105.7, 80.7, 76.0, 74.3, 72.6, 71.74, 71.65, 68.3, 62.4, 56.0, 52.5, 48.4, 46.7, 42.9, 42.8, 42.2 (2C), 40.1, 35.0, 34.0, 26.2, 26.0, 18.3, 17.9, 13.1, 10.0, 9.6. HRMS (ESI) m/z: 820.4868 [M+H]$^+$, calcd for C$_{44}$H$_{66}$N$_5$O$_9$: 820.4861.

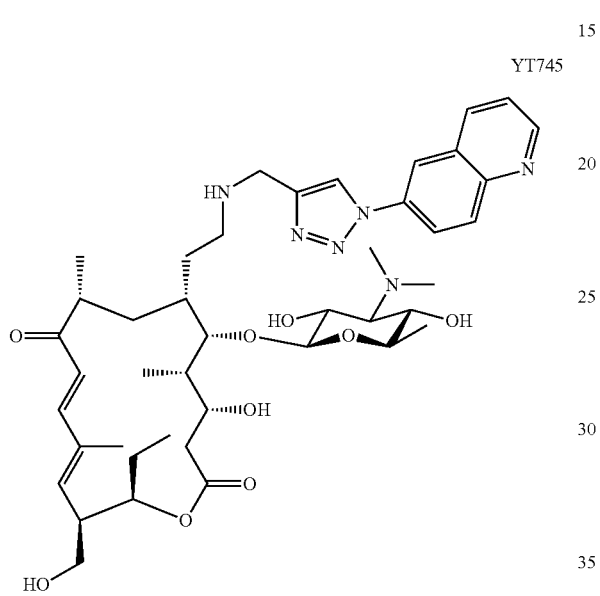

YT745

According to the general procedure (method B) for synthesis of triazole analogues, YT712 (100.0 mg, 0.157 mmol) with 6-azidonaphthalene (40.1 mg, 0.236 mmol) was converted to YT745 (100.2 mg, 79%) as a colorless solid. $^1$H NMR (500 MHz, CD$_3$OD) δ (ppm): 8.95 (dd, J=1.7, 8.0 Hz, 1H), 8.77 (s, 1H), 8.53 (m, 2H), 8.42 (dd, J=2.3, 9.2 Hz, 1H), 8.25 (d, J=9.2, 1H), 7.65 (dd, J=4.3, 8.3 Hz, 1H), 7.25 (d, J=15.5 Hz, 1H), 6.49 (d, J=15.5 Hz, 1H), 5.76 (d, J=10.3 Hz, 1H), 4.76 (m, 1H), 4.25 (d, J=7.5 Hz, 1H), 3.99 (d, J=13.8 Hz, 1H), 3.86 (d, J=13.8 Hz, 1H), 3.81 (d, J=9.7 Hz, 1H), 3.66 (dd, J=10.3 Hz, 1H), 3.53 (dd, J=3.4, 11.5 Hz, 1H), 3.46 (m, 1H), 3.35 (dd, J=8.0, 10.9 Hz, 1H), 3.23 (m, 1H), 3.13 (app t, J=9.5 Hz, 1H), 2.90 (m, 1H), 2.84-2.74 (complex m, 2H), 2.67 (m, 1H), 2.51 (s, 6H), 2.47-2.36 (complex m, 2H), 2.06 (d, J=17.2 Hz, 1H), 1.88-1.68 (complex m, 5H), 1.83 (s, 3H), 1.60-1.51 (complex m, 3H), 1.23 (d, J=6.3 Hz, 3H), 1.22 (d, J=6.9 Hz, 3H), 1.04 (d, J=6.9 Hz, 3H), 0.88 (t, J=7.5 Hz, 3H). $^{13}$C NMR (125 MHz, CD$_3$OD) δ (ppm): 206.4, 173.7, 149.7, 145.4, 145.2, 136.2, 135.5, 135.3, 131.6, 130.1, 129.4, 129.0, 128.4, 128.3, 126.3, 125.4, 123.7, 119.0, 105.7, 80.7, 76.0, 74.3, 72.6, 71.74, 71.65, 68.3, 62.4, 56.0, 52.5, 48.4, 46.7, 42.9, 42.8, 42.2 (2C), 40.1, 35.0, 34.0, 26.2, 26.0, 18.3, 17.9, 13.1, 10.0, 9.6. HRMS (ESI) m/z: 829.4480 [M+Na]$^+$, calcd for C$_{43}$H$_{62}$N$_6$O$_9$Na: 829.4476.

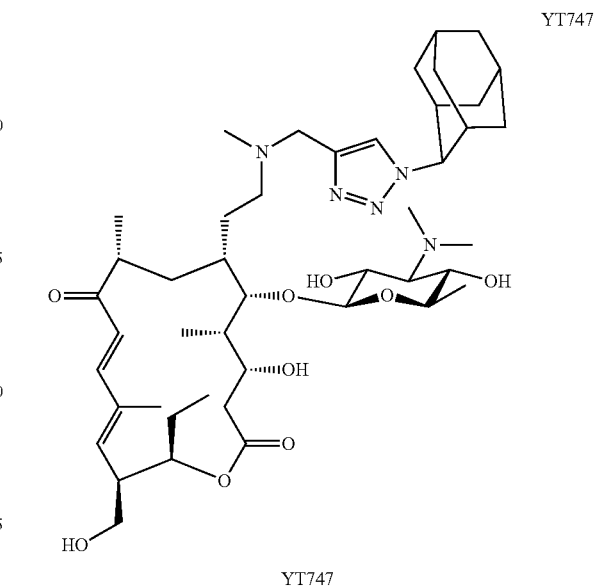

YT747

According to the general procedure (method B) for synthesis of triazole analogues, YT646 (100.0 mg, 0.154 mmol) with 1-azidoadamantane (40.9 mg, 0.230 mmol) was converted to YT747 (110.6 mg, 87%) as a colorless solid. HRMS (ESI) m/z: 828.5474 [M+H]$^+$, calcd for C$_{45}$H$_{74}$N$_5$O$_9$: 828.5487.

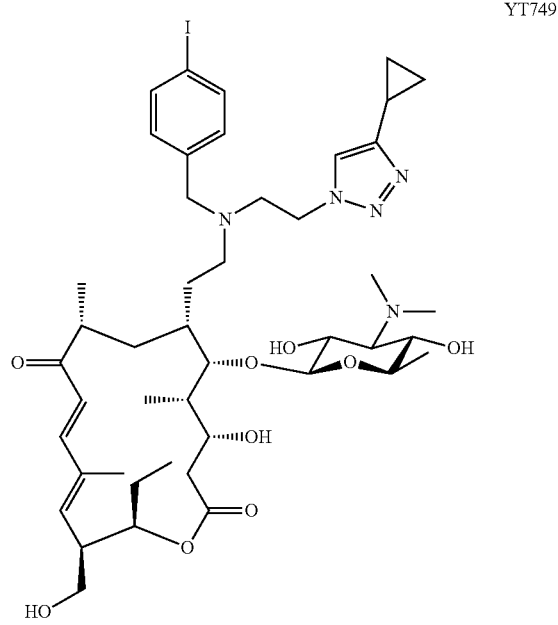

YT749

According to the general procedure (method A) for synthesis of triazole analogues, YT699 (80.0 mg, 0.0905 mmol) with cyclopropylacetylene (30.4 mg, 0.181 mmol) was converted to YT749 (54.4 mg, 63%) as a colorless solid. HRMS (ESI) m/z: 972.3968 [M+Na]$^+$, calcd for $C_{45}H_{68}IN_5O_9Na$: 972.3959.

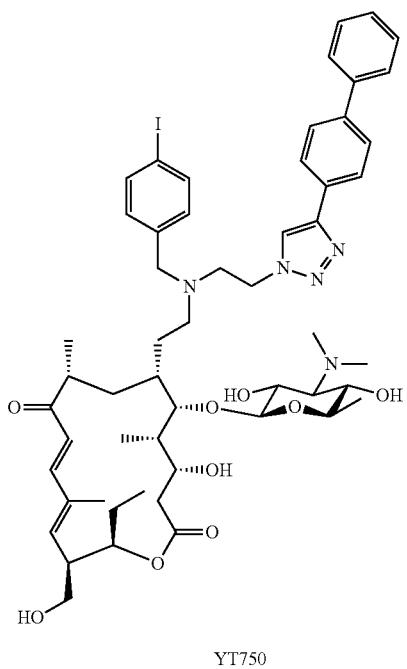

YT750

According to the general procedure (method A) for synthesis of triazole analogues, YT699 (80.0 mg, 0.0905 mmol) with 4-ethynylbiphenyl (32.3 mg, 0.181 mmol) was converted to YT750 (53.5 mg, 56%) as a colorless solid. HRMS (ESI) m/z: 1084.4274 [M+Na]$^+$, calcd for $C_{54}H_{72}IN_5O_9Na$: 1084.4272.

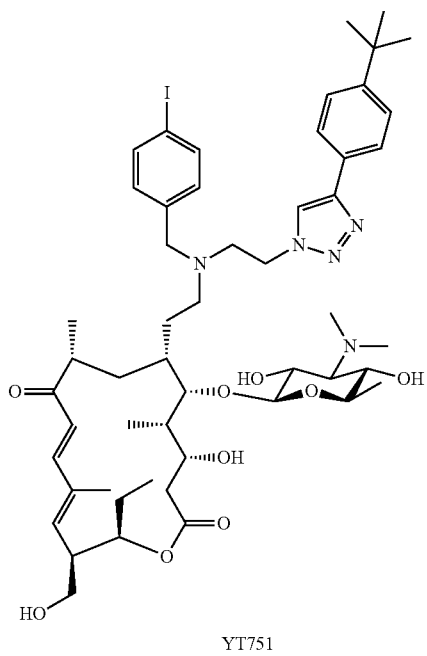

YT751

According to the general procedure (method A) for synthesis of triazole analogues, YT699 (100.0 mg, 0.113 mmol) with p-t-butylacetylene (40.0 µL, 0.225 mmol) was converted to YT751 (60.8 mg, 65%) as a pale yellow solid. HRMS (ESI) m/z: 1042.4772 [M+H]$^+$, calcd for $C_{52}H_{77}IN_5O_9$: 1042.4766.

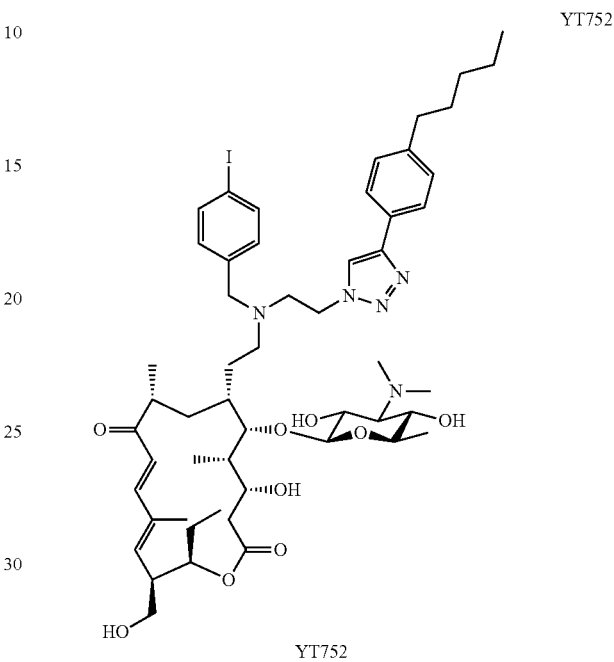

YT752

According to the general procedure (method A) for synthesis of triazole analogues, YT699 (100.0 mg, 0.113 mmol) with 1-ethynyl-4-n-pentylbenzene (44 µL, 0.227 mmol) was converted to YT752 (60.7 mg, 64%) as a pale yellow solid. HRMS (ESI) m/z: 1056.4936 [M+H]$^+$, calcd for $C_{53}H_{79}IN_5O_9$: 1056.4922.

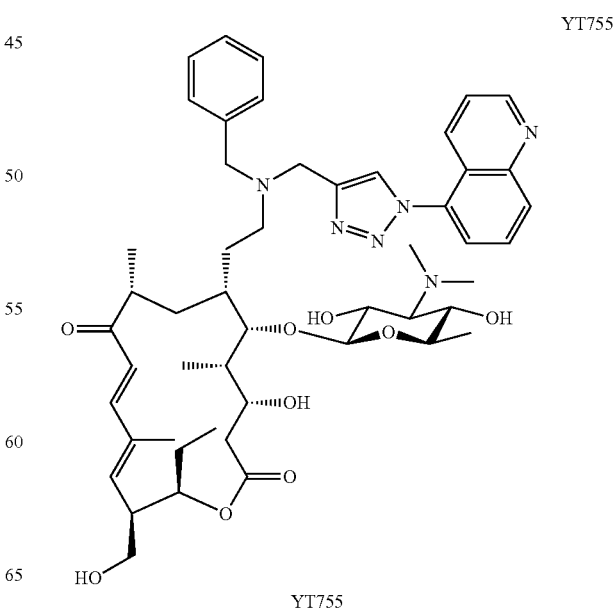

YT755

According to the general procedure (method B) for synthesis of triazole analogues, YT711 (100.0 mg, 0.138 mmol) with 5-azidoquinoline (30.4 mg, 0.179 mmol) was converted to YT755 (96.5 mg, 78%) as a colorless solid. HRMS (ESI) m/z: 897.5115 [M+H]$^+$, calcd for $C_{50}H_{69}N_6O_9$: 897.5126.

According to the general procedure (method B) for synthesis of triazole analogues, YT711 (100.0 mg, 0.138 mmol) with 1-azidonaphthalene (30.4 mg, 0.179 mmol) was converted to YT757 (110.2 mg, 89%) as a pale yellow solid. HRMS (ESI) m/z: 896.5176 [M+H]$^+$, calcd for $C_{51}H_{70}N_5O_9Na$: 896.5174.

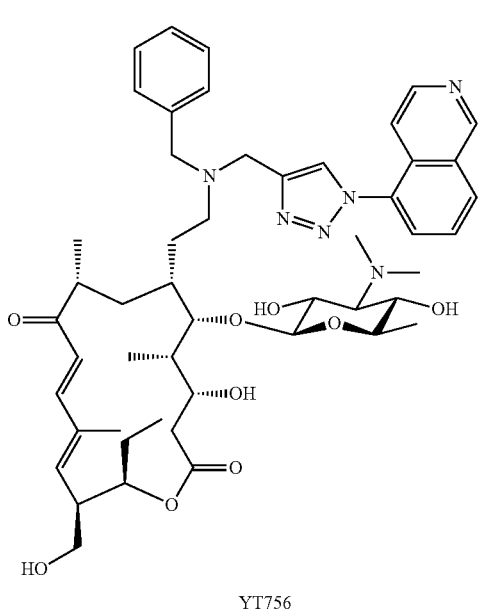

YT756

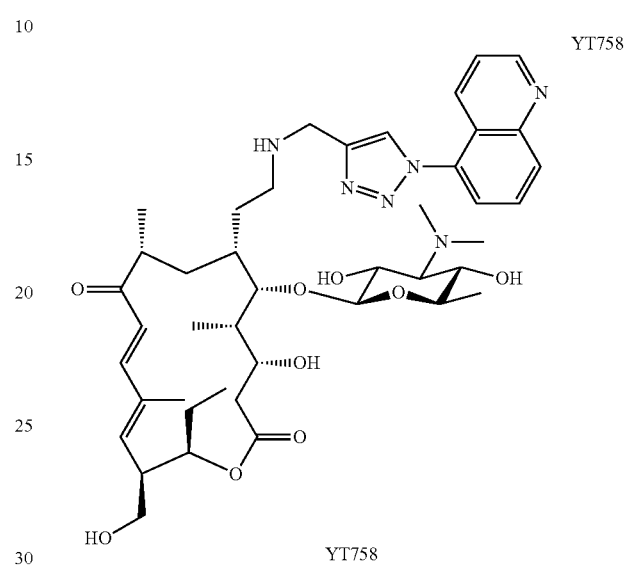

YT758

According to the general procedure (method B) for synthesis of triazole analogues, YT711 (100.0 mg, 0.138 mmol) with 5-azidoisoquinoline (30.4 mg, 0.179 mmol) was converted to YT756 (75.1 mg, 61%) as a pale yellow solid. HRMS (ESI) m/z: 897.5121 [M+H]$^+$, calcd for $C_{50}H_{69}N_6O_9$: 897.5126.

According to the general procedure (method B) for synthesis of triazole analogues, YT712 (100.0 mg, 0.157 mmol) with 5-azidoquinoline (40.1 mg, 0.236 mmol) was converted to YT758 (88.2 mg, 70%) as a pale brown solid. HRMS (ESI) m/z: 829.4479 [M+Na]$^+$, calcd for $C_{43}H_{62}N_6O_9Na$: 829.4476.

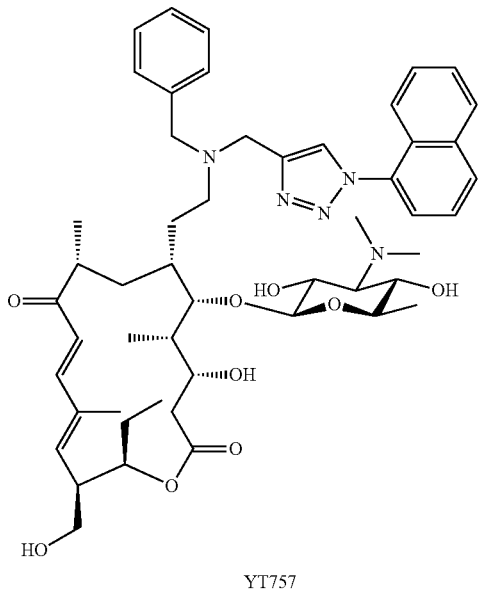

YT757

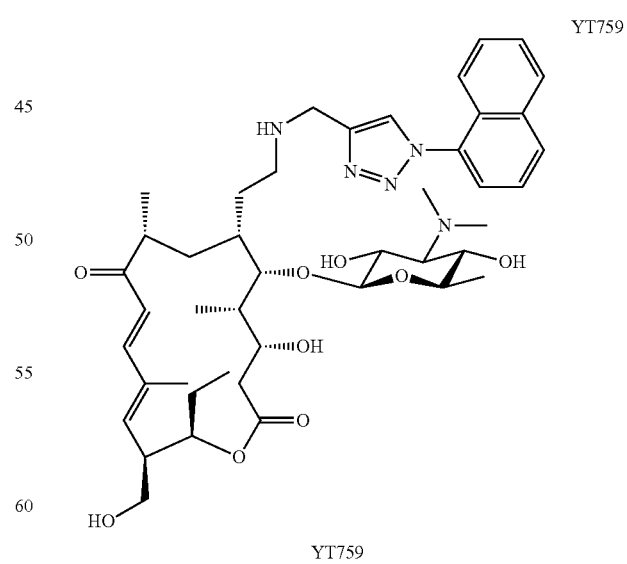

YT759

According to the general procedure (method B) for synthesis of triazole analogues, YT712 (100.0 mg, 0.157 mmol) with 1-azidonaphthalene (40.1 mg, 0.236 mmol) was converted to YT759 (97.3 mg, 77%) as a pale yellow solid. HRMS (ESI) m/z: 828.4515 [M+Na]+, calcd for $C_{44}H_{63}N_5O_9Na$: 828.4524.

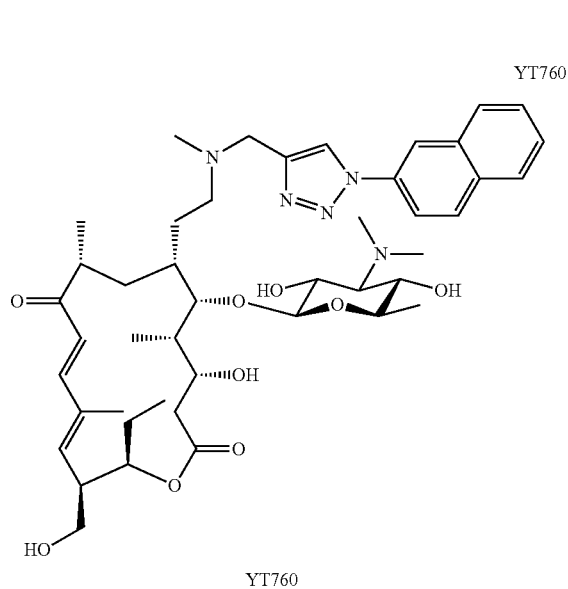

YT760

According to the general procedure (method B) for synthesis of triazole analogues, YT646 (100.0 mg, 0.154 mmol) with 2-azidonaphthalene (34.5 mg, 0.204 mmol) was converted to YT760 (95.0 mg, 76%) as a colorless solid. HRMS (ESI) m/z: 820.4858 [M+H]+, calcd for $C_{45}H_{66}N_5O_9$: 820.4861.

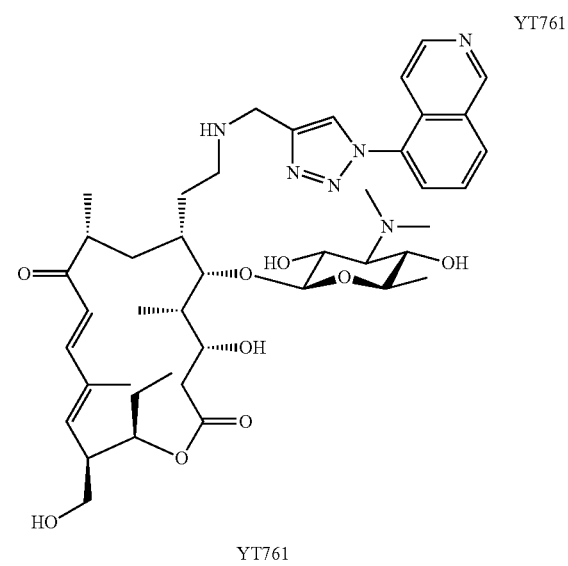

YT761

According to the general procedure (method B) for synthesis of triazole analogues, YT712 (100.0 mg, 0.157 mmol) with 5-azidoisoquinoline (40.1 mg, 0.236 mmol) was converted to YT761 (87.8 mg, 69%) as a pale yellow solid. HRMS (ESI) m/z: 807.4652 [M+H]+, calcd for $C_{43}H_{63}N_6O_9$: 807.4657.

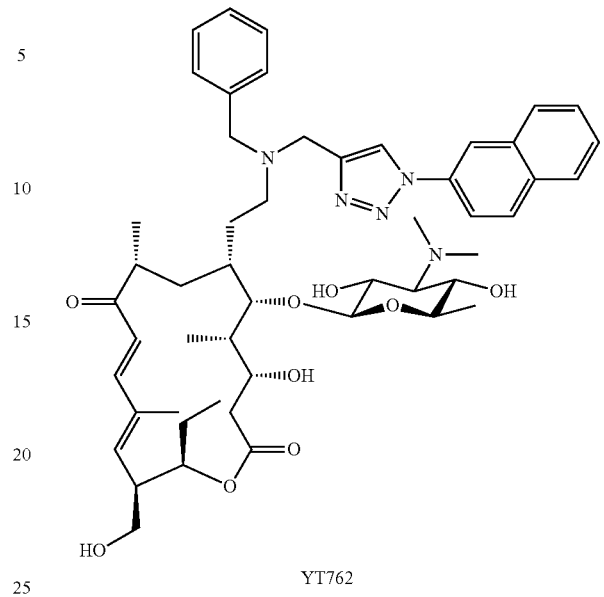

YT762

According to the general procedure (method B) for synthesis of triazole analogues, YT711 (100.0 mg, 0.138 mmol) with 2-azidonaphthalene (30.4 mg, 0.179 mmol) using was converted to YT762 (120.0 mg, 97%) as a pale brown solid. $^{13}$C NMR (125 MHz, CD$_3$OD) δ (ppm): 206.7, 174.6, 149.4, 147.2, 147.2, 144.3, 139.7, 135.8, 134.6, 134.3, 131.0, 130.7 (2C), 129.6, (2C), 129.5, 129.0, 128.4, 128.15, 128.06, 123.7, 120.1, 119.6 (2C), 105.5, 80.2, 76.2, 74.1, 72.5, 71.6 (2C), 68.6, 62.5, 59.7, 52.1, 50.6, 48.2, 46.5, 42.8, 42.1 (2C), 40.5, 34.8, 34.0, 26.3, 26.1, 18.1, 17.9, 13.4, 10.1, 9.9. HRMS (ESI) m/z: 896.5177 [M+H]+, calcd for $C_{51}H_{70}N_5O_9$: 896.5174.

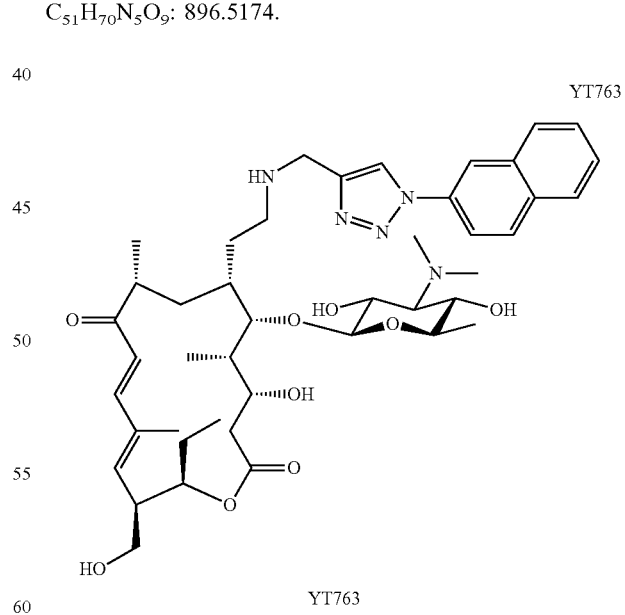

YT763

According to the general procedure (method B) for synthesis of triazole analogues, YT712 (100.0 mg, 0.157 mmol) with 2-azidonaphthalene (34.5 mg, 0.204 mmol) was converted to YT763 (92.1 mg, 73%) as a pale brown solid. HRMS (ESI) m/z: 806.4704 [M+H]+, calcd for $C_{44}H_{64}N_5O_9$: 806.4704.

Synthesis of Amine Analogues at C23 Position

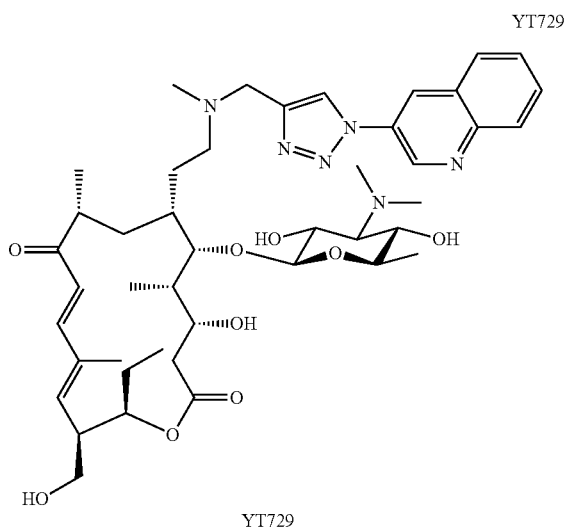

YT729

To a solution of YT650 (300 mg, 0.365 mmol) in anhydrous pyridine (5.3 mL) was added DPPA (94.3 µL, 0.438 mmol) and DBU (65.5 µL, 0.438 mmol) at 0° C. and the reaction mixture was stirred at 0° C. for 2 hr. Then DPPA (175 □µL, 0.814 mmol) and DBU (109 µL, 0.718 mmol) were added again to the reaction mixture and the reaction was further performed at 80° C. for 4 hr. The reaction was quenched with saturated NaHCO₃ aq. (2 mL), the reaction mixture was concentrated under reduced pressure. The residue was added CHCl₃ (8 mL) and washed with saturated NaHCO₃aq. The organic layer was dried over Na₂SO₄, and concentrated in vacuo. The crude product was used for the next step without further purification. To the solution of the crude product (182 mg, 0.173 mmol) in anhydrous DMF (1.9 mL) was added NaN₃ (33.7 mg, 0.519 mmol), and the reaction mixture was stirred at 80° C. for 22 hr. The solution was extracted with Hexane/EtOAc (v/v 1/1, 5 mL×2), and washed with H₂O (15 mL). The organic layer was dried over Na₂SO₄ and concentrated in vacuo. The residue was purified by flash column chromatography on silica gel (CHCl₃/MeOH/NH₃, 60/1/0.15) to give YT729 (115 mg, 79%) as a colorless solid. HRMS (ESI) m/z: 846.4877 [M+H]⁺, calcd for $C_{44}H_{64}N_9O_8$: 846.4878.

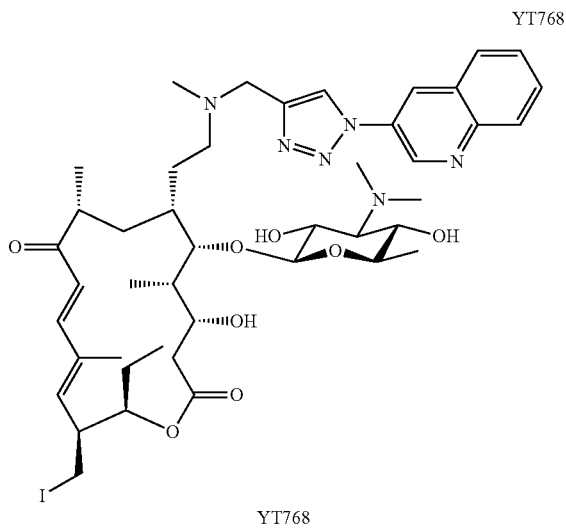

YT768

To a solution of YT650 (300 mg, 0.365 mmol) and PPh₃ (288 mg, 1.10 mmol) in anhydrous pyridine (5.3 mL) was added iodine (186 mg, 0.731 mmol) in anhydrous pyridine (2 mL), and the reaction mixture was stirred at 0° C. for 2 hr. The reaction was quenched with MeOH (0.2 mL), added toluene (15 mL) and concentrated in vacuo. The residue was added CHCl₃ (8 mL) and washed with saturated NaS₂O₃aq. The organic layer was dried over Na₂SO₄, and concentrated in vacuo. The residue was purified by flash column chromatography on silica gel (CHCl₃/MeOH/NH₃, 70/1/0.15) to give compound YT768 (290 mg, 85%) as a colorless solid. ¹H NMR (500 MHz, CD₃OD) d (ppm): 9.49 (d, J=2.3 Hz, 1H), 8.91 (d, J=1.7 Hz, 1H), 8.89 (s, 1H), 8.18 (d, J=8.6 Hz, 1H), 8.14 (d, J=8.6 Hz, 1H), 7.90 (m, 1H), 7.76 (t, J=8.0 Hz, 1H), 7.05 (d, J=15.5 Hz, 1H), 6.49 (d, J=14.9 Hz, 1H), 5.10 (d, J=10.3 Hz, 1H), 4.32 (m, 1H), 4.25 (d, J=7.5 Hz, 1H), 3.92 (d, J=14.3 Hz, 1H), 3.81 (dd, J=1.2, 9.7 Hz, 1H), 3.58 (d, J=10.7 Hz, 1H), 3.51 (d, J=13.8 Hz, 1H), 3.35 (dd, J=7.5, 10.3 Hz, 1H), 3.29-3.22 (complex m, 2H), 3.14 (t, J=9.5, 1H), 3.09 (dd, J=3.2, 10.0 Hz, 1H), 2.84 (m, 1H), 2.74 (m, 1H), 2.67 (m, 1H), 2.50 (s, 6H), 2.44-2.30 (complex m, 3H), 2.25 (s, 3H), 2.02 (d, J=16.6 Hz, 1H), 1.90-1.77 (complex m, 3H), 1.77 (s, 3H), 1.70-1.62 (complex m, 2H), 1.58-1.41 (complex m, 3H), 1.24 (d, J=6.3 Hz, 3H), 1.22 (d, J=6.9 Hz, 3H), 1.02 (d, J=6.3 Hz, 3H), 0.85 (t, J=7.2 Hz, 3H). ¹³C NMR (125 MHz, CD₃OD) d (ppm): 206.3, 174.1, 148.9, 148.4, 147.2, 146.9, 145.4, 145.3, 136.7, 132.3, 132.1, 129.9, 129.8, 129.5, 129.3, 129.0, 124.3, 120.0, 105.7, 80.7, 77.8, 74.3, 72.6, 71.72, 71.66, 68.3, 56.0, 47.2, 46.6, 43.0, 42.9, 42.2 (2C), 40.3, 34.9, 34.1, 26.2, 25.4, 18.3, 17.8, 13.2, 9.8, 9.7, 5.1. HRMS (ESI) m/z: 931.3828 [M+H]⁺, calcd for $C_{44}H_{64}IN_6O_8$: 931.3830.

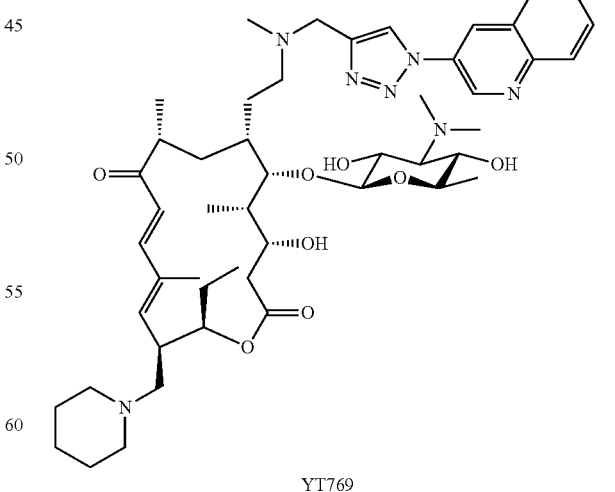

YT769

To a solution of YT768 (20.0 mg, 21.5 µmol) in anhydrous acetonitrile (0.3 mL) was added piperidine (21.5 µL, 0.215 mmol). The mixture was heated in a microwave reactor at 120° C. for 1.5 hours. Then piperidine (42.0 µL, 0.430 mmol) was added again to the reaction mixture and the reaction was further performed in a microwave reactor at 80° C. for 1 hour. The reaction mixture was concentrated in vacuo, and the residue was purified by flash column chromatography on silica gel (CHCl$_3$/MeOH/NH$_3$, 60/1/0.15) to give compound YT769 (17.0 mg, 89%) as a pale yellow solid. HRMS (FAB, NBA matrix) m/z: 888.5588 [M+H]$^+$, calcd for C$_{49}$H$_{74}$N$_7$O$_8$: 888.5599.

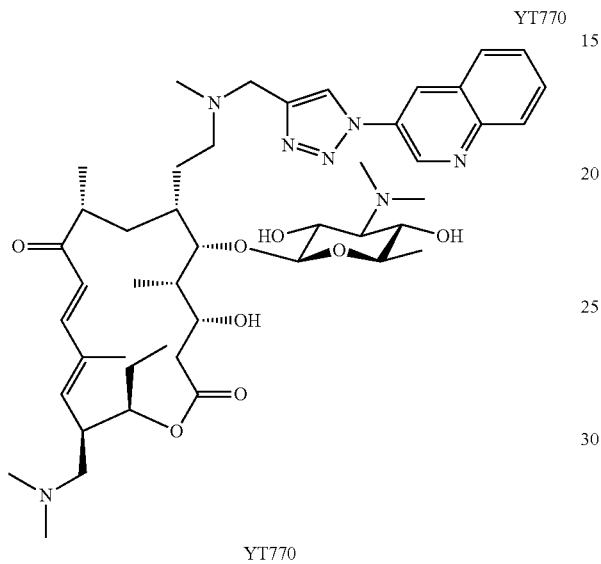

YT770

To a solution of YT768 (80.0 mg, 85.9 µmol) in anhydrous acetonitrile (1.1 mL) was added dimethylamine (40 wt % in water, 0.8 mL). The mixture was heated in a microwave reactor at 80° C. for 1 hour. The solvent mixture was concentrated in vacuo, and the residue was purified by flash column chromatography on silica gel (CHCl$_3$/MeOH/NH$_3$, 60/1/0.15) to give YT770 (69.2 mg, 95%) as a pale yellow solid. $^1$H NMR (500 MHz, CD$_3$OD) d (ppm): 9.51 (d, J=2.9 Hz, 1H), 8.91 (d, J=2.3 Hz, 1H), 8.19 (d, J=8.6 Hz, 1H), 8.14 (d, J=8.0 Hz, 1H), 7.91 (m, 1H), 7.77 (m, 1H), 7.03 (d, J=14.9 Hz, 1H), 6.44 (d, J=15.5 Hz, 1H), 5.12 (d, J=10.3 Hz, 1H), 4.26 (d, J=7.5 Hz, 1H), 4.19 (m, 1H), 3.97 (d, J=14.3 Hz, 1H), 3.85 (m, 1H), 3.60 (d, J=10.3 Hz, 1H), 3.43 (d, J=14.3 Hz, 1H), 3.36 (dd, J=7.5, 10.3 Hz, 1H), 3.26 (m, 1H), 3.26 (m, 1H), 3.15 (d, J=9.5 Hz, 1H), 2.89 (m, 1H), 2.78-2.62 (complex m, 2H), 2.52 (s, 6H), 2.45-2.39 (complex m, 2H), 2.31 (m, 1H), 2.25 (s, 3H), 2.06-2.02 (m, 1H), 2.02 (s, 6H), 1.94-1.74 (complex m, 4H), 1.78 (s, 3H), 1.73-1.66 (complex m, 2H), 1.63-1.40 (complex m, 3H), 1.25 (d, J=6.3 Hz, 3H), 1.20 (d, J=6.9 Hz, 3H), 1.02 (d, J=6.3 Hz, 3H), 0.84 (t, J=7.5 Hz, 3H). $^{13}$C NMR (125 MHz, CD$_3$OD) d (ppm): 206.2, 174.3, 149.3, 148.6, 147.2, 146.1, 145.7, 135.9, 132.3, 132.1, 130.0, 129.9, 129.5 (2C), 129.0, 124.1, 119.3, 105.7, 80.5, 76.9, 74.3, 72.6, 71.73, 71.70, 68.4, 61.1, 56.1, 52.4, 46.7, 45.8 (2C), 44.0, 43.2, 43.0, 42.2 (2C), 40.2, 34.8, 33.8, 26.2, 26.1, 18.2, 17.8, 13.1, 9.8, 9.7. HRMS (FAB, NBA matrix) m/z: 848.5277 [M+H]$^+$, Calcd for C$_{46}$H$_{70}$N$_7$O$_8$: 848.5286.

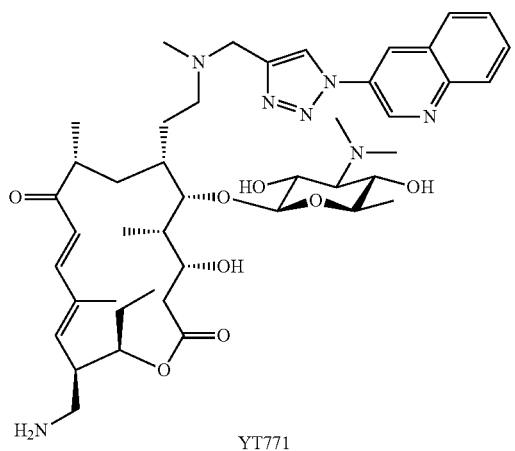

YT771

To a solution of YT729 (90.0 mg, 0.106 mmol) in THF/H$_2$O (1.2/0.12 mL) was added PPh$_3$ (94.4 mg, 0.361 mmol), and the reaction mixture was stirred at room temperature for 25 hr. The reaction mixture was concentrated in vacuo and the residue was extracted with CHCl$_3$ (5 mL×2). The organic layers were washed with brine (3 mL×1), and dried over Na$_2$SO$_4$, and concentrated in vacuo. The residue was purified by flash column chromatography on silica gel (CHCl$_3$/MeOH/NH$_3$, 60/1/0.15) to give compound YT771 (57.0 mg, 65%) as a colorless solid. HRMS (FAB, NBA matrix) m/z: 820.4973 [M+H]$^+$, calcd for C$_{44}$H$_{66}$N$_7$O$_8$: 820.4973.

Paper Disc Assays (1) Antibacterial activities against *Mannheimia* and *Pasteurella* were determined by the following steps:

1) *M. hemolytica* KB345 (Tilmicosin-sensitivity strain) and *M. hemolytica* KB346 (Tilmicosin-low sensitivity strain) were provided. KB 345 strain stored at −80° C. was seeded to BHIB agar medium (10 mL) by using Microbank beads (Pro-Lab) and platinum nail. After statically incubating the KB 345 strain for 24 hours at 37° C., it was seeded to maintaining slant BHIB agar medium (7 mL) by using platinum loop, further statically incubated for 24 hours at 37° C. to obtain slant. One platinum loop of KB 345 strain stored at the slant was inoculated into a large test tube charged with BHIB liquid medium (10 mL) and then incubated for 24 hours at 37° C. with shaking.

2) A paper disc (ADVANTEC, Φ:6 mm) was impregnated with a solution of test compound and dried under reduced pressure.

3) To a melted BHIB agar medium was inoculated 1% of the broth obtained from step 1) above to prepare a test plate. After the medium set, the paper disc prepared in step 2) above was put on the plate and it was incubated at 37° C.

4) After one day, the inhibition zone diameter and clarity (A to E) were determined. For KB346 strain, the same procedures were repeated.

The results of the assays are shown in Tables below:

TABLE 2

Mannhemia hemolytica KB345:

| | | Inhibition zone (mm) and clarity (A to E) | | | | |
|---|---|---|---|---|---|---|
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| Tylosin | — | 11.0A | 10.5B | — | — | — |
| Tilmicosin | 3,5-dimethylpiperidinylmethyl | NT | NT | 16.0A | 13.5A | 10.7A |
| Tulathromycin | — | NT | NT | 18.0A | 16.0A | 12.5A |
| YT6 | -CH(CHO)- | NT | 10.5A | — | — | — |
| YT7 | -CH(CH₂OH)- | — | — | — | — | — |
| YT8 | -CH(CH₂Cl)- | 20.0A | 18.0A | 12.5A | — | — |
| YT11 | -CH(CH₂N₃)- | 18.0A | 16.0A | 13.0A | 10.0A | — |
| YT12 | -CH₂-triazole-2-pyridyl | 22.0A | 19.0A | 17.0A | 13.0A | 9.0A |
| YT13 | -CH₂-triazole-phenyl | 21.0A | 18.0A | 16.0A | 15.0A | 11.0A |
| YT14 | -CH₂-triazole-thienyl | 22.0A | 19.5A | 16.5A | 14.0A | 11.0A |
| YT16 | -CH₂-triazole-3-pyridyl | 19.0A | 16.5A | 14.5A | 11.5A | — |
| YT17 | -CH₂-triazole-(3-aminophenyl) | 19.5A | 18.0A | 14.0A | 12.0A | — |

TABLE 2-continued
| | Mannhemia hemolytica KB345: | | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| YT18 | 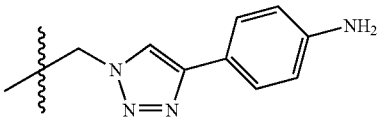 [SMILES: *Cn1cc(-c2ccc(N)cc2)nn1] | 19.5A | 17.0A | 14.5A | 11.0A | — |
| YT19 | 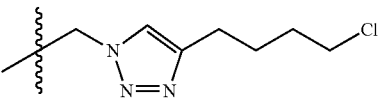 [SMILES: *Cn1cc(CCCCCl)nn1] | 21.0A | 18.0A | 16.0A | 14.0A | NT |
| YT20 | 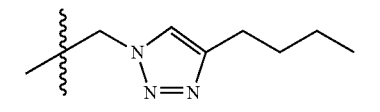 [SMILES: *Cn1cc(CCCC)nn1] | 20.0A | 17.5A | 16.0A | 11.5A | 9.0B |
| YT21 | 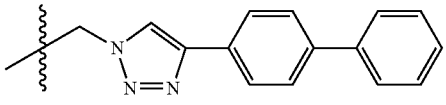 [SMILES: *Cn1cc(-c2ccc(-c3ccccc3)cc2)nn1] | 19.0A | 18.0A | 15.5A | 13.5A | 11.5A |
| YT22 | 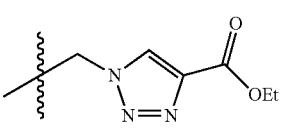 [SMILES: *Cn1cc(C(=O)OCC)nn1] | 21.0A | 18.0A | 14.5A | 11.5A | 7.5B |
| YT23 | 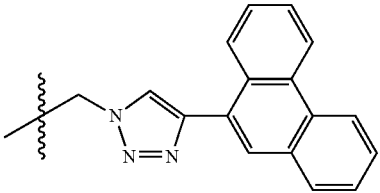 [SMILES: *Cn1cc(-c2cc3ccccc3c3ccccc23)nn1] | 16.5A | 14.5A | 13.5A | 10.0A | 7.5B |
| YT24 | 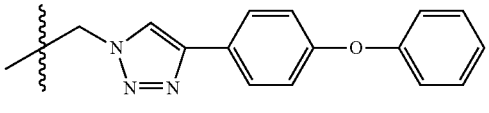 | 18.0A | 17.0A | 14.5A | 12.0A | 8.5B |
| YT25 | 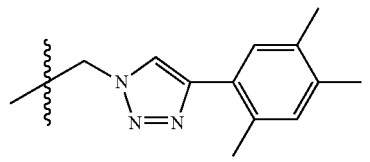 [SMILES: *Cn1cc(-c2cc(C)c(C)cc2C)nn1] | 18.5A | 17.0A | 14.0A | 12.0A | 8.0A |
| YT26 | 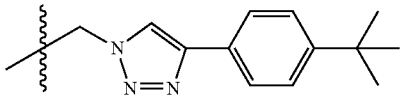 [SMILES: *Cn1cc(-c2ccc(C(C)(C)C)cc2)nn1] | 16.0A | 14.0A | 11.5A | 9.0A | — |
| YT27 | 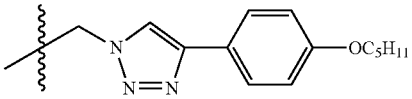 | 16.0A | 13.0A | 11.0A | 9.0A | — |
| YT28 | 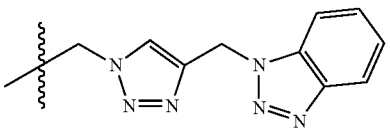 | 19.0A | 16.0A | 13.0A | 11.0A | — |

TABLE 2-continued

| | Mannhemia hemolytica KB345: | | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| YT29 | triazole-phenyl-N(CH3)2 | 20.0A | 17.5A | 16.0A | 13.5A | — |
| YT30 | triazole-CH2-NHCH3 | 10.0A | — | — | — | NT |
| YT32 | triazole-C(CH3)2-OH | 16.0A | 14.0A | 9.0A | — | NT |
| YT33 | triazole-isobutyl | 20.0A | 17.0A | 16.0A | 13.0A | NT |
| YT34 | triazole-(CH2)8 | 15.0A | 14.0A | 13.0A | 11.0B | NT |
| YT35 | triazole-quinoline | 21.0A | 19.0A | 17.0A | 14.0A | NT |
| YT36 | triazole-(CH2)4-OH | 9.0A | — | — | — | NT |
| YT37 | triazole-CH2-OH | 12.5A | 9.0A | — | — | NT |

TABLE 3

| | Mannhemia hemolytica KB346 | | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| Tylosin | — | 9.5 B | — | — | — | — |
| Tilmicosin | 3,5-dimethylpiperidine | NT | NT | 11.0 A | — | — |
| Tulathromycin | — | NT | NT | 14.0 A | 12.0 A | 9.5 A |

TABLE 3-continued

| | Mannhemia hemolytica KB346 | | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| YT6 | —CHO | 21.0 A | 17.5 A | 13.5 A | 8.5 A | — |
| YT7 | —OH | — | — | — | — | — |
| YT8 | —Cl | 14.5 A | 11.0 A | — | — | — |
| YT11 | —N₃ | 11.0 A | — | — | — | — |
| YT12 | triazole-pyridine | 16.0 A | 12.0 A | 9.0 B | — | — |
| YT13 | triazole-phenyl | 15.0 A | 12.0 A | 8.0 B | — | — |
| YT14 | triazole-thiophene | 17.0 A | 12.0 A | 9.0 B | — | — |
| YT16 | triazole-pyridine | 14.0 A | 11.0 A | 7.0 B | — | — |
| YT17 | triazole-aniline (m-NH₂) | 13.0 A | 9.0 A | — | — | — |
| YT18 | triazole-aniline (p-NH₂) | 12.5 A | 8.5 A | — | — | — |
| YT19 | triazole-(CH₂)₃Cl | 16.5 A | 14.0 A | 11.0 A | 7.0 A | — |

TABLE 3-continued
| | Mannhemia hemolytica KB346 | | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| YT20 | 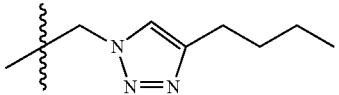 [SMILES: *Cn1cc(CCCC)nn1] | 17.5 A | 14.0 A | 10.5 A | — | — |
| YT21 | 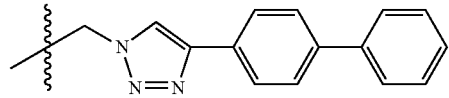 | 17.0 A | 14.0A | 12.5A | 9.0 A | — |
| YT22 | 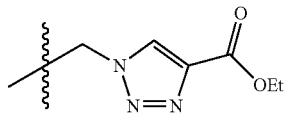 [SMILES: *Cn1cc(C(=O)OCC)nn1] | 16.0 A | 11.0 A | 9.0 B | — | — |
| YT23 | 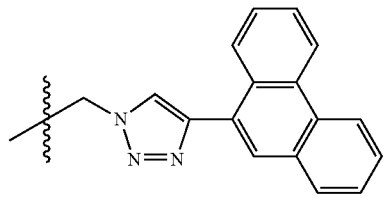 [SMILES: *Cn1cc(-c2cc3ccccc3c3ccccc23)nn1] | 11.0 A | 9.0 A | — | — | — |
| YT24 | 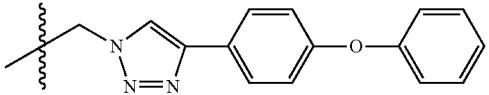 [SMILES: *Cn1cc(-c2ccc(Oc3ccccc3)cc2)nn1] | 9.0 B | — | — | — | — |
| YT25 | 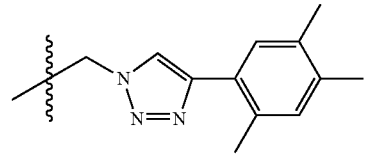 | 12.5 A | 8.5 A | — | — | — |
| YT26 | 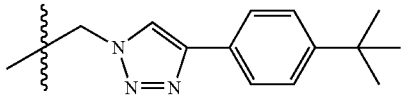 | — | — | — | — | — |
| YT27 | 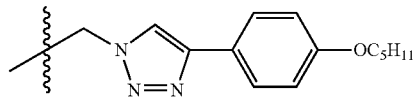 | — | — | — | — | — |
| YT28 | 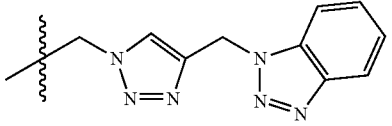 [SMILES: *Cn1cc(Cn2nnc3ccccc32)nn1] | 15.0 A | 10.0 A | — | — | — |
| YT29 | 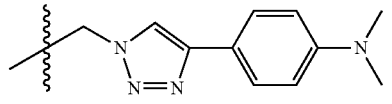 | 11.0 A | — | — | — | — |
| YT30 | 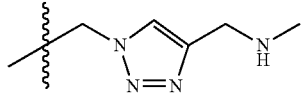 [SMILES: *Cn1cc(CNC)nn1] | 10.0 A | 8.0 B | — | — | — |

TABLE 3-continued

| | Mannhemia hemolytica KB346 | | | | | |
|---|---|---|---|---|---|---|
| | | Inhibition zone (mm) and clarity (A to E) | | | | |
| Sample | 20-position substituent | 100 mg/ 6 mm disk | 30 mg/ 6 mm disk | 10 mg/ 6 mm disk | 3 mg/ 6 mm disk | 1 mg/ 6 mm disk |
| YT32 | [1-triazolyl-C(CH₃)₂OH] | 13.5 A | 12.0 A | 8.0 B | — | — |
| YT33 | [1-triazolyl-isobutyl] | 14.5 A | 14.0 A | — | — | — |
| YT34 | [1-triazolyl-(CH₂)₈] | — | — | — | — | — |
| YT35 | [1-triazolyl-quinolin-3-yl] | 14.5 A | 13.5 A | — | — | — |
| YT36 | [1-triazolyl-(CH₂)₄OH] | 11.0 A | 8.0 A | — | — | — |
| YT37 | [1-triazolyl-CH₂OH] | — | — | — | — | — |

TABLE 4

| | Mannhemia hemolytica KB345 | | | | | | |
|---|---|---|---|---|---|---|---|
| | | | Inhibition zone (mm) and clarity (A to E) mg/6 mm disk) | | | | |
| Sample | 20-position substituent | 23-position substituent | 100 mg/ 6 mm disk | 30 mg/ 6 mm disk | 10 mg/ 6 mm disk | 3 mg/ 6 mm disk | 1 mg/ 6 mm disk |
| Tilmicosin | — | — | NT | | 18.0 A | 16.0 A | 12.0 A |
| Tylosin | — | — | 11.0 A | 10.5 B | — | — | — |
| YT106 | CHO | OH | 15.0 A | 12.5 A | 8.5 A | — | — |
| YT111 | CHO | I | 25.0 A | 20.0 A | 15.5 A | 11.5 A | NT |
| YT107 | CHO | N₃ | 21.5 A | 18.0 A | 16.0 A | 12.0 A | |

TABLE 4-continued

Mannhemia hemolytica KB345

| | | | Inhibition zone (mm) and clarity (A to E) mg/6 mm disk) | | | | |
|---|---|---|---|---|---|---|---|
| Sample | 20-position substituent | 23-position substituent | 100 mg/ 6 mm disk | 30 mg/ 6 mm disk | 10 mg/ 6 mm disk | 3 mg/ 6 mm disk | 1 mg/ 6 mm disk |
| YT101 | CHO | triazole-phenyl | 17.0 A | 14.0 A | 11.0 A | — | — |
| YT102 | CHO | triazole-(CH2)3 | 15.0 A | 11.5 A | 9.0 A | — | — |
| YT103 | CHO | triazole-quinoline | 16.0 A | 14.0 A | 12.0 A | — | — |
| YT104 | CHO | triazole-biphenyl | 12.5 A | 10.0 A | 10.0 A | 9.0 A | — |
| YT109 | CHO | triazole-pyridine | 12.5 A | 9.5 A | — | — | — |
| YT110 | CHO | triazole-CH2-benzotriazole | 11.5 A | 9.0 A | — | — | — |
| YT112 | triazole-phenyl | OH | 29.0 A | 25.0 A | 20.0 A | 17.0 A | NT |
| YT113 | triazole-phenyl | I | 19.5 A | 18.0 A | 11.0 A | — | NT |
| YT114 | triazole-phenyl | N3 | 21.0 A | 21.0 A | 17.5 A | 11.5 B | NT |
| YT115 | triazole-phenyl | triazole-phenyl | 16.0 A | 14.0 A | 12.0 A | — | NT |
| YT116 | triazole-phenyl | triazole-(CH2)3 | 17.0 A | 17.0 A | 13.0 A | — | NT |

TABLE 5

Mannhemia hemolytica KB346

| Sample | 20-position substituent | 23-position substituent | Inhibition zone (mm) and clarity (A to E) | | | | |
|---|---|---|---|---|---|---|---|
| | | | 100 mg/ 6 mm disk | 30 mg/ 6 mm disk | 10 mg/ 6 mm disk | 3 mg/ 6 mm disk | 1 mg/ 6 mm disk |
| Tilmicosin | — | — | NT | | 11.0 A | — | — |
| Tylosin | — | — | 11.0 A | 10.5 B | — | — | — |
| YT106 | CHO | CH₂OH | 17.0 A | 13.0 A | 9.0 A | — | — |
| YT111 | CHO | CH₂I | 13.0 A | 8.5 A | — | — | — |
| YT107 | CHO | CH₂N₃ | 15.0 A | 10.5 A | — | — | — |
| YT101 | CHO | triazole-phenyl | — | — | — | — | — |
| YT102 | CHO | triazole-(CH₂)₃ | — | — | — | — | — |
| YT103 | CHO | triazole-quinoline | — | — | — | — | — |
| YT104 | CHO | triazole-biphenyl | — | — | — | — | — |
| YT109 | CHO | triazole-pyridine | 9.0 A | — | — | — | — |
| YT110 | CHO | triazole-CH₂-benzotriazole | 8.0 A | — | — | — | — |
| YT112 | triazole-phenyl | CH₂OH | 11.5 A | — | — | — | — |
| YT113 | triazole-phenyl | CH₂I | — | — | — | — | — |

TABLE 5-continued

Mannhemia hemolytica KB346

| Sample | 20-position substituent | 23-position substituent | Inhibition zone (mm) and clarity (A to E) | | | | |
|---|---|---|---|---|---|---|---|
| | | | 100 mg/ 6 mm disk | 30 mg/ 6 mm disk | 10 mg/ 6 mm disk | 3 mg/ 6 mm disk | 1 mg/ 6 mm disk |
| YT114 | [4-phenyl-1,2,3-triazol-1-ylmethyl] | [azidomethyl] | — | — | — | — | — |
| YT115 | [4-phenyl-1,2,3-triazol-1-ylmethyl] | [4-phenyl-1,2,3-triazol-1-ylmethyl] | — | — | — | — | — |
| YT116 | [4-phenyl-1,2,3-triazol-1-ylmethyl] | [(1,2,3-triazol-1-yl)propyl] | — | — | — | — | — |

(2) Antibacterial activities against other bacteria were determined with *Micrococcus luteus* ATCC9341 (1), *Bacillus subtilis* ATCC663 (s), *Escherichia coli* NIHJ (c), *Xanthomonas campestris* KB88 (X), *Mucor racemosus* IFO 4581 (Mu) and *Candida albicans* ATCC 64548 (Ca).

*Bacillus subtilis* ATCC6633 was incubated in Davis synthetic medium and then the seed broth was combined with the medium in the ratio of 1:99 to obtain a test plate. *Micrococcus luteus* ATCC9341, *Escherichia coli* NIHJ and *Xanthomonas campestris* KB88 were respectively incubated in Nutrient agar medium and inoculated at 0.2%, 0.5% and 1.0%. *Mucor racemosus* IFO 4581 and *Candida albicans* ATCC 64548 were respectively incubated in GY agar medium and then inoculated at 0.3% and 0.2%.

A paper disc (ADVANTEC, Φ:6 mm) was impregnated with a solution of test compound and dried under reduced pressure. The paper disc was put on the test plate and it was incubated for 24 hours at 37° C. After incubation, the inhibition zone diameter and clarity (A to E) were determined.

The results of the assays are shown in Table 6 below:

TABLE 6

Six bacteria

| Sample | 20-position substituent | mg/ 6 mm disc | Inhibition zone (mm) and clarity | | | | | |
|---|---|---|---|---|---|---|---|---|
| | | | S | 1 | c | X | Ca | Mu |
| Tilmicosin | [3,5-dimethylpiperidinylmethyl] | 10 | 18 A | 27.5 A | 20 C | 30 C | — | — |
| | | 1 | 11 A | 19 A | 13 C | 20 C | — | — |
| | | 0.1 | 14 C | 12 A | — | 12 C | — | — |
| YT12 | [4-(pyridin-3-yl)-1,2,3-triazol-1-ylmethyl] | 10 | 14 A | 25 A | — | 27 B | — | — |
| | | 1 | 12.5 A | 18.5 A | — | 12.5 B | — | — |
| | | 0.1 | 7 A | 12 A | — | 7 B | — | — |
| YT13 | [4-phenyl-1,2,3-triazol-1-ylmethyl] | 10 | 15.5 A | 27.5 A | — | 23.5 B | — | — |
| | | 1 | 12 A | 21.5 A | — | 17 B | — | — |
| | | 0.1 | 9.5 A | 15 A | — | 8 B | — | — |
| YT14 | [4-(thiophen-2-yl)-1,2,3-triazol-1-ylmethyl] | 10 | 15 A | 26.5 A | 7 B | 22 B | — | — |
| | | 1 | 11 A | 20.5 A | — | 16 B | — | — |
| | | 0.1 | 8 A | 13.5 A | — | 7 B | — | — |

TABLE 6-continued

Six bacteria

| Sample | 20-position substituent | mg/ 6 mm disc | Inhibition zone (mm) and clarity | | | | | |
|---|---|---|---|---|---|---|---|---|
| | | | S | I | c | X | Ca | Mu |
| YT19 | -CH2-(1,2,3-triazol-1-yl), 4-(CH2)4Cl on triazole | 10 | 15 A | 26 A | — | 23 B | — | — |
| | | 1 | 10.5 A | 19 A | — | 14.5 B | — | — |
| | | 0.1 | 7 A | 13 A | — | 7 B | — | — |
| YT29 | -CH2-(1,2,3-triazol-1-yl), 4-(4-dimethylaminophenyl) on triazole | 10 | 15 A | 25.5 A | — | 24 B | — | — |
| | | 1 | 10 A | 19.5 A | — | 15 B | — | — |
| | | 0.1 | 7 A | 11 A | — | 7 B | — | — |

Minimal inhibitory concentrations (MICs) were determined against the most prevalent pathogens in cattle (Mannheimia Haemolytica, 3 isolates) and swine (A. pleuropneumoniae, 6 isolates). The results are summarized in Table 7.

TABLE 7

MICs (μg/ml)

| | M. haemolytica isolate | | | pleuropneumoniae isolates | | | | | |
|---|---|---|---|---|---|---|---|---|---|
| Compound | 1 | 2 | 3 | 1 | 2 | 3 | 4 | 5 | 6 |
| YT104 | 8 | 4 | 8 | >16 | >16 | >16 | >16 | >16 | >16 |
| YT112 | 8 | 4 | 8 | 4 | 4 | 4 | 8 | 4 | 8 |

(3) Activity against Bacterial Mastitis Pathogens

The activity of several compounds against bacterial mastitis pathogens has been tested under in-vitro conditions according to a recognized procedure (CLSI, document M31-A3, 2008). In this test 7 to 12 representative bacteria belonging to 7 bacterial species that typically cause mastitis in dairy cattle, i.e. *Staphylococcus aureus*, coagulase negative staphylococci (CNS), *Streptococcus uberis*, *Streptococus dysgalactiae*, *Streptococcus agalactiae*, *Arcanobacterium pyogenes* and *Escherichia coli*, were exposed to twofold dilutions of the test compounds. After 24 hours of incubation the concentration that inhibited the growth of this bacteria was determined. The results are shown in table 8 below. It could be shown that all these bacterial mastitis pathogens were highly susceptible to the test compounds.

TABLE 8

Minimum inhibitory concentration (broth dilution method) inhibiting 50% of a population (MIC50, μg/mL) of 7 to 12 isolates belonging to 7 distinct mastitis-causing bacterial species (*Staphylococcus aureus*, coagulase negative staphylococci [CNS], *Streptococcus uberis*, *Streptococus dysgalactiae*, *Streptococcus agalactiae*, *Arcanobacterium pyogenes* and *Escherichia coli*)

| Compound | S. aureus | CNS | Str uberis | Str dysgalactiae | Str agalactiae | A. pyogenes | E. coli |
|---|---|---|---|---|---|---|---|
| YT650 | 0.25 | 0.25 | 0.03 | 0.03 | 0.008 | 0.004 | 8 |
| YT709 | ≤0.03 | ≤0.03 | 0.06 | 0.06 | 0.06 | 0.008 | 16 |
| YT721 | 0.5 | 0.5 | 0.12 | 0.25 | 0.125 | 0.06 | 8 |
| YT732 | 0.5 | 0.25 | 0.03 | 0.12 | 0.03 | 0.008 | 8 |
| YT739 | 0.5 | 0.25 | 0.03 | 0.12 | 0.03 | 0.008 | 8 |
| YT762 | 1 | 0.25 | 0.03 | 0.12 | 0.03 | 0.015 | 8 |
| YT769 | 0.25 | 0.25 | ≤0.015 | ≤0.015 | ≤0.015 | ≤0.015 | 4 |
| YT770 | 0.25 | 0.25 | 0.03 | 0.03 | ≤0.015 | ≤0.015 | 4 |
| YT773 | 0.25 | 0.12 | ≤0.015 | ≤0.015 | ≤0.015 | ≤0.015 | 16 |
| YT794 | 0.25 | 0.25 | 0.12 | 0.06 | 0.12 | ≤0.015 | ≥16 |

In addition the activity of several compounds was tested against two bacterial species, i.e. *Mannheimia haemolytica* and *Actinobacillus pleuropneumoniae*, which are considered as the most important bacterial respiratory pathogens in cattle and swine, respectively. As shown in table 9 below these compounds were highly active against these respiratory pathogens.

TABLE 9

Range of minimum inhibitory concentrations (MIC, μg/mL, broth dilution method) against 3 *Mannheimia haemolytica* isolates and 6 *Actinobacillus pleuropneumoniae* isolates

| Compound | M. haemolytica | A. pleuropneumoniae |
|---|---|---|
| YT617 | 2-8 | 4 |
| YT653 | 1-8 | 4-8 |
| YT657 | 2-4 | 2 |
| YT664 | 4-8 | 2-8 |
| YT674 | 2-4 | 2 |
| YT679 | 4-8 | 2-4 |
| YT700 | 4-8 | 8 |
| YT705 | 8 | 8 |
| YT709 | 2-4 | 2-4 |
| YT710 | 2-4 | 4 |
| YT717 | 2-8 | 4 |
| YT718 | 2-8 | 8 |
| YT721 | 1-4 | 8 |
| YT723 | 2-8 | 8 |

TABLE 9-continued

Range of minimum inhibitory concentrations (MIC, μg/mL, broth dilution method) against 3 *Mannheimia haemolytica* isolates and 6 *Actinobacillus pleuropneumoniae* isolates

| Compound | M. haemolytica | A. pleuropneumoniae |
|---|---|---|
| YT726 | 8 | 8 |
| YT732 | 1-4 | 2-4 |
| YT733 | 2-4 | 4 |
| YT734 | 2-4 | 2-4 |

The clinical efficacy of compound YT709 against mastitis caused by *S. aureus* was shown in lactating mice according to a recognized published procedure (E. Brouillette, G. Grondin, C. Lefebvre, B. G. Talbot, F. Malouin, Mouse mastitis model of infection for antimicrobial compound efficacy studies against intracellular and extracellular forms of *Staphylococcus aureus*, Veterinary Microbiology, 101, (2004), 253-262). Into the glands of lactating mice *S. aureus* bacteria (strain Newbould) were instilled and allowed to multiply. Bacterium *S. aureus* Newbould is an isolate which was isolated from a clinical case of bovine mastitis and which also causes typical mastitis infection in dairy cattle upon experimental, intramammary infection. Four hours after the intramammary infection of lactating mice with *S. aureus* Newbould, compound YT709 was instilled into the infected glands. Different intramammary dosages of YT709 were tested and their efficacy compared to an infected, untreated control group. Fourteen hours after intramammary application of YT709, the glands of the treated and untreated mice were removed, homogenized and the number of *S. aureus* bacteria counted in 10-fold dilutions of the homogenized glands. The mean *S. aureus* count of 8 untreated glands was $10^{8.64}$ (8.64 log 10) bacteria. The mean *S. aureus* count in 6 glands that had been treated with 200 microgram YT709 was $10^{5.10}$ bacteria (5.10 log 10). Hence in the glands treated with 200 microgram YT709 the number of bacteria was reduced about 3500 fold. The mean *S. aureus* count in the 5 glands that had been treated with 400 microgram YT709 was $10^{2.34}$ bacteria (2.34 log 10). Hence in the glands treated with 400 microgram YT-709 the number of bacteria was reduced about two million fold. In the mice from which the lactating glands had been treated with 400 microgram YT709, *S. aureus* bacteria could not be counted anymore in measurable numbers and hence in 2 out of 5 glands the infection was cleared.

All references, patent applications and publications cited herein are hereby incorporated by reference in its entirety.

The invention claimed is:

1. A compound represented by the formula (IIa):

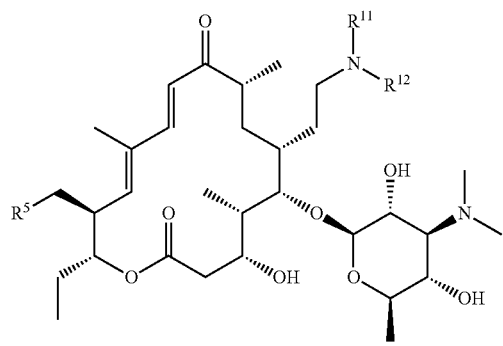

(IIa)

or a pharmaceutically acceptable salt, ester, prodrug or solvate thereof;

wherein, $R^{11}$ and $R^{12}$ are each independently selected from
hydrogen;
—CHO;
$C_1$-$C_6$—X, wherein X is selected from the group consisting of hydroxyl or protected hydroxyl, halogen, and $N_3$;
CN;
C1-C6-alkyl, optionally substituted with one or more substituents selected from the group consisting of halogen, aryl, substituted aryl, heterocyclic and substituted heterocyclic;
C2-C6-alkenyl, optionally substituted with one or more substituents selected from the group consisting of halogen, aryl, substituted aryl, heterocyclic and substituted heterocyclic;
C2-C6-alkynyl, optionally substituted with one or more substituents selected from the group consisting of halogen, aryl, substituted aryl, heterocyclic and substituted heterocyclic;
C3-C14 cycloalkyl
substituted C3-C14-cycloalkyl;
aryl;
substituted aryl;
heterocyclic;
substituted heterocyclic;
and wherein at least $R^{11}$ or $R^{12}$ is C1-C6-alkyl, optionally substituted with one or more substituents selected from the group consisting of halogen, aryl, substituted aryl, heterocyclic and substituted heterocyclic; and
wherein $R^5$ is
hydroxyl.

2. The compound of claim 1, wherein:
at least $R^{11}$ or $R^{12}$ is C1-C6-alkyl, substituted with one substituent selected from the group consisting of heterocyclic and substituted heterocyclic.

3. A method for treating or preventing bacterial infections or disorders associated with bacterial infections in an animal, wherein the method comprises administering to the animal a therapeutically effective amount of the compound according to claim 1.

4. A pharmaceutical or veterinary composition comprising a compound according to claim 1 and at least one pharmaceutically acceptable carrier.

5. The pharmaceutical or veterinary composition of claim 4 for use in the treatment or prevention of bacterial infections or disorders associated with bacterial infections in an animal.

6. A method for treating or preventing bacterial infections or disorders associated with bacterial infections in an animal, wherein the method comprises administering to the animal a therapeutically effective amount of the composition according to claim 4.

7. The compound of claim 1, wherein at least $R^{11}$ or $R^{12}$ is C1-C3-alkyl, substituted with one substituent selected from the group consisting of heterocyclic and substituted heterocyclic.

8. The compound of claim 1, wherein at least $R^{11}$ or $R^{12}$ is C1-C3-alkyl, substituted with a 1,2,3-triazole substituted at position 4 with one substituent selected from the group consisting of heterocyclic and substituted heterocyclic.

9. The compound of claim 1, wherein one of $R^{11}$ and $R^{12}$ is C1-C6-alkyl, substituted with one substituent selected from the group consisting of heterocyclic and substituted heterocyclic, and the other one of $R^{11}$ and $R^{12}$ is
hydrogen or
C1-C6-alkyl, optionally substituted with one or more substituents selected from the group consisting of halogen, aryl, substituted aryl, heterocyclic and substituted heterocyclic.

10. A compound of claim 1, wherein $R^{11}$ or $R^{12}$ is C1-C3-alkyl, substituted with one substituent selected from the group consisting of heterocyclic and substituted heterocyclic, and the other one of $R^{11}$ and $R^{12}$ is hydrogen or C1-C3-alkyl, optionally substituted with one or more substituents selected from the group consisting of halogen, aryl, substituted aryl, heterocyclic and substituted heterocyclic.

11. A compound of claim 1, wherein one of $R^{11}$ and $R^{12}$ is C1-C2-alkyl, substituted with a 1,2,3-triazole substituted at position 4 with one substituent selected from the group consisting of heterocyclic and substituted heterocyclic, and the other one of $R^{11}$ and $R^{12}$ is hydrogen or C1-C2-alkyl, optionally substituted with one substituent selected from the group consisting of aryl and substituted aryl.

* * * * *